United States Patent
Lahm et al.

(10) Patent No.: US 11,278,533 B2
(45) Date of Patent: Mar. 22, 2022

(54) ANIMAL PEST CONTROL METHOD

(75) Inventors: George Philip Lahm, Wilmington, DE (US); Jeffrey Keith Long, Wilmington, DE (US); Ming Xu, Newark, DE (US)

(73) Assignee: E.I. DU PONT DE NEMOURS AND COMPANY, Wilmington, DE (US)

( * ) Notice: Subject to any disclaimer, the term of this patent is extended or adjusted under 35 U.S.C. 154(b) by 2415 days.

(21) Appl. No.: 12/663,848

(22) PCT Filed: Jun. 26, 2008

(86) PCT No.: PCT/US2008/068268
§ 371 (c)(1),
(2), (4) Date: Dec. 10, 2009

(87) PCT Pub. No.: WO2009/003075
PCT Pub. Date: Dec. 31, 2008

(65) Prior Publication Data
US 2010/0173948 A1 Jul. 8, 2010
US 2015/0272938 A2 Oct. 1, 2015

Related U.S. Application Data

(60) Provisional application No. 60/937,389, filed on Jun. 27, 2007.

(51) Int. Cl.
*A61K 31/4439* (2006.01)
*A61K 31/42* (2006.01)
*A01N 43/80* (2006.01)
*A61K 9/00* (2006.01)

(52) U.S. Cl.
CPC .......... *A61K 31/4439* (2013.01); *A01N 43/80* (2013.01); *A61K 9/0019* (2013.01); *A61K 9/0053* (2013.01); *A61K 31/42* (2013.01)

(58) Field of Classification Search
CPC ... A61K 31/42; A61K 31/4439; C07D 261/04
USPC .......................................... 548/240; 514/378
See application file for complete search history.

(56) References Cited

U.S. PATENT DOCUMENTS

| 3,879,532 | A |   | 4/1975  | Hass et al. |
|-----------|---|---|---------|---------------------|
| 3,968,207 | A | * | 7/1976  | Schrider ........ A01N 57/14 |
|           |   |   |         | 514/104 |
| 4,129,568 | A |   | 12/1978 | Howe |
| 6,136,838 | A |   | 10/2000 | Chern et al. |

(Continued)

FOREIGN PATENT DOCUMENTS

| AU | 673329 B | 2/1994 |
| AU | 2005219788 | 9/2005 |

(Continued)

OTHER PUBLICATIONS

Mita et al (2007): STN International HCAPLUS database, Columbus (OH), accession No. 2007: 330406.*
Notice of allowance dated Jan. 11, 2011 received in copending U.S. Appl. No. 12/086,9351.
U.S. Appl. No. 12/083,943, filed Apr. 21, 2008, now abandoned.
Office Action dated Jan. 23, 2012 received in copending U.S. Appl. No. 12/677,927.
Mita et al. (2007): STN International HCAPLUS database, (Columbus, Ohio), Accession Number: 2009:740002.
Motoki et al., "Copper(I) alkoxide-catalyzed alkynylation of trifluoromethyl ketones," Organic Letters (2007) 9 (16):2997-3000.
Lahm et al (2007): STN International HCAPLUS database, Columbus (OH), accession number: 2007:755410.
Non-final Office Action dated Nov. 28, 2011 received in copending U.S. Appl. No. 12/663,751.
Konno et al., "Palladium-Catalyzed Regio- and Stereoselective Formate Reduction of Fluorine-Containing Allylic Mesylates. A New Entry for the Construction of a Tertiary Carbon Attached with a Fluoroalkyl Group," Journal of Organic Chemistry (2006) 71(9):3545-3550.
Carey et al., "Advanced Organic Chemistry," 2ed., Part B: Reactions and Synthesis, (1983) Pelenum Press, New York.
Sosnovskii et al., "Ketone-ketone condensation with participation of polyhaloalkyl phenyl ketones," Journal of Organic Chemistry of the USSR, (1992) 28:420-426.
Kamble et al., "An efficient synthesis of pharmacologically active derivatives 1,3,4-Oxadiazoles," Journal of Heterocyclic Chemistry (2006) 43(345):345-352.

(Continued)

*Primary Examiner* — Matthew P Coughlin
(74) *Attorney, Agent, or Firm* — John Ezcurra

(57) ABSTRACT

Disclosed is a method for protecting an animal from a parasitic invertebrate pest comprising treating an animal orally or by injection with a pesticidally effective amount of a compound of Formula 1,

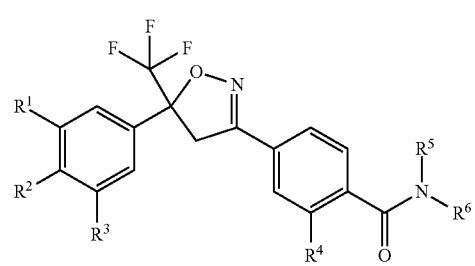

wherein
$R^1$ is halogen, $C_1$-$C_3$ haloalkyl or $C_1$-$C_3$ haloalkoxy;
$R^2$ is H, halogen, $C_1$-$C_3$ alkyl, $C_1$-$C_3$ haloalkyl or cyano;
$R^3$ is H, halogen, $C_1$-$C_3$ haloalkyl or $C_1$-$C_3$ haloalkoxy;
$R^4$ is halogen, $C_1$-$C_3$ alkyl, $C_1$-$C_3$ haloalkyl or $C_1$-$C_3$ haloalkoxy;
$R^5$ is H, $CH_3$, $C_2$-$C_4$ alkylcarbonyl, $C_2$-$C_4$ haloalkylcarbonyl, $C_2$-$C_5$ alkoxycarbonyl or $CH_2O(C_1$-$C_3$ alkyl);
$R^6$ is $C_1$-$C_6$ alkyl, $C_1$-$C_6$ haloalkyl, $C_3$-$C_6$ cycloalkyl or $C_3$-$C_6$ halocycloalkyl, each group substituted with one $R^7$; or $R^6$ is $(CH_2)_mQ$;
and Q, $R^7$, $R^{8a}$ and $R^{8b}$ are as defined in the disclosure.

5 Claims, No Drawings

(56) References Cited

U.S. PATENT DOCUMENTS

| | | | |
|---|---|---|---|
| 6,140,350 | A | 10/2000 | Sembo |
| 6,162,820 | A * | 12/2000 | Jeannin ............... A01N 43/56 514/407 |
| 6,346,542 | B1 | 2/2002 | Huber |
| 6,645,984 | B2 | 11/2003 | Braun et al. |
| 6,664,237 | B1 * | 12/2003 | Snyder ............... A01N 43/22 514/28 |
| 7,468,381 | B2 | 12/2008 | Huber et al. |
| 7,662,972 | B2 * | 2/2010 | Mita et al. .............. 548/240 |
| 7,897,630 | B2 | 3/2011 | Lahm et al. |
| 7,947,715 | B2 | 5/2011 | Mita et al. |
| 7,951,828 | B1 * | 5/2011 | Mita et al. ............... 514/378 |
| 7,964,204 | B2 * | 6/2011 | Lahm et al. ............. 424/405 |
| 8,022,089 | B2 * | 9/2011 | Mita et al. ............... 514/378 |
| 8,138,213 | B2 * | 3/2012 | Mita et al. ............... 514/378 |
| 8,217,180 | B2 | 7/2012 | Annis et al. |
| 88,231,888 | | 7/2012 | George Philip Lahm et al. |
| 8,410,153 | B2 | 4/2013 | Lahm et al. |
| 8,513,431 | B2 | 8/2013 | Annis et al. |
| 2003/0114501 | A1 | 6/2003 | Braun et al. |
| 2003/0139459 | A1 | 7/2003 | Tinembart et al. |
| 2004/0069235 | A1 | 4/2004 | Rasa et al. |
| 2005/0250822 | A1 | 11/2005 | Mita et al. |
| 2007/0066617 | A1 | 3/2007 | Mita et al. |
| 2007/0072944 | A1 | 3/2007 | Gauvry et al. |
| 2009/0023923 | A1 | 1/2009 | Mizukoshi et al. |
| 2009/0133319 | A1 | 5/2009 | Lahm et al. |
| 2009/0143410 | A1 | 6/2009 | Patel |
| 2010/0137612 | A1 | 6/2010 | Yaosaka et al. |
| 2010/0173948 | A1 | 7/2010 | Lahm et al. |
| 2010/0179195 | A1 | 7/2010 | Lahm et al. |
| 2010/0249424 | A1 | 9/2010 | Annis et al. |
| 2010/0254959 | A1 | 10/2010 | Lahm et al. |
| 2010/0254960 | A1 | 10/2010 | Long et al. |
| 2011/0059988 | A1 | 3/2011 | Heckeroth |

FOREIGN PATENT DOCUMENTS

| | | |
|---|---|---|
| AU | 2008268321 | 12/2008 |
| AU | 2008290581 | 2/2009 |
| AU | 2013207369 | 5/2016 |
| CA | 2252543 | 11/1997 |
| CA | 2558848 | 9/2005 |
| CA | 2621228 | 3/2007 |
| CA | 2632694 | 7/2007 |
| CA | 2684632 | 12/2008 |
| CN | 1498213 | 5/2004 |
| CN | 101346336 | 1/2009 |
| EA | 000924 | 6/2000 |
| EP | 074069 | 3/1983 |
| EP | 0216541 | 4/1987 |
| EP | 07016152.6 | 5/1999 |
| EP | 1538138 | 6/2005 |
| EP | 1731512 | 12/2006 |
| EP | 07150309.8 | 12/2007 |
| EP | 1975149 | 10/2008 |
| EP | 2172462 | 4/2010 |
| EP | 2 190 289 | 6/2010 |
| EP | 1973888 | 1/2011 |
| EP | 2155701 | 12/2013 |
| GB | 0 331 242 | 5/1999 |
| GB | 2351081 | 12/2000 |
| JP | 199859944 | 3/1998 |
| JP | 1999503114 | 3/1999 |
| JP | 2004529130 | 9/2004 |
| JP | 2005272452 | 10/2005 |
| JP | 2007016017 | 1/2007 |
| JP | 2007106756 | 4/2007 |
| KZ | 13246 | 7/2003 |
| KZ | 16356 | 10/2005 |
| RU | 99101948 | 10/2001 |
| RU | 2433123 | 11/2011 |
| TW | 200738696 | 10/2007 |
| WO | 90/07274 | 7/1990 |
| WO | 9854122 | 12/1998 |
| WO | 99/47139 | 9/1999 |
| WO | 01/11963 | 2/2001 |
| WO | 0140222 | 6/2001 |
| WO | 200499197 | 11/2004 |
| WO | 2005/013714 A1 | 2/2005 |
| WO | 2005/041950 | 5/2005 |
| WO | 2005085216 | 6/2005 |
| WO | 2005/085216 | 9/2005 |
| WO | 2005094329 | 10/2005 |
| WO | 2006/010767 | 2/2006 |
| WO | 2006135640 | 12/2006 |
| WO | 2007026965 | 3/2007 |
| WO | 2007/070606 | 6/2007 |
| WO | 2007070606 | 6/2007 |
| WO | WO 2007070606 | 6/2007 |
| WO | 2007/079162 | 7/2007 |
| WO | 2007074789 | 7/2007 |
| WO | 2007075459 | 7/2007 |
| WO | 2007079162 | 7/2007 |
| WO | 2007105814 | 9/2007 |
| WO | 2007123855 | 11/2007 |
| WO | 2007125984 | 11/2007 |
| WO | 2008019760 | 2/2008 |
| WO | 2008108448 | 9/2008 |
| WO | 2008122375 | 10/2008 |
| WO | 2009/003075 | 12/2008 |
| WO | 2008154528 | 12/2008 |
| WO | 2009001942 | 12/2008 |
| WO | 2009002809 | 12/2008 |
| WO | 2009003075 | 12/2008 |
| WO | 2009/024541 | 2/2009 |
| WO | 2009025983 | 2/2009 |
| WO | 2009045999 | 4/2009 |
| WO | 2009126668 | 10/2009 |

OTHER PUBLICATIONS

Database Chemical Abstracts Service (1988) XP002516318, Database accession No. 111:115084.

Ragaila et al., "Newer heterocycles and carbamates from naphthyl," Egyptian Journal of Pharmaceutical Sciences (1988) 29(1-4):71-87.

Database Chemical Abstracts Service (1996) XP002516333, Database Accession No. 126:31303.

Kuznetsova et al., "Synthesis of fluorine-containing functionalized isoxazolines," Russian Chemical Bulletin (1996) 45 (5):1245-1246.

Notice of Allowance dated Jan. 1, 2011 received in copending U.S. Appl. No. 12/086,935.

Notice of Allowance dated Sep. 28, 2010 received in copending U.S. Appl. No. 12/086,935.

Notice of Allowance dated Oct. 21, 2010 received in copending U.S. Appl. No. 12/083,944.

Non-final Office Action dated May 19, 2010 received in copending U.S. Appl. No. 12/083,944.

Non-final Office Action dated Dec. 16, 2009 received in copending U.S. Appl. No. 12/083,944.

Non-final Office Action dated Aug. 3, 2009 received in copending U.S. Appl. No. 12/083,944.

Dighade et al,. "Effect of solvents in synthesis of new 4-(2-hydroxy-5-methylphenyl)-6-aryl-2-imino-6H-2,3-dihydro-1,3-thiazines," Asian Journal of Chemistry (2001) 13(4):1560-1564.

International Search Report dated Feb. 24, 2011 received in copending International Application No. PCT/US2009/039832 (citing Carey et al.).

Office Action dated Sep. 21, 2011 received in copending U.S. Appl. No. 13/156,653.

Office Action dated Feb. 6, 2012 received in copending U.S. Appl. No. 12/602,821.

Notice of Allowance and Fee(s) due dated Mar. 18, 2012 received in copending U.S. Appl. No. 12/679,382.

Notice of Allowance and Fee(s) due dated Mar. 21, 2012 received in copending U.S. Appl. No. 13/156,653.

Advisory Action dated Sep. 6, 2012 received in copending U.S. Appl. No. 12/677,927.

(56) References Cited

OTHER PUBLICATIONS

Office Action dated Aug. 14, 2012 received in copending U.S. Appl. No. 13/933,493.
Office Action dated Jul. 2, 2012 received in copending U.S. Appl. No. 12/677,927.
Office Action dated Jun. 8, 2012 received in copending U.S. Appl. No. 12/663,751.
Office Action dated Jun. 26, 2012 received in copending U.S. Appl. No. 12/602,821.
[Kuznetsova et al., "Synthesis of fluorine-containing functionalized isoxazolines," Proceedings of the Academy of Sciences (1996) 5:1306-1307]. English Translation of Russian Office Action received Jul. 3, 2012 attached.
Notice of Allowance dated Sep. 24, 2012 received in copending U.S. Appl. No. 12/677,927.
Office Action dated Nov. 23, 2012 received in counterpart U.S. Appl. No. 13/561,546.
Notice of Allowance dated Nov. 14, 2012 received in counterpart U.S. Appl. No. 12/663,751.
Final Office Action dated Mar. 13, 2013 received in copending U.S. Appl. No. 12/602,821.
Office Action dated Aug. 27, 2014 received in copending U.S. Appl. No. 14/148,410.
Parrilla et al., "Synthesis of trifluoromethyl ketones as inhibitors of antennal esterases of insects," Bioorganize & Medicinal Chemistry (1994) 2(4):243-252.
Creary "Reaction of Organometallic Reagents with Ethyl Trifluoroacetate and Diethyl Oxalate. Formation of Trifluoromethyl Ketones and alpha-Keto Esters via Stable Tetrahedral Adducts," Journal of Organic Chemistry (1987) 52:5026-5030.
Office Action dated Jan. 3, 2014 received in copending U.S. Appl. No. 13/037,257.
Notice of Allowance dated Aug. 23, 2013 received in copending U.S. Appl. No. 12/602,821.
Notice of Allowance dated Jun. 7, 2013 received in copending U.S. Appl. No. 13/561,546.
Notice of Allowance dated May 14, 2013 received in copending U.S. Appl. No. 12/933,493.
Notice of Allowance dated Apr. 15, 2013 received in copending U.S. Appl. No. 13/544,113.
Final Office Action dated Jun. 8, 2012 received in copending U.S. Appl. No. 12/663,751.
Office Action dated Dec. 12, 2013 received in copending U.S. Appl. No. 14/047,500.
Office Action dated Jun. 13, 2014 received in copending U.S. Appl. No. 14/041,938.
Sato et al., Science of Synthesis (2005) 18:821 [pp. IV and 924].
Notice of Allowance dated Jun. 24, 2014 received in copending U.S. Appl. No. 14/275,664.
Office Action dated Jul. 15, 2014 received in copending U.S. Appl. No. 13/037,257.
Notice of Allowance dated Jan. 15, 2015 received in copending U.S. Appl. No. 14/041,938.
Trends in Parasitology vol. 11 No. 5 (May 2005).
Trends in Parasitology vol. 21 No. 5 (May 2005) 232-236.
Veterinary Parasitology 104(2002)257-264.
Notice of Appeal of Decision in Opposition to European Patent No. 2 182 945 dated Jun. 1, 2018.
Decision in Opposition to European Patent No. 2 182 945 dated Apr. 3, 2018.
Minutes of Oral Proceeding in Opposition to European Patent No. 2 182 945 dated Apr. 3, 2018.
Summons to Attend Oral Proceedings in Opposition to European Patent No. 2 182 945 dated Jun. 21, 2017.
Nissan Chemical Ind., Ltd, Submissions dated Dec. 21, 2017 in Opposition to EP Patent No. 2 182 945.
E. I. Du Pont De Nemours and Company, Submissions dated Dec. 21, 2017 in Opposition to EP Patent No. 2 182 945 together with cited documents D68 and D70-D84.
Second Declaration of Dr. Jeffrey N. Clark dated Dec. 18, 2017 filed in Opposition to EP Patent No. 2 182 945 as document D69.
Intervet International B.V., Submissions dated Dec. 22, 2017 in Opposition to EP Patent No. 2 182 945.
Virbac, Submissions dated Jan. 25, 2017 and English translation thereof in Opposition to EP Patent No. 2 182 945.
Intervet International B.V., Submissions dated Feb. 5. 2018 in Opposition to EP Patent No. 2 182 945.
Nissan Chemical Ind., Ltd, Submissions dated Feb. 16, 2018 in Opposition to EP Patent No. 2 182 945.
Virbac, Submissions dated Feb. 20, 2018 and English translation thereof in Opposition to EP Patent No. 2 182 945.
E. I. Du Pont De Nemours and Company, Submissions dated Feb. 22, 2018 in Opposition to EP Patent No. 2 182 945.
E. I. Du Pont De Nemours and Company, Submissions dated Dec. 16, 2016 in Opposition to EP Patent No. 2 182 945.
Ntervet International B.V., Statement of Grounds and Particulars in Opposition to AU 2014259503 dated Jan. 2, 2018.
Third Party Observations in Japanese Patent Application No. 2010-515096 dated Oct. 24, 2014.
Intervet International B.V. "Regulation 5.23 Appendices I-XI" filed by Intervet International B.V. on Jun. 22, 2016.
Intervet International B.V. Response to Communication pursuant to Article 94(3) filed Sep. 23, 2011 in European Application No. 08803041.6.
Intervet International B.V. Response to Official Communication pursuant to Article 112(1) EPC filed May 22, 2014 in European Application No. 12188400.1.
Intervet International B.V. Statement of Grounds & Particulars of Opposition filed Feb. 9, 2015, in Australian Application No. 2008268321.
Intervet International B.V. Supplemental Submissions by Opponent dated Apr. 21, 2017 in Opposition to EP Patent No. 2 182 945 (EP Application No. 08 7771 978.7).
Kaminsky. Expert Report of Dr. Ronald Kaminsky dated Apr. 24, 2016, Annex 1.
Kaminsky. Expert Report of Dr. Ronald Kaminsky dated Apr. 24, 2016, Annex 2.
Kaminsky. Expert Report of Dr. Ronald Kaminsky dated Apr. 24, 2016.
Kararli. "Comparison of the Gastrointestinal Anatomy, Physiology, and Biochemistry of Humans and Commonly Used Laboratory Animals" Biopharmaceutics and Drug Disposition, 1995, 16:351-380.
Kilp, et al. "Pharmacokinetics of fluralaner in dogs following a single oral or intravenous administration" Parasites & Vectors, 2014, 7:85-89.
Kramer, et al. "Flea Biology and Control; The Biology of the Cat Flea Control and Prevention with Imidacloprid in Small Animals" Springer, 2001.
Lahm, et al. "4-Azolyiphenyl isoxazoline insecticides acting at the GABA gated chloride channel" Bioorganic and Medicinal Chemistry Letters, 2013, 23:3001-3006.
Letter with submission of Declarations in reply to Opposition by Intervet International B.V. Australian Patent Application No. 2008268321 dated May 11, 2015.
Letter with submission of Declarations in reply to Opposition by Intervet International B.V. Australian Patent Application No. 2008268321 dated Oct. 14, 2015.
Macquarie Dictionary (2nd Edition)—Definition of "Parenteral".
Marchiondo "Pyrantel Parasiticide Therapy in Humans and Domestic Animals" Edited by Alan A. Marchiondo, Academic Press, 2016.
Marchiondo, et al. "World Association for the Advancement of Veterinary Parasitology (W.A.A.V.P.) guidelines for evaluating the efficacy of parasiticides for the treatment, prevention and control of flea and tick infestation on dogs and cats" Veterinary Parasitology, 2007, 145:332-344. (Document D12).
Meegalla, et al. "Synthesis and Insecticidal Activity of Fluorinated 2-(2,6-Dichloro-4-Trifluoromethylphenyl)-2,4,5,6-Tetrahydrocyclopentapyrazoles" Bioorganic and Medicinal Chemistry Letters, 2006, 16:1702-1706.
Mehlhorn, et al. "Comparative study on the effects of three insecticides (fipronil, imidacloprid, selamectin) on developmental stages of the cat flea (*Ctenocephalides felis* Bouche 1835): a light and

(56) References Cited

OTHER PUBLICATIONS electron microscopic analysis of in vivo and in vitro experiments" Parasitol Res., 2001, 87:198-207.
Meinke. "Perspectives in Animal Health: Old Targets and New Opportunities" Journal of Medicinal Chemistry, Mar. 2001, 44(5):641-659.
Miller, et al. "A Field Study to evaluate Integrated Flea Control using Lufenuron and Nitenpyram compared to Imidacloprid used alone" Aust. Vet. Practit., Jun. 2001, 31(2):60-66.
Mullins. "Imidacloprid—A New Nitroguanidine Insecticide" Duke et al.; Pest Control with Enhanced Environmental Safety ACS Symposium Series; American Chemical Society, Washington, D.C. 1993.
Newhouse, et al. "Racemic and chiral lactams as potent, selective and functionally active CCR4 antagonists" Bioorganic and Medicinal Chemistry Letters, 2004, 14:5537-5542.
Nissan Chemical Ind., Ltd. Response to Submissions dated Jan. 31, 2017 in Opposition to EP Patent No. 2 182 945 (EP Application No. 08 7771 978.7).
Nissan Chemical Ind., Ltd. Supplemental Submissions by Opponent dated Apr. 7, 2017 in Opposition to EP Patent No. 2 182 945 (EP Application No. 08 7771 978.7).
Ostlind, et al. "A Novel Cimex Lectularius—Rodent Assay for the Detection of Systemic Ectoparasiticide Activity" Southwestern Entomologist, Sep. 2001, 26(3):181-186.
Riviere, et al. "Veterinary Pharmacology & Therapeutics" 9th Edition, 2009, pp. 1056-1065; 1122-1131.
Rugg. "Ivermectin & The Macrocyclic Lactones Salvation or Curse?" College of Veterinary Medicine at Washington State University.
Russell, et al. "The Principles of Humane Experimental Technique" Methuen & Co. Ltd., 1959.
Russian Federation Notice of Opposition dated Nov. 26, 2014 opposing Russian Federation patent No. 2508102, Opponent: Intervet International B.V.
Russian Federation Opposition Decision dated Dec. 29, 2016 for Russian Federation Patent No. 2508102.
Rust. "Advances in the control of *Ctenocephalides felis* (cat flea) on cats and dogs" Trends in Parasitology, May 2005, 21(5):232-236.
Santora, et al. "Development of a mouse model to determine the systemic activity of potential flea-control compounds" Veterinary Parasitology, 2002, 104:257-264.
Sarasola, et al. "Pharmacokinetics of selamectin following intravenous, oral and topical administration in cats and dogs" J. vet. Pharmacol. Therap., 2002, 25:265-272.
Schenker, et al. "Comparative speed of kill between nitenpyram, fipronil, imidacloprid, selamectin and cythioate against adult *Ctenocephalides felis* (Bouche) on cats and dogs" Veterinary Parasitology, 2003, 112:249-254.
Series of Tables Outlining Flea Treatments for Cats and Dogs that were available in 2007 (Exhibit PJL-2 of Penelope-Jane Linnett Statutory Declaration dated May 11, 2015).
Shoop, et al. "Systemic Efficacy of Nodulisporamides against Fleas on Dogs" The Journal of Parasitology, Oct. 2001, 87(5):1150-1154. (Document D13).
Smith, et al. "Pharmacokinetics and Metabolism in Drug Design" 2nd Edition, vol. 31, Chapter 2, Pharmacokinetics, p. 25, 2006.
Snyder, et al. "Preliminary studies on the effectiveness of the novel pulicide, spinosad, for the treatment and control of fleas on dogs" Veterinary Parasitology, 2007, 150:345-351. (Document D18).
Statutory Declaration of Bryce Alan Peters dated May 11, 2015.
Statutory Declaration of Bryce Alan Peters dated Oct. 14, 2015.
Statutory Declaration of Dr. Alan Marchiondo dated Dec. 17, 2016.
Statutory Declaration of Dr. Heike Williams dated Apr. 13, 2017.
Statutory Declaration of Dr. Heike Williams dated Apr. 20, 2016.
Statutory Declaration of Dr. Jeffrey N. Clark dated Dec. 16, 2016.
Statutory Declaration of Dr. Penelope-Jane Linnett dated May 11, 2015.
Statutory Declaration of Dr. Penelope-Jane Linnett dated Oct. 14, 2015.
Statutory Declaration of Dr. Peter Alexander Taylor dated Aug. 11, 2015.
Statutory Declaration of Dr. Ronald Kaminsky dated Jun. 13, 2016.
Statutory Declaration of Dr. Ronald Kaminsky dated Oct. 13, 2015.
Statutory Declaration of Dr. Steven Rodney Koop dated Apr. 28, 2016.
Statutory Declaration of Petr Fisara dated May 11, 2015.
Statutory Declaration of Petr Fisara dated Sep. 25, 2015.
Sutra, et al. "Determination of selamectin in dog plasma by high performance liquid chromatography with automated solid phase extraction and fluorescence detection" Vet. Res., 2001, 32:455-461.
Table of Active Agents that were available between 1995 and 2007, identifying whether there had been any adverse experience reports, or any reports of resistance (Exhibit PJL-2 of Penelope-Jane Linnett Statutory Declaration dated May 11, 2015).
Table showing Chemical Structures of Compounds (Exhibit BAP-19 of Bryce Alan Peters Statutory Declaration dated Oct. 14, 2015).
Taylor. "Recent Developments in Ectoparasiticides" The Veterinary Journal, 2001, 161:253-268.
U.S. Appl. No. 60/937,389 filed Jun. 27, 2007.
U.S. Appl. No. 60/956,448 filed Aug. 17, 2007.
Wagner, et al. "Field Efficacy of Moxidectin in Dogs and Rabbits Naturally Infested With Sarcoptes Spp., Demodex Spp. And Psoroptes Spp. Mites" Veterinary Parasitology, 2000, 93:149-158.
Witchey-Lakshmanan, et al. "Chapter 9: Controlled Drug Delivery and the Companion Animal" in Controlled Release Veterinary Drug Delivery: Biological and Pharmaceutical Considerations, Edited by M.J. Rathbone and R. Gumy, Elsevier Science B.V., 2000.
Wong, et al. "Enhancement of the dissolution rate and oral absorption of a poorly water soluble drug by formation of surfactant-containing microparticles" International Journal of Pharmaceutics, 2006. 317:61-68.
Woods, et al. "The challenges of developing novel antiparasitic drugs" Invert Neurosci, 2007, 7:245-250.
Zakson-Aiken, et al. "Systemic Activity of the Avermectins Against the Cat Flea (Siphonaptera: Pulicidae)" Journal of Medical Entomology, 2001, 38(4):576-580.
Request for Interview filed Oct. 16, 2017, submitted during prosecution of U.S. Appl. No. 15/097,002, including Exhibits 1: Santora, et al. "Development of a mouse model to determine the systemic activity of potential flea-control compounds" Veterinary Parasitology, 2002, 104:257-264 and Exhibit 2: Structure of Compounds Disclosed in Test E of Du Pont's WO 2007/079162 (p. 111) and Fluralaner.
Request for Interview filed Oct. 16, 2017, submitted during prosecution of U.S. Appl. No. 15/097,002, including Exhibits 3: Ahmed, et al. "Pharmaceutical challenges in veterinary product development" Advanced Drug Delivery Reviews, 2002, 54:871-882 and Exhibit 4: Shoop, et al. "Systemic Efficacy of Nodulisporamides Against Fleas on Dogs" Journal of Parasitology, 2001, 87(5):1150-1154.
Declaration of Alan A. Marchiondo dated Oct. 7, 2017 filed in Russian Intellectual Property Court, Case No. SIP-164/2017.
English translation of Written Pleadings filed on Nov. 9, 2017 by Intervet International B.V. in Russian Intellectual Propery Court, Case No. SIP-164/2017.
Notice of Contention filed by Intervet International B.V. dated Aug. 14, 2017 in the Federal Court of Australia, Case No. VID795 of 2017.
Statement of Grounds and Particulars filed by Intervet International B.V. dated Sep. 29, 2017 in the Federal Court of Australia, Case No. VID795 of 2017.
Appellant's Response to Statements and Grounds & Particulars of Opposition filed by E.I. DuPont de Nemours and Company in the Federal Court of Australia, Case No. VID795 of 2017.
Mita—Examiner Interview Summary dated Nov. 29, 2017, p. 1-4.
Exhibit A—Record of Interview filed Sep. 11, 2017 in U.S. Appl. No. 15/207,999.
Exhibit B—Suggestion of Interference between U.S. Appllication by Heckeroth, et al. and US Application by Lahm, et al., filed Dec. 12, 2014 in U.S. Appl. No. 12/673,722.
Exhibit C—Intervet Letter to EPO dated May 28, 2010 in EP Application No. 08803041.6.

(56) References Cited

OTHER PUBLICATIONS

Exhibit D—Decision on Rehearing—Bd.R. 127(d) (PTAB, May 18, 2015.
English translation of Written Pleadings filed on Dec. 1, 2017 by Intervet International B.V. in Russian Intellectual Property Court, Case No. SIP-164/2017.
Publication of Decision issued Dec. 12, 2017 in Russian Intellectual Property Court, Case No. SIP-164/2017, published on Dec. 19, 2017.
English machine translation of Publication of Decision dated Dec. 12, 2017 in Russian Intellectual Property Court, Case No. SIP-164/2017, published on Dec. 19, 2017.
Ahmed, et al. "Pharmaceutical challenges in veterinary product development" Advanced Drug Delivery Review, 2002, 54:871-882.
Australian Notice of Appeal dated Jul. 20, 2017; E.I. DuPont De Nemours and Company v. Intervet International B.V. filed in Federal Court of Australia re: Australian Application No. 2008268321.
Australian Notice of Opposition dated Nov. 12, 2014, opposing Australian Patent Application No. 2008268321; Opponent: Intervet International B.V.
Australian Opposition Decision dated Jun. 29, 2017 for Australian Application No. 2008268321.
Bayer DVM. Product information advantus (imidacloprid) soft chew, Mar. 2017.
Benet, et al. "Drug Absorption, Distribution and Elimination" Chapter 17 in Burger's Medicinal Chemistry and Drug Discovery, 2003.
Bishop, et al. "Selamectin: a novel broad-spectrum endectocide for dogs and cats" Veterinary Parasitology, 2000, 91:163-176.
Campbell. "Invermectin, An Antiparasitic Agent" Medicinal Research Reviews, 1993, 13(1):61-79.
Daron, et al. "Daptomycin or teicoplanin in combination with gentamicin for treatment of experimental endocarditis due to a highly glycopeptide-resistant isolate of Enterococcus faecium" Antimicrobial Agents and Chemotherapy, Dec. 1992, 36(12):2611-2616.
Chatellier. "Pharam Profile—Nitenpyram" Compendium, Aug. 2001.
Choi, et al. "In-vitro and in-vivo activities of DW-116, a new fluoroquinolone" Journal of Antimicrobial Chemotherapy, 1997, 39:509-514.
Clements, et al. "Antibiotic Activity and Characterization of BB-3497, a Novel Peptide Deformylase Inhibitor" Antimicrobial Agents and Chemotherapy, Feb. 2001, 45(2):563-570.
Coop, et al. "Ectoparasites: recent advances in control" Trends in Parasitology, Feb. 2002, 18(2):55-56.
Curriculum Vitae of Bryce Alan Peters Jun. 2014.
Curriculum Vitae of Dr. Alan Anton Marchiondo, May 2016.
Curriculum Vitae of Dr. Jeffrey N. Clark, Jan. 2016.
Curriculum Vitae of Dr. Penelope-Jane Linnett, Nov. 2015.
Curriculum Vitae of Dr. Peter Alexander Taylor, Nov. 2014.
Curriculum Vitae of Dr. Steven Rodney Koop.
Curriculum Vitae of Petr Fisara, May 2015.
Curriculum Vitae of Ronald Kaminsky, Jan. 2015.
Denholm, et al. "Large-scale Monitoring of Insecticide Susceptibility in Cat Fleas, *Ctenocephalides felis*" Outlook on Pest Management, Jun. 2015, pp. 109-112.
Bryden, et al. "The cat flea: biology, ecology and control" Veterinary Parasitology, 1994, 52:1-19.
Dryden. "The Problem with Fleas: Managing Persistent Flea Infestations", Western Veterinary Conference, 2013.
Dupuy, et al. "Pharmacokinetics of Selamectin in Dogs after Topical Application" Veterinary Research Communications, 2004, 28:407-413.
E.I. Du Pont De Nemours and Company. "Regulation 5.23 Appendices I-XI" filed by DuPont on Apr. 22, 2016.

E.I. Du Pont De Nemours and Company. Applicant's Outline of Submissions filed May 3, 2017, in Opposition of Australian Application No. 2008268321.
E.I. Du Pont De Nemours and Company. Reply to Summons to Attend Oral Proceedings filed Jan. 9, 2015 in European Application No. 08771978.7.
E.I. Du Pont De Nemours and Company. Response to Opposition against Russian Federation Patent No. 2508102, Sep. 2016.
EPA. United States Environmental Protection Agency Memorandum relating to proposed registration of Cyphenothrin on Domestic Pets Mar. 2006.
European Examination Report dated Jan. 24, 2012, which issued during prosecution of European Application Number 08 803 041.6.
European Examination Report dated Mar. 25, 2011, which issued during prosecution of European Application Number 08 803 041.6.
European Medicines Agency. "Committee for Medicinal Products for Veterinary Use (CBMP) Assessment report for Bravecto" Dec. 2013.
European Notice of Opposition dated Aug. 6, 2015, opposing EP Patent No. 2 182 945 (EP Application No. 08 7771 978.7); Opponent: Nissan Chemical Ind., Ltd.
European Notice of Opposition dated May 3, 2016, opposing European Patent No. 2 182 945 (EP Application No. 08 7771 978.7); Opponent: Virbac.
European Notice of Opposition dated May 4, 2016, opposing European Patent No. 2 182 945 (EP Application No. 08 7771 978.7); Opponent: Intervet International B.V.
Farmers Weekly. Sep. 2007, vol. 5, No. 35.
FDA. "NADA 132-337 Proban 90 mg tablets—supplemental approval" Apr. 25, 1994.
Fessey, et al. "The Role of Plasma Protein Binding in Drug Discovery" Pharmacokinetic Profiling in Drug Research, 2006.
Freter. "Drug Discovery—Today and Tomorrow: The Role of Medicinal Chemistry" Pharmaceutical Research, 1988 5(7):397-400.
Geary, et al. "Frontiers in Anthelmintic Pharmacology" Veterinary Parasitology, 1999, 84:275-295.
Guerrero. "Canine Flea and Tick Control, A Reference Guide to EPA-Approved Spot on Products" Technical Monograph, 2009.
Harkins, et al. "Absence of detectable pharmacological effects after oral administration of isoxsuprine" Equine Veterinary Journal, 1998, 30(4);294-299.
Hecker, et al. Discovery of MC-02,331, a New Cephalosporin Exhibiting Potent Activity Against Methicillin-.
Holm. "Efficacy of milbemycin oxime in the treatment of canine generalized demodicosis: a retrospective study of 99 dogs (1995-2000)" Veterinary Dermatology, 2003, 14:189-195.
Hovda. et al. "Toxicology of newer pesticides for use in dogs and cats" The Veterinary Clinics, Small Animal Practice, 2002, 32:455-467.
Jeffrey N. Clark, et al., Chapter 8, Whole-Organism Screens for Ectoparasites. Ectoparasites: Drug Discovery Against Moving Targets, First Edition. Edited by Charles Q. Meng and Ann E. Sluder (2018) p. 167-184.
Jeffrey N. Clark, Chapter 11, Testing in Target Hosts for Ectoparasiticide Discovery and Development. Ectoparasites: Drug Discovery Against Moving Targets, First Edition. Edited by Charles Q. Meng and Ann E. Sluder (2018) p. 223-241.
Annex I: Summary of Product Characteristics for Bravecto cited in Declaration of Dr. Jeffrey N. Clark on Dec. 16, 2016, in Opposition Proceeds of EP 218945B.
Safety of Fipronil in Dogs and Cats: A review of literature: Conducted on behalf of the Australian Pesticides and Veterinary Medicines Authority (APVMA) cited in the Declaration of Dr. Jeffrey N. Clark on Dec. 16, 2016, in Opposition Proceeds of EP 218945B.

* cited by examiner

ANIMAL PEST CONTROL METHOD

FIELD OF THE INVENTION

This invention relates to a method for protecting an animal from a parasitic pest and parasitic pest infestation.

BACKGROUND OF THE INVENTION

The control of animal parasites in animal health is essential, especially in the areas of food production and companion animals. Existing methods of treatment and parasite control are being compromised due to growing resistance to many current commercial parasiticides. The discovery of more effective ways to control animal parasites is therefore imperative. In addition, it is advantageous to discover ways to apply pesticides to animals orally or parenterally so as to prevent the possible contamination of humans or the surrounding environment.

PCT Patent Publication WO 05/085216 discloses isoxazoline derivatives of Formula i as insecticides

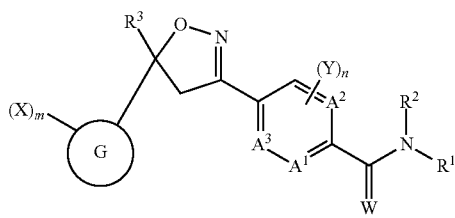

i wherein, inter alia, each of $A^1$, $A^2$ and $A^3$ are independently C or N; G is a benzene ring; W is O or S; and X is halogen or $C_1$-$C_6$ haloalkyl.

The method of the present invention is not disclosed in this publication.

SUMMARY OF THE INVENTION

This invention pertains to a method for protecting animals from a parasitic invertebrate pest comprising orally or parenterally administering to the animal a pesticidally effective amount of a compound of Formula 1 (including all geometric and steroisomers), an N-oxide or a salt thereof

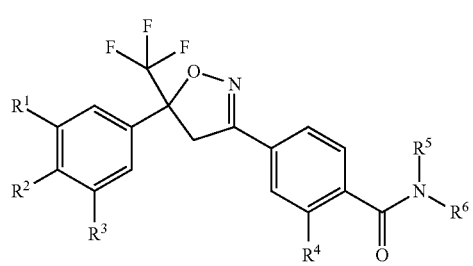

1 wherein
$R^1$ is halogen, $C_1$-$C_3$ haloalkyl or $C_1$-$C_3$ haloalkoxy;
$R^2$ is H, halogen, $C_1$-$C_3$ alkyl, $C_1$-$C_3$ haloalkyl or cyano;
$R^3$ is H, halogen, $C_1$-$C_3$ haloalkyl or $C_1$-$C_3$ haloalkoxy;
$R^4$ is halogen, $C_1$-$C_3$ alkyl, $C_1$-$C_3$ haloalkyl or $C_1$-$C_3$ haloalkoxy;
$R^5$ is H, $CH_3$, $C_2$-$C_4$ alkylcarbonyl, $C_2$-$C_4$ haloalkylcarbonyl, $C_2$-$C_5$ alkoxycarbonyl or $CH_2O(C_1$-$C_3$ alkyl);
$R^6$ is $C_1$-$C_6$ alkyl, $C_1$-$C_6$ haloalkyl, $C_3$-$C_6$ cycloalkyl or $C_3$-$C_6$ halocycloalkyl, each group substituted with one $R^7$; or $R^6$ is $(CH_2)_mQ$;
Q is a 4- to 6-membered saturated ring containing carbon atoms and one O or $S(O)_n$ as ring members and optionally substituted with 1 or 2 $R^{8a}$ and one $R^{8b}$;
$R^7$ is $OR^9$, $S(O)_nR^{10}$ or $C(O)NR^{11}R^{12}$; or $R^7$ is pyridine or thiazole, each optionally substituted with 1 or 2 $R^{15}$;
each $R^{8a}$ is independently halogen, cyano or $C_1$-$C_2$ alkyl;
$R^{8b}$ is $OR^9$, $S(O)_nR^{10}$ or $C(O)NR^{11}R^{12}$;
$R^9$ is H, CHO, $C_2$-$C_4$ alkylcarbonyl, $C_2$-$C_4$ haloalkylcarbonyl or $C_2$-$C_5$ alkoxycarbonyl; or $R^9$ is $C_1$-$C_4$ alkyl or $C_1$-$C_4$ haloalkyl, each optionally substituted with one $R^{13}$; or $R^9$ is pyridine or thiazole, each optionally substituted with 1 or 2 $R^{15}$;
$R^{10}$ is $C_1$-$C_4$ alkyl or $C_1$-$C_4$ haloalkyl, each optionally substituted with one $R^{13}$; or $R^{10}$ is pyridine or thiazole, each optionally substituted with 1 or 2 $R^{15}$;
$R^{11}$ is H, CHO, $C_1$-$C_4$ alkyl, $C_1$-$C_4$ haloalkyl, $CH_2O(C_1$-$C_3$ alkyl), $C_2$-$C_4$ alkylcarbonyl, $C_2$-$C_4$ haloalkylcarbonyl or $C_2$-$C_5$ alkoxycarbonyl;
$R^{12}$ is $C_1$-$C_4$ alkyl, $C_1$-$C_4$ haloalkyl or $C_3$-$C_6$ cycloalkyl, each optionally substituted with one $R^{13}$; or $R^{12}$ is H, $C_3$-$C_6$ alkenyl, $C_3$-$C_6$ haloalkenyl, $C_3$-$C_6$ alkynyl or $OR^{14}$;
$R^{13}$ is cyano, $C_3$-$C_6$ cycloalkyl, $C_3$-$C_6$ halocycloalkyl, OH, $OR^{14}$ or $S(O)_nR^{16}$; or $R^{13}$ is pyridine or thiazole, each optionally substituted with 1 or 2 $R^{15}$;
$R^{14}$ is $C_1$-$C_4$ alkyl or $C_1$-$C_4$ haloalkyl;
each $R^{15}$ is independently halogen, cyano, $C_1$-$C_3$ alkyl, $C_1$-$C_3$ haloalkyl or $C_1$-$C_3$ haloalkoxy;
$R^{16}$ is $C_1$-$C_4$ alkyl or $C_1$-$C_4$ haloalkyl;
m is 0 or 1; and
n is 0, 1 or 2.

This invention also relates to such method wherein the parasitic invertebrate pest or its environment is contacted with a composition comprising a biologically effective amount of a compound of Formula 1, an N-oxide or a salt thereof, and at least one additional component selected from the group consisting of surfactants, solid diluents and liquid diluents, said composition optionally further comprising a biologically effective amount of at least one additional biologically active compound or agent.

This invention further provides a method for treating, preventing, inhibiting and/or killing ecto- and/or endoparasites comprising administering to and/or on the animal a pesticidally effective amount of a compound of Formula 1, an N-oxide or a salt thereof, (e.g., as a composition described herein). This invention also relates to such method wherein a pesticidally effective amount of a compound of Formula 1, an N-oxide or a salt thereof, (e.g., as a composition described herein) is administered to the environment (e.g., a stall or blanket) in which an animal resides.

DETAILS OF THE INVENTION

As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but may include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

As referred to in this disclosure, the terms "pest", "invertebrate pest" and "parasitic invertebrate pest" include arthropods, gastropods and nematodes of economic importance as pests. The term "arthropod" includes insects, mites, spiders, scorpions, centipedes, millipedes, pill bugs and symphylans. The term "gastropod" includes snails, slugs and other Stylommatophora. The term "nematode" includes all of the helminths, such as roundworms, heartworms, and phytophagous nematodes (Nematoda), flukes (Tematoda), Acanthocephala, and tapeworms (Cestoda).

In the context of this disclosure "invertebrate pest control" means inhibition of invertebrate pest development (including mortality, feeding reduction, and/or mating disruption), and related expressions are defined analogously. The terms "pesticidal" and "pesticidally" refer to observable effects on a pest to provide protection of an animal from the pest. Pesticidal effects typically relate to diminishing the occurrence or activity of the target parasitic invertebrate pest. Such effects on the pest include necrosis, death, retarded growth, diminished mobility or lessened ability to remain on or in the host animal, reduced feeding and inhibition of reproduction. These effects on parasitic invertebrate pests provide control (including prevention, reduction or elimination) of parasitic infestation or infection of the animal.

A parasite "infestation" refers to the presence of parasites in numbers that pose a risk to humans or animals. The infestation can be in the environment (e.g., in human or animal housing, bedding, and surrounding property or structures), on agricultural crops or other types of plants, or on the skin or fur of an animal. When the infestation is within an animal (e.g., in the blood or other internal tissues), the term infestation is also intended to be synonymous with the term "infection" as that term is generally understood in the art, unless otherwise stated.

In the above recitations, the term "alkyl", used either alone or in compound words such as "haloalkyl" includes straight-chain or branched alkyls, such as methyl, ethyl, n-propyl, i-propyl, or the different butyl, pentyl or hexyl isomers. "Alkenyl" includes straight-chain or branched alkenes such as ethenyl, 1-propenyl, 2-propenyl, and the different butenyl, pentenyl and hexenyl isomers. "Alkenyl" also includes polyenes such as 1,2-propadienyl and 2,4-hexadienyl. "Alkynyl" includes straight-chain or branched alkynes such as ethynyl, 1-propynyl, 2-propynyl and the different butynyl, pentynyl and hexynyl isomers. "Alkynyl" can also include moieties comprised of multiple triple bonds such as 2,5-hexadiynyl.

"Cycloalkyl" includes, for example, cyclopropyl, cyclobutyl, cyclopentyl and cyclohexyl. The term "cyclopropylmethyl" denotes cyclopropyl substitution on a methyl moiety.

The term "halogen", either alone or in compound words such as "haloalkyl", or when used in descriptions such as "alkyl substituted with halogen" includes fluorine, chlorine, bromine or iodine. Further, when used in compound words such as "haloalkyl", or when used in descriptions such as "alkyl substituted with halogen" said alkyl may be partially or fully substituted with halogen atoms which may be the same or different. Examples of "haloalkyl" or "alkyl substituted with halogen" include $CF_3$, $CH_2Cl$, $CH_2CF_3$ and $CCl_2CF_3$. The terms "halocycloalkyl", "haloalkoxy", "haloalkenyl", and the like, are defined analogously to the term "haloalkyl". Examples of "haloalkoxy" include $OCF_3$, $OCH_2CCl_3$, $OCH_2CH_2CHF_2$ and $OCH_2CF_3$. Examples of "haloalkenyl" include $CH_2CH=C(Cl)_2$ and $CH_2CH=CHCH_2CF_3$.

"Alkylcarbonyl" denotes a straight-chain or branched alkyl moiety bonded to a C(O) moiety. The chemical abbreviation C(O) as used herein represents a carbonyl moiety. Examples of "alkylcarbonyl" include $C(O)CH_3$, $C(O)CH_2CH_2CH_3$ and $C(O)CH(CH_3)_2$.

The total number of carbon atoms in a substituent group is indicated by the "$C_i$-$C_j$" prefix where i and j are numbers from 1 to 6. For example, $C_1$-$C_3$ alkyl designates methyl through propyl.

When a group contains a substituent which can be hydrogen, for example $R^5$ or $R^{11}$, then when this substituent is taken as hydrogen, it is recognized that this is equivalent to said group being unsubstituted.

The term "ring member", as used in the definition of the substituent Q in the Summary of the Invention, refers to an atom or other moiety (e.g., O or $S(O)_n$) forming the backbone of a ring. Examples of Q include

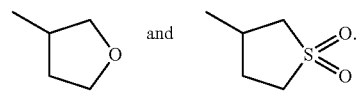

Compounds of Formula 1 can exist as one or more stereoisomers. The various stereoisomers include enantiomers, diastereomers and atropisomers. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate, enrich, and/or to selectively prepare said stereoisomers. The compounds Formula 1 may be present as a mixture of stereoisomers, individual stereoisomers or as an optically active form. For example, two possible enantiomers of Formula 1 are depicted as Formula 1a and Formula 1b involving the isoxazoline chiral center identified with an asterisk (*). Analogously, other chiral centers are possible at, for example, $R^1$, $R^6$, $R^9$ and $R^{11}$.

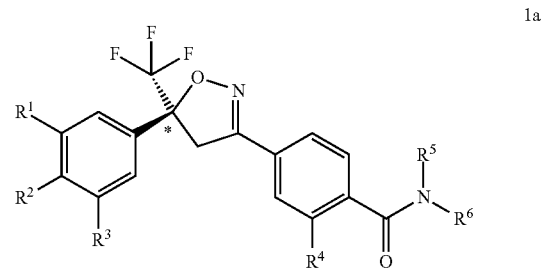

1a

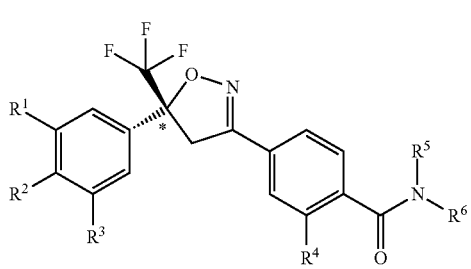

Molecular depictions drawn herein follow standard conventions for depicting stereochemistry. To indicate stereoconfiguration, bonds rising from the plane of the drawing and towards the viewer are denoted by solid wedges wherein the broad end of the wedge is attached to the atom rising from the plane of the drawing towards the viewer. Bonds going below the plane of the drawing and away from the viewer are denoted by dashed wedges wherein the narrow end of the wedge is attached to the atom further away from the viewer. Constant width lines indicate bonds with a direction opposite or neutral relative to bonds shown with solid or dashed wedges; constant width lines also depict bonds in molecules or parts of molecules in which no particular stereoconfiguration is intended to be specified.

The more biologically active enantiomer is believed to be Formula 1a. Formula 1a has the (S) configuration at the chiral carbon, and Formula 1b has the (R) configuration at the chiral carbon.

The method of this invention comprises racemic mixtures, for example, equal amounts of the enantiomers of Formulae 1a and 1b. In addition, the method of this invention includes compounds that are enriched compared to the racemic mixture in an enantiomer of Formula 1. Also included are the essentially pure enantiomers of compounds of Formula 1, for example, Formula 1a and Formula 1b.

When enantiomerically enriched, one enantiomer is present in greater amounts than the other, and the extent of enrichment can be defined by an expression of enantiomeric excess ("ee"), which is defined as $(2x-1) \cdot 100\%$, where x is the mole fraction of the dominant enantiomer in the mixture (e.g., an ee of 20% corresponds to a 60:40 ratio of enantiomers).

Preferably the compositions of Formula 1 have at least a 50% enantiomeric excess; more preferably at least a 75% enantiomeric excess; still more preferably at least a 90% enantiomeric excess; and the most preferably at least a 94% enantiomeric excess of the more active isomer. Of particular note are enantiomerically pure embodiments of the more active isomer.

Compounds of Formula 1 can comprise additional chiral centers. The method of this invention comprises racemic mixtures as well as enriched and essentially pure stereoconfigurations at these additional chiral centers. Compounds of Formula 1 can exist as one or more conformational isomers due to restricted rotation about the amide bond in Formula 1. The method of this invention comprises mixtures of conformational isomers. In addition, the method of this invention includes compounds that are enriched in one conformer relative to others.

Embodiments of the present invention as described in the Summary of the Invention include those described below. In the following Embodiments, reference to "a compound of Formula 1" includes the definitions of substituents specified in the Summary of the Invention unless further defined in the Embodiments.

Embodiment 1. The method described in the Summary of the Invention wherein the pesticidally effective compound is selected from an isoxazoline of Formula 1 (including all geometric and steroisomers), an N-oxide or a salt thereof

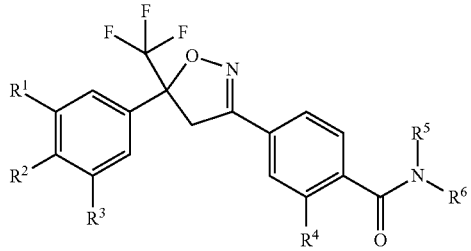

wherein
$R^1$ is halogen, $C_1$-$C_3$ haloalkyl or $C_1$-$C_3$ haloalkoxy;
$R^2$ is H, halogen, $C_1$-$C_3$ alkyl, $C_1$-$C_3$ haloalkyl or cyano;
$R^3$ is H, halogen, $C_1$-$C_3$ haloalkyl or $C_1$-$C_3$ haloalkoxy;
$R^4$ is halogen, $C_1$-$C_3$ alkyl, $C_1$-$C_3$ haloalkyl or $C_1$-$C_3$ haloalkoxy;
$R^5$ is H, $CH_3$, $C_2$-$C_4$ alkylcarbonyl, $C_2$-$C_4$ haloalkylcarbonyl, $C_2$-$C_5$ alkoxycarbonyl or $CH_2O(C_1$-$C_3$ alkyl);
$R^6$ is $C_1$-$C_6$ alkyl, $C_1$-$C_6$ haloalkyl, $C_3$-$C_6$ cycloalkyl or $C_3$-$C_6$ halocycloalkyl, each group substituted with one $R^7$; or $R^6$ is $(CH_2)_mQ$;
Q is a 4- to 6-membered saturated ring containing carbon atoms and one O or $S(O)_n$ as ring members and optionally substituted with 1 or 2 $R^{8a}$ and one $R^{8b}$;
$R^7$ is $OR^9$, $S(O)_nR^{10}$ or $C(O)NR^{11}R^{12}$; or $R^7$ is pyridine or thiazole, each optionally substituted with 1 or 2 $R^{15}$;
each $R^{8a}$ is independently halogen, cyano or $C_1$-$C_2$ alkyl;
$R^{8b}$ is $OR^9$, $S(O)_nR^{10}$ or $C(O)NR^{11}R^{12}$;
$R^9$ is H, CHO, $C_2$-$C_4$ alkylcarbonyl, $C_2$-$C_4$ haloalkylcarbonyl or $C_2$-$C_5$ alkoxycarbonyl; or $R^9$ is $C_1$-$C_4$ alkyl or $C_1$-$C_4$ haloalkyl, each optionally substituted with one $R^{13}$; or $R^9$ is pyridine or thiazole, each optionally substituted with 1 or 2 $R^{15}$;
$R^{10}$ is $C_1$-$C_4$ alkyl or $C_1$-$C_4$ haloalkyl, each optionally substituted with one $R^{13}$; or $R^{10}$ is pyridine or thiazole, each optionally substituted with 1 or 2 $R^{15}$;
$R^{11}$ is H, CHO, $C_1$-$C_4$ alkyl, $C_1$-$C_4$ haloalkyl, $CH_2O(C_1$-$C_3$ alkyl), $C_2$-$C_4$ alkylcarbonyl, $C_2$-$C_4$ haloalkylcarbonyl or $C_2$-$C_5$ alkoxycarbonyl;
$R^{12}$ is $C_1$-$C_4$ alkyl, $C_1$-$C_4$ haloalkyl or $C_3$-$C_6$ cycloalkyl, each optionally substituted with one $R^{13}$; or $R^{12}$ is H, $C_3$-$C_6$ alkenyl, $C_3$-$C_6$ haloalkenyl, $C_3$-$C_6$ alkynyl or $OR^{14}$;
$R^{13}$ is cyano, $C_3$-$C_6$ cycloalkyl, $C_3$-$C_6$ halocycloalkyl, OH, $OR^{14}$ or $S(O)_nR^{16}$; or $R^{13}$ is pyridine or thiazole, each optionally substituted with 1 or 2 $R^{15}$;
$R^{14}$ is $C_1$-$C_4$ alkyl or $C_1$-$C_4$ haloalkyl;
each $R^{15}$ is independently halogen, cyano, $C_1$-$C_3$ alkyl, $C_1$-$C_3$ haloalkyl or $C_1$-$C_3$ haloalkoxy;
$R^{16}$ is $C_1$-$C_4$ alkyl or $C_1$-$C_4$ haloalkyl;
m is 0 or 1; and
n is 0, 1 or 2.
Embodiment 2. The method of Embodiment 1 wherein $R^1$ is Cl, Br, $CF_3$, $OCF_3$ or $OCH_2CF_3$.
Embodiment 3. The method of Embodiment 2 wherein $R^1$ is Cl, Br or $CF_3$.

Embodiment 4. The method of Embodiment 3 wherein $R^1$ is Cl.
Embodiment 5. The method of Embodiment 3 wherein $R^1$ is Br.
Embodiment 6. The method of Embodiment 3 wherein $R^1$ is $CF_3$.
Embodiment 7. The method of Embodiment 1 wherein $R^2$ is H, F or Cl.
Embodiment 8. The method of Embodiment 7 wherein $R^2$ is H.
Embodiment 9. The method of Embodiment 7 wherein $R^2$ is F.
Embodiment 10. The method of Embodiment 7 wherein $R^2$ is Cl.
Embodiment 11. The method of Embodiment 1 wherein $R^3$ is H, F, Cl, Br or $CF_3$.
Embodiment 12. The method of Embodiment 11 wherein $R^3$ is H, Cl, Br or $CF_3$.
Embodiment 13. The method of Embodiment 12 wherein $R^3$ is Cl, Br or $CF_3$.
Embodiment 14. The method of Embodiment 11 wherein $R^3$ is H.
Embodiment 15. The method of Embodiment 11 wherein $R^3$ is Cl.
Embodiment 16. The method of Embodiment 11 wherein $R^3$ is Br.
Embodiment 17. The method of Embodiment 11 wherein $R^3$ is $CF_3$.
Embodiment 18. The method of Embodiment 1 wherein $R^4$ is halogen or $C_1$-$C_3$ alkyl.
Embodiment 19. The method of Embodiment 18 wherein $R^4$ is halogen or methyl.
Embodiment 20. The method of Embodiment 19 wherein $R^4$ is halogen.
Embodiment 21. The method of Embodiment 20 wherein $R^4$ is Cl.
Embodiment 22. The method of Embodiment 19 wherein $R^4$ is methyl.
Embodiment 23. The method of Embodiment 1 wherein $R^5$ is H.
Embodiment 24. The method of Embodiment 1 wherein $R^6$ is halogen or $C_1$-$C_6$ alkyl.
Embodiment 25. The method of Embodiment 1 wherein $R^6$ is $C_1$-$C_6$ alkyl substituted with one $R^7$;
Embodiment 26. The method of Embodiment 1 wherein $R^7$ is $OR^9$, $S(O)_nR^{10}$ or $C(O)NR^{11}R^{12}$.
Embodiment 27. The method of Embodiment 26 wherein $R^7$ is $OR^9$.
Embodiment 28. The method of Embodiment 26 wherein $R^7$ is $S(O)_nR^{10}$.
Embodiment 29. The method of Embodiment 26 wherein $R^7$ is $C(O)NR^{11}R^{12}$.
Embodiment 30. The method of Embodiment 1 wherein $R^9$ is H or $C_1$-$C_4$ alkyl.
Embodiment 31. The method of Embodiment 30 wherein $R^9$ is H or methyl.
Embodiment 32. The method of Embodiment 31 wherein $R^9$ is H.
Embodiment 33. The method of Embodiment 31 wherein $R^9$ is methyl.
Embodiment 34. The method of Embodiment 1 wherein $R^{10}$ is $C_1$-$C_4$ alkyl.
Embodiment 35. The method of Embodiment 1 wherein $R^{11}$ is H.
Embodiment 36. The method of Embodiment 1 wherein $R^{12}$ is $C_1$-$C_4$ alkyl or $C_1$-$C_4$ haloalkyl, each optionally substituted with one $R^{13}$.
Embodiment 37. The method of Embodiment 1 wherein $R^{12}$ is $C_1$-$C_4$ alkyl or $C_1$-$C_4$ haloalkyl.
Embodiment 38. The method of Embodiment 37 wherein $R^{12}$ is $C_1$-$C_4$ haloalkyl.
Embodiment 38a. The method of Embodiment 1 wherein $R^{12}$ is cyclopropyl or cyclopropylmethyl.
Embodiment 39. The method of Embodiment 1 wherein $R^{13}$ is cyano, OH, $OR^{14}$ or $S(O)_nR^{16}$.
Embodiment 40. The method of Embodiment 39 wherein $R^{13}$ is cyano.
Embodiment 41. The method of Embodiment 39 wherein $R^{13}$ is OH.
Embodiment 42. The method of Embodiment 39 wherein $R^{13}$ is $OR^{14}$.
Embodiment 43. The method of Embodiment 39 wherein $R^{13}$ is $S(O)_nR^{16}$.
Embodiment 44. The method of Embodiment 1 wherein the pesticidally effective amount of a compound of Formula 1 is administered orally.
Embodiment 45. The method of Embodiment 1 wherein the pesticidally effective amount of a compound of Formula 1 is administered parenterally.
Embodiment 46. The method of Embodiment 45 wherein the pesticidally effective amount of a compound of Formula 1 is administered by injection.
Embodiment 47. The method of Embodiment 1 wherein the animal to be protected is a vertebrate.
Embodiment 48. The method of Embodiment 47 wherein the vertebrate to be protected is a mammal, avian or fish.
Embodiment 49. The method of Embodiment 48 wherein the vertebrate to be protected is a mammal.
Embodiment 50. The method of Embodiment 48 wherein the vertebrate to be protected is an avian.
Embodiment 51. The method of Embodiment 48 wherein the vertebrate to be protected is a fish.
Embodiment 52. The method of Embodiment 49 wherein the mammal to be protected is a human.
Embodiment 53. The method of Embodiment 49 wherein the mammal to be protected is livestock.
Embodiment 54. The method of Embodiment 49 wherein the mammal to be protected is a canine.
Embodiment 55. The method of Embodiment 49 wherein the mammal to be protected is a feline.
Embodiment 56. The method of Embodiment 1 wherein the parasitic invertebrate pest is an ectoparasite.
Embodiment 57. The method of Embodiment 1 wherein the parasitic invertebrate pest is an endoparasite.
Embodiment 58. The method of Embodiment 1 wherein the parasitic invertebrate pest is an helminth.
Embodiment 59. The method of Embodiment 1 wherein the parasitic invertebrate pest is an arthropod.
Embodiment 60. The method of Embodiment 1 wherein the parasitic invertebrate pest is a fly, mosquito, mite, tick, louse, flea, true bug or maggot.
Embodiment 61. The method of Embodiment 1 wherein the parasitic invertebrate pest is a fly, mosquito, mite, tick, louse, flea, bed bug, kissing bug or maggot.
Embodiment 62. The method of Embodiment 61 wherein the parasitic invertebrate pest is a fly or maggot.
Embodiment 63. The method of Embodiment 61 wherein the parasitic invertebrate pest is a mosquito.
Embodiment 64. The method of Embodiment 61 wherein the parasitic invertebrate pest is a tick or mite.
Embodiment 65. The method of Embodiment 61 wherein the parasitic invertebrate pest is a louse.

Embodiment 66. The method of Embodiment 61 wherein the parasitic invertebrate pest is a flea.
Embodiment 67. The method of Embodiment 61 wherein the parasitic invertebrate pest is a true bug.
Embodiment 68. The method of Embodiment 61 wherein the parasitic invertebrate pest is a bed bug or kissing bug.
Embodiment 69. The method of Embodiment 61 wherein the animal to be protected is a cat or dog and the parasitic invertebrate pest is a flea, tick or mite.
Embodiment 70. The method of Embodiment 44 wherein the parasiticidally effective amount of a compound of Formula 1 is administered orally two times a year.
Embodiment 71. The method of Embodiment 44 wherein the parasiticidally effective amount of a compound of Formula 1 is administered orally once a month.
Embodiment 72. The method of Embodiment 44 wherein the parasiticidally effective amount of a compound of Formula 1 is administered orally two times a month.

Embodiments of this invention, including Embodiments 1-72 above as well as any other embodiments described herein, can be combined in any manner.

Combinations of Embodiments 1-43 are illustrated by:

Embodiment A. The method of Embodiment 1 wherein
$R^1$ is Cl, Br or $CF_3$;
$R^2$ is H, F or Cl; and
$R^3$ is H, Cl, Br or $CF_3$.

Embodiment B. A method of Embodiment A wherein
$R^1$ and $R^3$ are Cl; and
$R^2$ is H.

Embodiment C. A method of Embodiment A wherein
$R^1$ and $R^3$ are Br; and
$R^2$ is H.

Embodiment D. A method of Embodiment A wherein
$R^1$ and $R^3$ are $CF_3$; and
$R^2$ is H.

Embodiment E. A method of Embodiment A wherein
$R^1$, $R^2$ and $R^3$ are Cl.

Embodiment F. A method of Embodiment A wherein
$R^1$ and $R^3$ are Cl; and
$R^2$ is F.

Embodiment G. A method of Embodiment A wherein
$R^1$ is $CF_3$; and
$R^2$ and $R^3$ are H.

Embodiment H. A method of Embodiment A wherein
$R^4$ is methyl; and
$R^5$ is H.

Embodiment I. A method of Embodiment A wherein
$R^5$ is H;
$R^6$ is $C_1$-$C_6$ alkyl substituted with one $R^7$; and
$R^7$ is $OR^9$, $S(O)_nR^{10}$ or $C(O)NR^{11}R^{12}$.

Embodiment J. A method of Embodiment A wherein
$R^7$ is $C(O)NR^{11}R^{12}$; and
$R^{12}$ is $C_1$-$C_4$ alkyl or $C_1$-$C_4$ haloalkyl, each optionally substituted with one $R^{13}$.

Embodiment K. A method of Embodiment A wherein
$R^4$ is $C_1$ or $CH_3$;
$R^5$ is H;
$R^6$ is $C_1$-$C_6$ alkyl substituted with one $R^7$; and
$R^7$ is $OR^9$, $S(O)_nR^{10}$ or $C(O)NR^{11}R^{12}$.

Embodiment L. A method of Embodiment K wherein
$R^1$ is Cl, Br, $CF_3$, $OCF_3$ or $OCH_2CF_3$;
$R^2$ is H; and
$R^3$ is H, F, Cl, Br or $CF_3$.

Embodiment M. A method of Embodiment L wherein
$R^4$ is $CH_3$; and
$R^7$ is $C(O)NR^{11}R^{12}$.

Embodiment N. A method of Embodiment M wherein
$R^1$ is $CF_3$; and
$R^3$ is Cl, Br or $CF_3$.

Embodiment O. A method of Embodiment M wherein
$R^{11}$ is H; and
$R^{12}$ is $C_1$-$C_4$ alkyl or $C_1$-$C_4$ haloalkyl.

Embodiment P. A method of Embodiment M wherein
$R^{11}$ is H; and
$R^{12}$ is cyclopropyl or cyclopropylmethyl.

Specific embodiments include the method of Embodiment 1 wherein compounds of Formula 1 are selected from the group consisting of:

4-[5-(3,5-dichlorophenyl)-4,5-dihydro-5-(trifluoromethyl)-3-isoxazolyl]-2-methyl-N-(2-pyridinylmethyl)benzamide, 4-[5-(3,5-dichlorophenyl)-4,5-dihydro-5-(trifluoromethyl)-3-isoxazolyl]-2-methyl-N-[2-oxo-2-[(2,2,2-trifluoroethyl)amino]ethyl]benzamide, 4-[5-(3,5-dichlorophenyl)-4,5-dihydro-5-(trifluoromethyl)-3-isoxazolyl]-2-methyl-N-[2-(methylthio)ethyl]benzamide, 4-[5-(3,5-dichlorophenyl)-4,5-dihydro-5-(trifluoromethyl)-3-isoxazolyl]-2-methyl-N-[2-(methylsulfinyl)ethyl]benzamide, 4-[5-(3,5-dichlorophenyl)-4,5-dihydro-5-(trifluoromethyl)-3-isoxazolyl]-2-methyl-N-[2-(methylsulfonyl)ethyl]benzamide, and 4-[5-(3,5-dichlorophenyl)-4,5-dihydro-5-(trifluoromethyl)-3-isoxazolyl]-2-methyl-N-[1-methyl-3-(methylthio)propyl]benzamide.

Further specific embodiments include the method of Embodiment 1 wherein compounds of Formula 1 are selected from Table A and B. The following abbreviation is used in Table A: c-Pr means cyclopropyl.

TABLE A

| $R^1$ | $R^3$ | $R^{12}$ |
|---|---|---|
| \multicolumn{3}{c}{$R^a$ is H} |
| Cl | Cl | $CH_3$ |
| Cl | Cl | $CH_2CH_3$ |
| Cl | Cl | $CH(CH_3)_2$ |
| Cl | Cl | $CH_2CF_3$ |
| Cl | Cl | c-Pr |
| Cl | Cl | $CH_2$-c-Pr |
| Cl | $CF_3$ | $CH_3$ |
| Cl | $CF_3$ | $CH_2CH_3$ |
| Cl | $CF_3$ | $CH(CH_3)_2$ |
| Cl | $CF_3$ | $CH_2CF_3$ |
| Cl | $CF_3$ | c-Pr |
| Cl | $CF_3$ | $CH_2$-c-Pr |
| Cl | $OCH_2CF_3$ | $CH_3$ |
| Cl | $OCH_2CF_3$ | $CH_2CH_3$ |
| Cl | $OCH_2CF_3$ | $CH(CH_3)_2$ |
| Cl | $OCH_2CF_3$ | $CH_2CF_3$ |
| Cl | $OCH_2CF_3$ | c-Pr |
| Cl | $OCH_2CF_3$ | $CH_2$-c-Pr |
| Br | $CF_3$ | $CH_3$ |
| Br | $CF_3$ | $CH_2CH_3$ |

TABLE A-continued

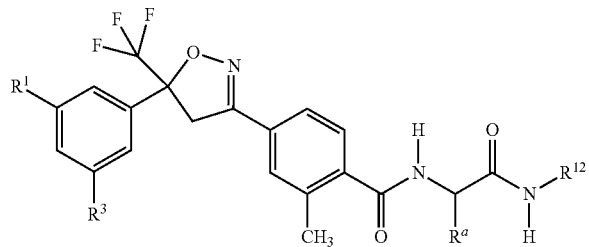

| R¹ | R³ | R¹² |
|---|---|---|
| Br | CF₃ | CH(CH₃)₂ |
| Br | CF₃ | CH₂CF₃ |
| Br | CF₃ | c-Pr |
| Br | CF₃ | CH₂-c-Pr |
| CF₃ | CF₃ | CH₃ |
| CF₃ | CF₃ | CH₂CH₃ |
| CF₃ | CF₃ | CH(CH₃)₂ |
| CF₃ | CF₃ | CH₂CF₃ |
| CF₃ | CF₃ | c-Pr |
| CF₃ | CF₃ | CH₂-c-Pr |
| Rᵃ is CH₃ | | |
| Cl | Cl | CH₃ |
| Cl | Cl | CH₂CH₃ |
| Cl | Cl | CH(CH₃)₂ |
| Cl | Cl | CH₂CF₃ |
| Cl | Cl | c-Pr |
| Cl | Cl | CH₂-c-Pr |
| Cl | CF₃ | CH₃ |
| Cl | CF₃ | CH₂CH₃ |
| Cl | CF₃ | CH(CH₃)₂ |
| Cl | CF₃ | CH₂CF₃ |

TABLE A-continued

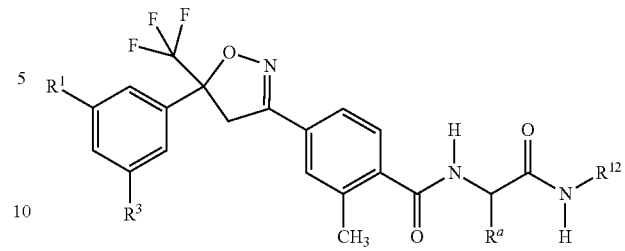

| R¹ | R³ | R¹² |
|---|---|---|
| Cl | CF₃ | c-Pr |
| Cl | CF₃ | CH₂-c-Pr |
| Cl | OCH₂CF₃ | CH₃ |
| Cl | OCH₂CF₃ | CH₂CH₃ |
| Cl | OCH₂CF₃ | CH(CH₃)₂ |
| Cl | OCH₂CF₃ | CH₂CF₃ |
| Cl | OCH₂CF₃ | c-Pr |
| Cl | OCH₂CF₃ | CH₂-c-Pr |
| Br | CF₃ | CH₃ |
| Br | CF₃ | CH₂CH₃ |
| Br | CF₃ | CH(CH₃)₂ |
| Br | CF₃ | CH₂CF₃ |
| Br | CF₃ | c-Pr |
| Br | CF₃ | CH₂-c-Pr |
| CF₃ | CF₃ | CH₃ |
| CF₃ | CF₃ | CH₂CH₃ |
| CF₃ | CF₃ | CH(CH₃)₂ |
| CF₃ | CF₃ | CH₂CF₃ |
| CF₃ | CF₃ | c-Pr |
| CF₃ | CF₃ | CH₂-c-Pr |

TABLE B

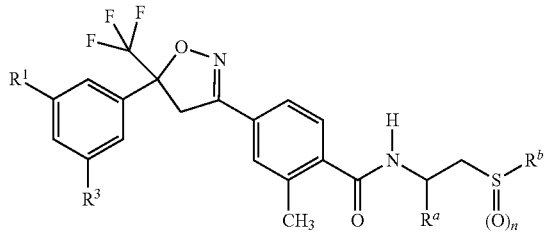

| R¹ | R³ | n | Rᵇ |
|---|---|---|---|
| Rᵃ is H | | | |
| Cl | Cl | 0 | CH₃ |
| Cl | Cl | 1 | CH₃ |
| Cl | Cl | 2 | CH₃ |
| Cl | Cl | 0 | CH₂CH₃ |
| Cl | Cl | 1 | CH₂CH₃ |
| Cl | Cl | 2 | CH₂CH₃ |
| Cl | CF₃ | 0 | CH₃ |
| Cl | CF₃ | 1 | CH₃ |
| Cl | CF₃ | 2 | CH₃ |
| Cl | CF₃ | 0 | CH₂CH₃ |
| Cl | CF₃ | 1 | CH₂CH₃ |
| Cl | CF₃ | 2 | CH₂CH₃ |
| Cl | OCH₂CF₃ | 0 | CH₃ |
| Cl | OCH₂CF₃ | 1 | CH₃ |
| Cl | OCH₂CF₃ | 2 | CH₃ |
| Cl | OCH₂CF₃ | 0 | CH₂CH₃ |
| Cl | OCH₂CF₃ | 1 | CH₂CH₃ |
| Cl | OCH₂CF₃ | 2 | CH₂CH₃ |
| Br | CF₃ | 0 | CH₃ |
| Br | CF₃ | 1 | CH₃ |
| Br | CF₃ | 2 | CH₃ |
| Br | CF₃ | 0 | CH₂CH₃ |
| Br | CF₃ | 1 | CH₂CH₃ |

TABLE B-continued

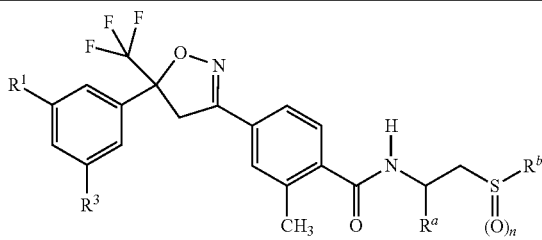

| $R^1$ | $R^3$ | n | $R^b$ |
|---|---|---|---|
| Br | $CF_3$ | 2 | $CH_2CH_3$ |
| $CF_3$ | $CF_3$ | 0 | $CH_3$ |
| $CF_3$ | $CF_3$ | 1 | $CH_3$ |
| $CF_3$ | $CF_3$ | 2 | $CH_3$ |
| $CF_3$ | $CF_3$ | 0 | $CH_2CH_3$ |
| $CF_3$ | $CF_3$ | 1 | $CH_2CH_3$ |
| $CF_3$ | $CF_3$ | 2 | $CH_2CH_3$ |
| $R^a$ $CH_3$ | | | |
| Cl | Cl | 0 | $CH_3$ |
| Cl | Cl | 1 | $CH_3$ |
| Cl | Cl | 2 | $CH_3$ |
| Cl | Cl | 0 | $CH_2CH_3$ |
| Cl | Cl | 1 | $CH_2CH_3$ |
| Cl | Cl | 2 | $CH_2CH_3$ |
| Cl | $CF_3$ | 0 | $CH_3$ |
| Cl | $CF_3$ | 1 | $CH_3$ |
| Cl | $CF_3$ | 2 | $CH_3$ |
| Cl | $CF_3$ | 0 | $CH_2CH_3$ |
| Cl | $CF_3$ | 1 | $CH_2CH_3$ |
| Cl | $CF_3$ | 2 | $CH_2CH_3$ |
| Cl | $OCH_2CF_3$ | 0 | $CH_3$ |
| Cl | $OCH_2CF_3$ | 1 | $CH_3$ |
| Cl | $OCH_2CF_3$ | 2 | $CH_3$ |
| Cl | $OCH_2CF_3$ | 0 | $CH_2CH_3$ |
| Cl | $OCH_2CF_3$ | 1 | $CH_2CH_3$ |
| Cl | $OCH_2CF_3$ | 2 | $CH_2CH_3$ |
| Br | $CF_3$ | 0 | $CH_3$ |
| Br | $CF_3$ | 1 | $CH_3$ |
| Br | $CF_3$ | 2 | $CH_3$ |
| Br | $CF_3$ | 0 | $CH_2CH_3$ |
| Br | $CF_3$ | 1 | $CH_2CH_3$ |
| Br | $CF_3$ | 2 | $CH_2CH_3$ |
| $CF_3$ | $CF_3$ | 0 | $CH_3$ |
| $CF_3$ | $CF_3$ | 1 | $CH_3$ |
| $CF_3$ | $CF_3$ | 2 | $CH_3$ |
| $CF_3$ | $CF_3$ | 0 | $CH_2CH_3$ |
| $CF_3$ | $CF_3$ | 1 | $CH_2CH_3$ |
| $CF_3$ | $CF_3$ | 2 | $CH_2CH_3$ |

The compounds of Formula 1 or any of Embodiments 1-43 or Embodiments A-P can be used for the protection of an animal from an invertebrate parasitic pest by oral or parenteral administration of the compound.

Therefore, the invention is understood to include the compounds of Formula 1 or any of Embodiments 1-43 or Embodiments A-P (and compositions containing them) for use as an animal medicament, or more particularly a parasiticidal animal medicament. The animals to be protected are as defined in any of Embodiments 47-55. The invertebrate parasitic pests are as defined in any of Embodiments 56-68. The medicament may be in oral or parenteral dosage forms.

The invention is also understood to include the use of compounds of Formula 1 or any of Embodiments 1-43 or Embodiments A-P in the manufacture of medicaments for the protection of an animal from a an invertebrate parasitic pest. The animals to be protected are as defined in any of Embodiments 47-55. The invertebrate parasitic pests are as defined in any of Embodiments 56-68. The medicament may be in oral or parenteral dosage forms.

The invention is also understood to include compounds of Formula 1 or any of Embodiments 1-43 or Embodiments A-P for use in the manufacture of medicaments for the protection of an animal from an invertebrate parasitic pest. The animals to be protected are as defined in any of Embodiments 47-55. The invertebrate parasitic pests are as defined in any of Embodiments 56-68. The medicament may be in oral or parenteral dosage forms.

The invention is also understood to include compounds of Formula 1 or any of Embodiments 1-43 or Embodiments A-P packaged and presented for the protection of an animal from an invertebrate parasitic pest. The animals to be protected are as defined in any of Embodiments 47-55. The invertebrate parasitic pests are as defined in any of Embodiments 56-68. The compounds of the invention may be packaged and presented as oral or parenteral dosage forms.

The invention is also understood to include a process for manufacturing a composition for protecting an animal from an invertebrate parasitic pest characterized in that a compound of Claim 1 is admixed with at least one pharmaceutically or veterinarily acceptable carrier. The animals to be protected are as defined in any of Embodiments 47-55. The invertebrate parasitic pests are as defined in any of Embodiments 56-68. The compositions of the invention may be packaged and presented as oral or parenteral dosage forms.

Isoxazolines of Formula 1 can be prepared as described in PCT Patent Publication WO 2005/085216.

One skilled in the art will appreciate that not all pyridine heterocycles can form N-oxides; one skilled in the art will recognize those pyridine heterocycles which can form N-oxides. Synthetic methods for the preparation of N-oxides of pyridine heterocycles are very well known by one skilled in the art including the oxidation of heterocycles with peroxy acids such as peracetic and m-chloroperbenzoic acid (MCPBA), hydrogen peroxide, alkyl hydroperoxides such as t-butyl hydroperoxide, sodium perborate, and dioxiranes such as dimethyldioxirane. These methods for the preparation of N-oxides have been extensively described and reviewed in the literature, see for example: T. L. Gilchrist in *Comprehensive Organic Synthesis*, vol. 7, pp 748-750, S. V. Ley, Ed., Pergamon Press; M. Tisler and B. Stanovnik in *Comprehensive Heterocyclic Chemistry*, vol. 3, pp 18-20, A. J. Boulton and A. McKillop, Eds., Pergamon Press; M. R. Grimmett and B. R. T. Keene in *Advances in Heterocyclic Chemistry*, vol. 43, pp 149-161, A. R. Katritzky, Ed., Academic Press; M. Tisler and B. Stanovnik in *Advances in Heterocyclic Chemistry*, vol. 9, pp 285-291, A. R. Katritzky and A. J. Boulton, Eds., Academic Press; and G. W. H. Cheeseman and E. S. G. Werstiuk in *Advances in Heterocyclic Chemistry*, vol. 22, pp 390-392, A. R. Katritzky and A. J. Boulton, Eds., Academic Press.

One skilled in the art recognizes that because in the environment and under physiological conditions salts of chemical compounds are in equilibrium with their corresponding nonsalt forms, salts share the biological utility of the nonsalt forms. Thus a wide variety of salts of the compounds of Formula 1 are useful for control of invertebrate pests and animal parasites. The salts of the compounds of Formula 1 include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids. Accordingly, the method of the present invention comprises compounds selected from Formula 1, N-oxides and salts thereof.

By the procedures described in PCT Patent Publication WO 2005/085216 together with methods known in the art, the following compounds of Tables 1-4 can be prepared. These tables disclose specific compounds illustrative of compounds of Formula 1 useful in the present method. The following abbreviations are used in the Tables which follow: Me means methyl, Et means ethyl, n-Pr means $CH_2CH_2CH_3$, i-Pr means $CH(CH_3)_2$, c-Pr means cyclopropyl, i-Bu means $CH_2CH(CH_3)_2$, s-Bu means $CH(CH_3)CH_2CH_3$, t-Bu means $C(CH_3)_3$, S(O) means sulfinyl, S(O)$_2$ means sulfonyl, and C(O) means carbonyl.

TABLE 1

[Structure of isoxazoline compound with substituents $R^1$, $R^3$ on one phenyl ring, $CF_2F$ group, and benzamide with Cl and $NHR^6$ group]

| | $R^6$ |
|---|---|
| \multicolumn{2}{c}{$R^1$ is Cl, $R^3$ is Cl} |
| $CH_2CH_2SMe$ | $CH(Me)C(O)NH(Et)$ |
| $CH_2CH_2SEt$ | $CH(Me)C(O)NH(n-Pr)$ |
| $CH_2CH_2S(n-Pr)$ | $CH(Me)C(O)NH(i-Pr)$ |
| $CH_2CH_2CH_2SMe$ | $CH(Me)C(O)NH(i-Bu)$ |
| $CH_2CH_2CH_2SEt$ | $CH(Me)C(O)NH(s-Bu)$ |
| $CH_2CH_2S(O)Me$ | $CH_2(4$-thiazolyl$)$ |
| $CH_2CH_2S(O)Et$ | $CH_2C(O)N(Me)CH_2CF_3$ |
| $CH_2CH_2S(O)(n-Pr)$ | $CH(Me)C(O)N(Me)CH_2CF_3$ |
| $CH_2CH_2CH_2S(O)Me$ | $CH_2C(O)NH(c-Pr)$ |
| $CH_2CH_2CH_2S(O)Et$ | $CH_2C(O)NH(CH_2$-c-Pr$)$ |
| $CH_2CH_2SO_2Me$ | $CH_2C(O)NHCH_2CH_2Cl$ |
| $CH_2CH_2SO_2Et$ | $CH_2C(O)NHCH_2CHF_2$ |
| $CH_2CH_2SO_2(n-Pr)$ | $CH_2C(O)NHCH_2CF_3$ |
| $CH_2CH_2CH_2SO_2Me$ | $CH_2C(O)NHCH_2CH_2CF_3$ |
| $CH_2CH_2CH_2SO_2Et$ | $CH_2C(O)NHCH(Me)CF_3$ |
| $CH_2(2$-pyridinyl$)$ | $CH_2C(O)NHCH_2CH(Me)CF_3$ |
| $CH_2C(O)NH_2$ | $CH(Me)C(O)NH(c-Pr)$ |
| $CH_2C(O)NH(Me)$ | $CH(Me)C(O)NH(CH_2$-c-Pr$)$ |
| $CH_2C(O)NH(Et)$ | $CH(Me)C(O)NHCH_2CH_2Cl$ |
| $CH_2C(O)NH(n-Pr)$ | $CH(Me)C(O)NHCH_2CHF_2$ |
| $CH_2C(O)NH(i-Pr)$ | $CH(Me)C(O)NHCH_2CF_3$ |
| $CH_2C(O)NH(i-Bu)$ | $CH(Me)C(O)NHCH_2CH_2CF_3$ |
| $CH_2C(O)NH(s-Bu)$ | $CH(Me)C(O)NHCH(Me)CF_3$ |
| $CH(Me)C(O)NH(Me)$ | $CH(Me)C(O)NHCH_2CH(Me)CF_3$ |
| \multicolumn{2}{c}{$R^1$ is Br, $R^3$ is Br} |
| $CH_2CH_2SMe$ | $CH(Me)C(O)NH(Et)$ |
| $CH_2CH_2SEt$ | $CH(Me)C(O)NH(n-Pr)$ |
| $CH_2CH_2S(n-Pr)$ | $CH(Me)C(O)NH(i-Pr)$ |
| $CH_2CH_2CH_2SMe$ | $CH(Me)C(O)NH(i-Bu)$ |
| $CH_2CH_2CH_2SEt$ | $CH(Me)C(O)NH(s-Bu)$ |
| $CH_2CH_2S(O)Me$ | $CH_2(4$-thiazolyl$)$ |
| $CH_2CH_2S(O)Et$ | $CH_2C(O)N(Me)CH_2CF_3$ |
| $CH_2CH_2S(O)(n-Pr)$ | $CH(Me)C(O)N(Me)CH_2CF_3$ |
| $CH_2CH_2CH_2S(O)Me$ | $CH_2C(O)NH(c-Pr)$ |
| $CH_2CH_2CH_2S(O)Et$ | $CH_2C(O)NH(CH_2$-c-Pr$)$ |
| $CH_2CH_2SO_2Me$ | $CH_2C(O)NHCH_2CH_2Cl$ |
| $CH_2CH_2SO_2Et$ | $CH_2C(O)NHCH_2CHF_2$ |
| $CH_2CH_2SO_2(n-Pr)$ | $CH_2C(O)NHCH_2CF_3$ |
| $CH_2CH_2CH_2SO_2Me$ | $CH_2C(O)NHCH_2CH_2CF_3$ |
| $CH_2CH_2CH_2SO_2Et$ | $CH_2C(O)NHCH(Me)CF_3$ |
| $CH_2(2$-pyridinyl$)$ | $CH_2C(O)NHCH_2CH(Me)CF_3$ |
| $CH_2C(O)NH_2$ | $CH(Me)C(O)NH(c-Pr)$ |
| $CH_2C(O)NH(Me)$ | $CH(Me)C(O)NH(CH_2$-c-Pr$)$ |
| $CH_2C(O)NH(Et)$ | $CH(Me)C(O)NHCH_2CH_2Cl$ |
| $CH_2C(O)NH(n-Pr)$ | $CH(Me)C(O)NHCH_2CHF_2$ |
| $CH_2C(O)NH(i-Pr)$ | $CH(Me)C(O)NHCH_2CF_3$ |
| $CH_2C(O)NH(i-Bu)$ | $CH(Me)C(O)NHCH_2CH_2CF_3$ |
| $CH_2C(O)NH(s-Bu)$ | $CH(Me)C(O)NHCH(Me)CF_3$ |
| $CH(Me)C(O)NH(Me)$ | $CH(Me)C(O)NHCH_2CH(Me)CF_3$ |
| \multicolumn{2}{c}{$R^1$ is $CF_3$, $R^3$ is H} |
| $CH_2CH_2SMe$ | $CH(Me)C(O)NH(Et)$ |
| $CH_2CH_2SEt$ | $CH(Me)C(O)NH(n-Pr)$ |
| $CH_2CH_2S(n-Pr)$ | $CH(Me)C(O)NH(i-Pr)$ |
| $CH_2CH_2CH_2SMe$ | $CH(Me)C(O)NH(i-Bu)$ |
| $CH_2CH_2CH_2SEt$ | $CH(Me)C(O)NH(s-Bu)$ |
| $CH_2CH_2S(O)Me$ | $CH_2(4$-thiazolyl$)$ |
| $CH_2CH_2S(O)Et$ | $CH_2C(O)N(Me)CH_2CF_3$ |
| $CH_2CH_2S(O)(n-Pr)$ | $CH(Me)C(O)N(Me)CH_2CF_3$ |
| $CH_2CH_2CH_2S(O)Me$ | $CH_2C(O)NH(c-Pr)$ |
| $CH_2CH_2CH_2S(O)Et$ | $CH_2C(O)NH(CH_2$-c-Pr$)$ |
| $CH_2CH_2SO_2Me$ | $CH_2C(O)NHCH_2CH_2Cl$ |

TABLE 1-continued

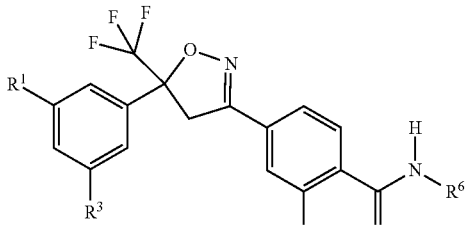

| R⁶ | |
|---|---|
| CH₂CH₂SO₂Et | CH₂C(O)NHCH₂CHF₂ |
| CH₂CH₂SO₂(n-Pr) | CH₂C(O)NHCH₂CF₃ |
| CH₂CH₂CH₂SO₂Me | CH₂C(O)NHCH₂CH₂CF₃ |
| CH₂CH₂CH₂SO₂Et | CH₂C(O)NHCH(Me)CF₃ |
| CH₂(2-pyridinyl) | CH₂C(O)NHCH₂CH(Me)CF₃ |
| CH₂C(O)NH₂ | CH(Me)C(O)NH(c-Pr) |
| CH₂C(O)NH(Me) | CH(Me)C(O)NH(CH₂-c-Pr) |
| CH₂C(O)NH(Et) | CH(Me)C(O)NHCH₂CH₂Cl |
| CH₂C(O)NH(n-Pr) | CH(Me)C(O)NHCH₂CHF₂ |
| CH₂C(O)NH(i-Pr) | CH(Me)C(O)NHCH₂CF₃ |
| CH₂C(O)NH(i-Bu) | CH(Me)C(O)NHCH₂CH₂CF₃ |
| CH₂C(O)NH(s-Bu) | CH(Me)C(O)NHCH(Me)CF₃ |
| CH(Me)C(O)NH(Me) | CH(Me)C(O)NHCH₂CH(Me)CF₃ |

R¹ is CF₃, R³ is F

| | |
|---|---|
| CH₂CH₂SMe | CH(Me)C(O)NH(Et) |
| CH₂CH₂SEt | CH(Me)C(O)NH(n-Pr) |
| CH₂CH₂S(n-Pr) | CH(Me)C(O)NH(i-Pr) |
| CH₂CH₂CH₂SMe | CH(Me)C(O)NH(i-Bu) |
| CH₂CH₂CH₂SEt | CH(Me)C(O)NH(s-Bu) |
| CH₂CH₂S(O)Me | CH₂(4-thiazolyl) |
| CH₂CH₂S(O)Et | CH₂C(O)N(Me)CH₂CF₃ |
| CH₂CH₂S(O)(n-Pr) | CH(Me)C(O)N(Me)CH₂CF₃ |
| CH₂CH₂CH₂S(O)Me | CH₂C(O)NH(c-Pr) |
| CH₂CH₂CH₂S(O)Et | CH₂C(O)NH(CH₂-c-Pr) |
| CH₂CH₂SO₂Me | CH₂C(O)NHCH₂CH₂Cl |
| CH₂CH₂SO₂Et | CH₂C(O)NHCH₂CHF₂ |
| CH₂CH₂SO₂(n-Pr) | CH₂C(O)NHCH₂CF₃ |
| CH₂CH₂CH₂SO₂Me | CH₂C(O)NHCH₂CH₂CF₃ |
| CH₂CH₂CH₂SO₂Et | CH₂C(O)NHCH(Me)CF₃ |
| CH₂(2-pyridinyl) | CH₂C(O)NHCH₂CH(Me)CF₃ |
| CH₂C(O)NH₂ | CH(Me)C(O)NH(c-Pr) |
| CH₂C(O)NH(Me) | CH(Me)C(O)NH(CH₂-c-Pr) |
| CH₂C(O)NH(Et) | CH(Me)C(O)NHCH₂CH₂Cl |
| CH₂C(O)NH(n-Pr) | CH(Me)C(O)NHCH₂CHF₂ |
| CH₂C(O)NH(i-Pr) | CH(Me)C(O)NHCH₂CF₃ |
| CH₂C(O)NH(i-Bu) | CH(Me)C(O)NHCH₂CH₂CF₃ |
| CH₂C(O)NH(s-Bu) | CH(Me)C(O)NHCH(Me)CF₃ |
| CH(Me)C(O)NH(Me) | CH(Me)C(O)NHCH₂CH(Me)CF₃ |

R¹ is CF₃, R³ is Cl

| | |
|---|---|
| CH₂CH₂SMe | CH(Me)C(O)NH(Et) |
| CH₂CH₂SEt | CH(Me)C(O)NH(n-Pr) |
| CH₂CH₂S(n-Pr) | CH(Me)C(O)NH(i-Pr) |
| CH₂CH₂CH₂SMe | CH(Me)C(O)NH(i-Bu) |
| CH₂CH₂CH₂SEt | CH(Me)C(O)NH(s-Bu) |
| CH₂CH₂S(O)Me | CH₂(4-thiazolyl) |
| CH₂CH₂S(O)Et | CH₂C(O)N(Me)CH₂CF₃ |
| CH₂CH₂S(O)(n-Pr) | CH(Me)C(O)N(Me)CH₂CF₃ |
| CH₂CH₂CH₂S(O)Me | CH₂C(O)NH(c-Pr) |
| CH₂CH₂CH₂S(O)Et | CH₂C(O)NH(CH₂-c-Pr) |
| CH₂CH₂SO₂Me | CH₂C(O)NHCH₂CH₂Cl |
| CH₂CH₂SO₂Et | CH₂C(O)NHCH₂CHF₂ |
| CH₂CH₂SO₂(n-Pr) | CH₂C(O)NHCH₂CF₃ |
| CH₂CH₂CH₂SO₂Me | CH₂C(O)NHCH₂CH₂CF₃ |
| CH₂CH₂CH₂SO₂Et | CH₂C(O)NHCH(Me)CF₃ |
| CH₂(2-pyridinyl) | CH₂C(O)NHCH₂CH(Me)CF₃ |
| CH₂C(O)NH₂ | CH(Me)C(O)NH(c-Pr) |
| CH₂C(O)NH(Me) | CH(Me)C(O)NH(CH₂-c-Pr) |
| CH₂C(O)NH(Et) | CH(Me)C(O)NHCH₂CH₂Cl |
| CH₂C(O)NH(n-Pr) | CH(Me)C(O)NHCH₂CHF₂ |
| CH₂C(O)NH(i-Pr) | CH(Me)C(O)NHCH₂CF₃ |
| CH₂C(O)NH(i-Bu) | CH(Me)C(O)NHCH₂CH₂CF₃ |
| CH₂C(O)NH(s-Bu) | CH(Me)C(O)NHCH(Me)CF₃ |
| CH(Me)C(O)NH(Me) | CH(Me)C(O)NHCH₂CH(Me)CF₃ |

TABLE 1-continued

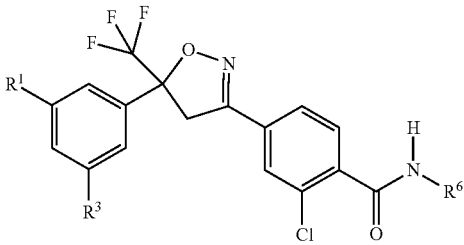

| R⁶ | |
|---|---|

R¹ is CF₃, R³ is Br

| | |
|---|---|
| CH₂CH₂SMe | CH(Me)C(O)NH(Et) |
| CH₂CH₂SEt | CH(Me)C(O)NH(n-Pr) |
| CH₂CH₂S(n-Pr) | CH(Me)C(O)NH(i-Pr) |
| CH₂CH₂CH₂SMe | CH(Me)C(O)NH(i-Bu) |
| CH₂CH₂CH₂SEt | CH(Me)C(O)NH(s-Bu) |
| CH₂CH₂S(O)Me | CH₂(4-thiazolyl) |
| CH₂CH₂S(O)Et | CH₂C(O)N(Me)CH₂CF₃ |
| CH₂CH₂S(O)(n-Pr) | CH(Me)C(O)N(Me)CH₂CF₃ |
| CH₂CH₂CH₂S(O)Me | CH₂C(O)NH(c-Pr) |
| CH₂CH₂CH₂S(O)Et | CH₂C(O)NH(CH₂-c-Pr) |
| CH₂CH₂SO₂Me | CH₂C(O)NHCH₂CH₂Cl |
| CH₂CH₂SO₂Et | CH₂C(O)NHCH₂CHF₂ |
| CH₂CH₂SO₂(n-Pr) | CH₂C(O)NHCH₂CF₃ |
| CH₂CH₂CH₂SO₂Me | CH₂C(O)NHCH₂CH₂CF₃ |
| CH₂CH₂CH₂SO₂Et | CH₂C(O)NHCH(Me)CF₃ |
| CH₂(2-pyridinyl) | CH₂C(O)NHCH₂CH(Me)CF₃ |
| CH₂C(O)NH₂ | CH(Me)C(O)NH(c-Pr) |
| CH | CH(Me)C(O)NH(CH₂-c-Pr) |
| CH₂C(O)NH(Et) | CH(Me)C(O)NHCH₂CH₂Cl |
| CH₂C(O)NH(n-Pr) | CH(Me)C(O)NHCH₂CHF₂ |
| CH₂C(O)NH(i-Pr) | CH(Me)C(O)NHCH₂CF₃ |
| CH₂C(O)NH(i-Bu) | CH(Me)C(O)NHCH₂CH₂CF₃ |
| CH₂C(O)NH(s-Bu) | CH(Me)C(O)NHCH(Me)CF₃ |
| CH(Me)C(O)NH(Me) | CH(Me)C(O)NHCH₂CH(Me)CF₃ |

R¹ is CF₃, R³ CF₃

| | |
|---|---|
| CH₂CH₂SMe | CH(Me)C(O)NH(Et) |
| CH₂CH₂SEt | CH(Me)C(O)NH(n-Pr) |
| CH₂CH₂S(n-Pr) | CH(Me)C(O)NH(i-Pr) |
| CH₂CH₂CH₂SMe | CH(Me)C(O)NH(i-Bu) |
| CH₂CH₂CH₂SEt | CH(Me)C(O)NH(s-Bu) |
| CH₂CH₂S(O)Me | CH₂(4-thiazolyl) |
| CH₂CH₂S(O)Et | CH₂C(O)N(Me)CH₂CF₃ |
| CH₂CH₂S(O)(n-Pr) | CH(Me)C(O)N(Me)CH₂CF₃ |
| CH₂CH₂CH₂S(O)Me | CH₂C(O)NH(c-Pr) |
| CH₂CH₂CH₂S(O)Et | CH₂C(O)NH(CH₂-c-Pr) |
| CH₂CH₂SO₂Me | CH₂C(O)NHCH₂CH₂Cl |
| CH₂CH₂SO₂Et | CH₂C(O)NHCH₂CHF₂ |
| CH₂CH₂SO₂(n-Pr) | CH₂C(O)NHCH₂CF₃ |
| CH₂CH₂CH₂SO₂Me | CH₂C(O)NHCH₂CH₂CF₃ |
| CH₂CH₂CH₂SO₂Et | CH₂C(O)NHCH(Me)CF₃ |
| CH₂(2-pyridinyl) | CH₂C(O)NHCH₂CH(Me)CF₃ |
| CH₂C(O)NH₂ | CH(Me)C(O)NH(c-Pr) |
| CH₂C(O)NH(Me) | CH(Me)C(O)NH(CH₂-c-Pr) |
| CH₂C(O)NH(Et) | CH(Me)C(O)NHCH₂CH₂Cl |
| CH₂C(O)NH(n-Pr) | CH(Me)C(O)NHCH₂CHF₂ |
| CH₂C(O)NH(i-Pr) | CH(Me)C(O)NHCH₂CF₃ |
| CH₂C(O)NH(i-Bu) | CH(Me)C(O)NHCH₂CH₂CF₃ |
| CH₂C(O)NH(s-Bu) | CH(Me)C(O)NHCH(Me)CF₃ |
| CH(Me)C(O)NH(Me) | CH(Me)C(O)NHCH₂CH(Me)CF₃ |

R¹ is OCF₃, R³ is Cl

| | |
|---|---|
| CH₂CH₂SMe | CH(Me)C(O)NH(Et) |
| CH₂CH₂SEt | CH(Me)C(O)NH(n-Pr) |
| CH₂CH₂S(n-Pr) | CH(Me)C(O)NH(i-Pr) |
| CH₂CH₂CH₂SMe | CH(Me)C(O)NH(i-Bu) |
| CH₂CH₂CH₂SEt | CH(Me)C(O)NH(s-Bu) |
| CH₂CH₂S(O)Me | CH₂(4-thiazolyl) |
| CH₂CH₂S(O)Et | CH₂C(O)N(Me)CH₂CF₃ |
| CH₂CH₂S(O)(n-Pr) | CH(Me)C(O)N(Me)CH₂CF₃ |
| CH₂CH₂CH₂S(O)Me | CH₂C(O)NH(c-Pr) |
| CH₂CH₂CH₂S(O)Et | CH₂C(O)NH(CH₂-c-Pr) |
| CH₂CH₂SO₂Me | CH₂C(O)NHCH₂CH₂Cl |

TABLE 1-continued

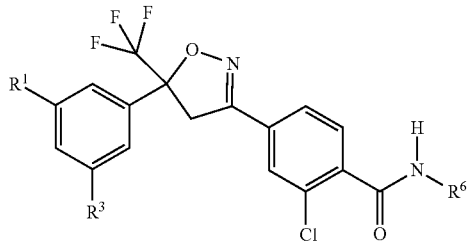

| R6 | |
|---|---|
| CH2CH2SO2Et | CH2C(O)NHCH2CHF2 |
| CH2CH2SO2(n-Pr) | CH2C(O)NHCH2CF3 |
| CH2CH2CH2SO2Me | CH2C(O)NHCH2CH2CF3 |
| CH2CH2CH2SO2Et | CH2C(O)NHCH(Me)CF3 |
| CH2(2-pyridinyl) | CH2C(O)NHCH2CH(Me)CF3 |
| CH2C(O)NH2 | CH(Me)C(O)NH(c-Pr) |
| CH2C(O)NH(Me) | CH(Me)C(O)NH(CH2-c-Pr) |
| CH2C(O)NH(Et) | CH(Me)C(O)NHCH2CH2Cl |
| CH2C(O)NH(n-Pr) | CH(Me)C(O)NHCH2CHF2 |
| CH2C(O)NH(i-Pr) | CH(Me)C(O)NHCH2CF3 |
| CH2C(O)NH(i-Bu) | CH(Me)C(O)NHCH2CH2CF3 |
| CH2C(O)NH(s-Bu) | CH(Me)C(O)NHCH(Me)CF3 |
| CH(Me)C(O)NH(Me) | CH(Me)C(O)NHCH2CH(Me)CF3 |

R1 is OCH2CF3, R3 is F

| | |
|---|---|
| CH2CH2SMe | CH(Me)C(O)NH(Et) |
| CH2CH2SEt | CH(Me)C(O)NH(n-Pr) |
| CH2CH2S(n-Pr) | CH(Me)C(O)NH(i-Pr) |
| CH2CH2CH2SMe | CH(Me)C(O)NH(i-Bu) |
| CH2CH2CH2SEt | CH(Me)C(O)NH(s-Bu) |
| CH2CH2S(O)Me | CH2(4-thiazolyl) |
| CH2CH2S(O)Et | CH2C(O)N(Me)CH2CF3 |
| CH2CH2S(O)(n-Pr) | CH(Me)C(O)N(Me)CH2CF3 |
| CH2CH2CH2S(O)Me | CH2C(O)NH(c-Pr) |
| CH2CH2CH2S(O)Et | CH2C(O)NH(CH2-c-Pr) |
| CH2CH2SO2Me | CH2C(O)NHCH2CH2Cl |
| CH2CH2SO2Et | CH2C(O)NHCH2CHF2 |
| CH2CH2SO2(n-Pr) | CH2C(O)NHCH2CF3 |
| CH2CH2CH2SO2Me | CH2C(O)NHCH2CH2CF3 |
| CH2CH2CH2SO2Et | CH2C(O)NHCH(Me)CF3 |
| CH2(2-pyridinyl) | CH2C(O)NHCH2CH(Me)CF3 |
| CH2C(O)NH2 | CH(Me)C(O)NH(c-Pr) |
| CH2C(O)NH(Me) | CH(Me)C(O)NH(CH2-c-Pr) |
| CH2C(O)NH(Et) | CH(Me)C(O)NHCH2CH2Cl |
| CH2C(O)NH(n-Pr) | CH(Me)C(O)NHCH2CHF2 |
| CH2C(O)NH(i-Pr) | CH(Me)C(O)NHCH2CF3 |
| CH2C(O)NH(i-Bu) | CH(Me)C(O)NHCH2CH2CF3 |
| CH2C(O)NH(s-Bu) | CH(Me)C(O)NHCH(Me)CF3 |
| CH(Me)C(O)NH(Me) | CH(Me)C(O)NHCH2CH(Me)CF3 |

R1 is OCH2CF3, R3 is Cl

| | |
|---|---|
| CH2CH2SMe | CH(Me)C(O)NH(Et) |
| CH2CH2SEt | CH(Me)C(O)NH(n-Pr) |
| CH2CH2S(n-Pr) | CH(Me)C(O)NH(i-Pr) |
| CH2CH2CH2SMe | CH(Me)C(O)NH(i-Bu) |
| CH2CH2CH2SEt | CH(Me)C(O)NH(s-Bu) |
| CH2CH2S(O)Me | CH2(4-thiazolyl) |
| CH2CH2S(O)Et | CH2C(O)N(Me)CH2CF3 |
| CH2CH2S(O)(n-Pr) | CH(Me)C(O)N(Me)CH2CF3 |
| CH2CH2CH2S(O)Me | CH2C(O)NH(c-Pr) |
| CH2CH2CH2S(O)Et | CH2C(O)NH(CH2-c-Pr) |
| CH2CH2SO2Me | CH2C(O)NHCH2CH2Cl |
| CH2CH2SO2Et | CH2C(O)NHCH2CHF2 |
| CH2CH2SO2(n-Pr) | CH2C(O)NHCH2CF3 |
| CH2CH2CH2SO2Me | CH2C(O)NHCH2CH2CF3 |
| CH2CH2CH2SO2Et | CH2C(O)NHCH(Me)CF3 |
| CH2(2-pyridinyl) | CH2C(O)NHCH2CH(Me)CF3 |
| CH2C(O)NH2 | CH(Me)C(O)NH(c-Pr) |
| CH2C(O)NH(Me) | CH(Me)C(O)NH(CH2-c-Pr) |
| CH2C(O)NH(Et) | CH(Me)C(O)NHCH2CH2Cl |
| CH2C(O)NH(n-Pr) | CH(Me)C(O)NHCH2CHF2 |
| CH2C(O)NH(i-Pr) | CH(Me)C(O)NHCH2CF3 |
| CH2C(O)NH(i-Bu) | CH(Me)C(O)NHCH2CH2CF3 |
| CH2C(O)NH(s-Bu) | CH(Me)C(O)NHCH(Me)CF3 |
| CH(Me)C(O)NH(Me) | CH(Me)C(O)NHCH2CH(Me)CF3 |

TABLE 1-continued

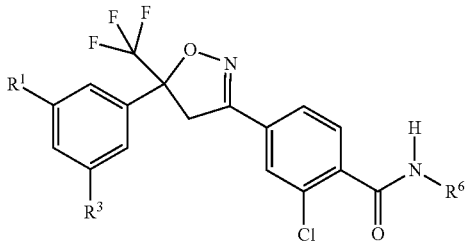

| R6 | |
|---|---|

R1 is OCH2CF3, R3 is Br

| | |
|---|---|
| CH2CH2SMe | CH(Me)C(O)NH(Et) |
| CH2CH2SEt | CH(Me)C(O)NH(n-Pr) |
| CH2CH2S(n-Pr) | CH(Me)C(O)NH(i-Pr) |
| CH2CH2CH2SMe | CH(Me)C(O)NH(i-Bu) |
| CH2CH2CH2SEt | CH(Me)C(O)NH(s-Bu) |
| CH2CH2S(O)Me | CH2(4-thiazolyl) |
| CH2CH2S(O)Et | CH2C(O)N(Me)CH2CF3 |
| CH2CH2S(O)(n-Pr) | CH(Me)C(O)N(Me)CH2CF3 |
| CH2CH2CH2S(O)Me | CH2C(O)NH(c-Pr) |
| CH2CH2CH2S(O)Et | CH2C(O)NH(CH2-c-Pr) |
| CH2CH2SO2Me | CH2C(O)NHCH2CH2Cl |
| CH2CH2SO2Et | CH2C(O)NHCH2CHF2 |
| CH2CH2SO2(n-Pr) | CH2C(O)NHCH2CF3 |
| CH2CH2CH2SO2Me | CH2C(O)NHCH2CH2CF3 |
| CH2CH2CH2SO2Et | CH2C(O)NHCH(Me)CF3 |
| CH2(2-pyridinyl) | CH2C(O)NHCH2CH(Me)CF3 |
| CH2C(O)NH2 | CH(Me)C(O)NH(c-Pr) |
| CH2C(O)NH(Me) | CH(Me)C(O)NH(CH2-c-Pr) |
| CH2C(O)NH(Et) | CH(Me)C(O)NHCH2CH2Cl |
| CH2C(O)NH(n-Pr) | CH(Me)C(O)NHCH2CHF2 |
| CH2C(O)NH(i-Pr) | CH(Me)C(O)NHCH2CF3 |
| CH2C(O)NH(i-Bu) | CH(Me)C(O)NHCH2CH2CF3 |
| CH2C(O)NH(s-Bu) | CH(Me)C(O)NHCH(Me)CF3 |
| CH(Me)C(O)NH(Me) | CH(Me)C(O)NHCH2CH(Me)CF3 |

TABLE 2

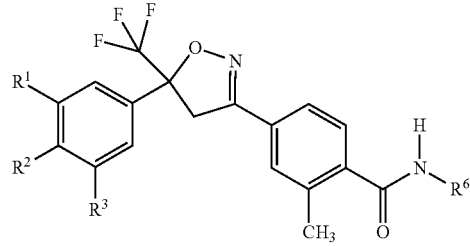

| R6 | |
|---|---|

R1 is Cl, R2 is Cl, R3 is Cl

| | |
|---|---|
| CH2CH2SMe | CH(Me)C(O)NH(Et) |
| CH2CH2SEt | CH(Me)C(O)NH(n-Pr) |
| CH2CH2S(n-Pr) | CH(Me)C(O)NH(i-Pr) |
| CH2CH2CH2SMe | CH(Me)C(O)NH(i-Bu) |
| CH2CH2CH2SEt | CH(Me)C(O)NH(s-Bu) |
| CH2CH2S(O)Me | CH2(4-thiazolyl) |
| CH2CH2S(O)Et | CH2C(O)N(Me)CH2CF3 |
| CH2CH2S(O)(n-Pr) | CH(Me)C(O)N(Me)CH2CF3 |
| CH2CH2CH2S(O)Me | CH2C(O)NH(c-Pr) |
| CH2CH2CH2S(O)Et | CH2C(O)NH(CH2-c-Pr) |
| CH2CH2SO2Me | CH2C(O)NHCH2CH2Cl |
| CH2CH2SO2Et | CH2C(O)NHCH2CHF2 |
| CH2CH2SO2(n-Pr) | CH2C(O)NHCH2CF3 |
| CH2CH2CH2 SO2Me | CH2C(O)NHCH2CH2CF3 |
| CH2CH2CH2 SO2Et | CH2C(O)NHCH(Me)CF3 |
| CH2(2-pyridinyl) | CH2C(O)NHCH2CH(Me)CF3 |
| CH2C(O)NH2 | CH(Me)C(O)NH(c-Pr) |

TABLE 2-continued

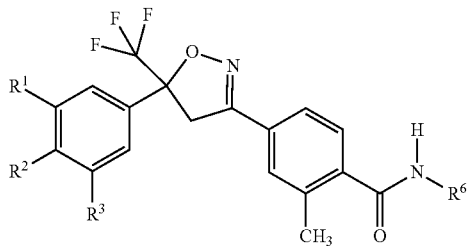

R⁶

| | |
|---|---|
| CH₂C(O)NH(Me) | CH(Me)C(O)NH(CH₂-c-Pr) |
| CH₂C(O)NH(Et) | CH(Me)C(O)NHCH₂CH₂Cl |
| CH₂C(O)NH(n-Pr) | CH(Me)C(O)NHCH₂CHF₂ |
| CH₂C(O)NH(i-Pr) | CH(Me)C(O)NHCH₂CF₃ |
| CH₂C(O)NH(i-Bu) | CH(Me)C(O)NHCH₂CH₂CF₃ |
| CH₂C(O)NH(s-Bu) | CH(Me)C(O)NHCH(Me)CF₃ |
| CH(Me)C(O)NH(Me) | CH(Me)C(O)NHCH₂CH(Me)CF₃ |

R¹ is Cl, R² is F, R³ is Cl

| | |
|---|---|
| CH₂CH₂SMe | CH(Me)C(O)NH(Et) |
| CH₂CH₂SEt | CH(Me)C(O)NH(n-Pr) |
| CH₂CH₂S(n-Pr) | CH(Me)C(O)NH(i-Pr) |
| CH₂CH₂CH₂SMe | CH(Me)C(O)NH(i-Bu) |
| CH₂CH₂CH₂SEt | CH(Me)C(O)NH(s-Bu) |
| CH₂CH₂S(O)Me | CH₂(4-thiazolyl) |
| CH₂CH₂S(O)Et | CH₂C(O)N(Me)CH₂CF₃ |
| CH₂CH₂S(O)(n-Pr) | CH(Me)C(O)N(Me)CH₂CF₃ |
| CH₂CH₂CH₂S(O)Me | CH₂C(O)NH(c-Pr) |
| CH2CH₂CH₂S(O)Et | CH₂C(O)NH(CH₂-c-Pr) |
| CH₂CH₂SO₂Me | CH₂C(O)NHCH₂CH₂Cl |
| CH₂CH₂SO₂Et | CH₂C(O)NHCH₂CHF₂ |
| CH₂CH₂SO₂(n-Pr) | CH₂C(O)NHCH₂CF₃ |
| CH₂CH₂CH₂ SO₂Me | CH₂C(O)NHCH₂CH₂CF₃ |
| CH₂CH₂CH₂ SO₂Et | CH₂C(O)NHCH(Me)CF₃ |
| CH₂(2-pyridinyl) | CH₂C(O)NHCH₂CH(Me)CF₃ |
| CH₂C(O)NH₂ | CH(Me)C(O)NH(c-Pr) |
| CH₂C(O)NH(Me) | CH(Me)C(O)NH(CH₂-c-Pr) |
| CH₂C(O)NH(Et) | CH(Me)C(O)NHCH₂CH₂Cl |
| CH₂C(O)NH(n-Pr) | CH(Me)C(O)NHCH₂CHF₂ |
| CH₂C(O)NH(i-Pr) | CH(Me)C(O)NHCH₂CF₃ |
| CH₂C(O)NH(i-Bu) | CH(Me)C(O)NHCH₂CH₂CF₃ |
| CH₂C(O)NH(s-Bu) | CH(Me)C(O)NHCH(Me)CF₃ |
| CH(Me)C(O)NH(Me) | CH(Me)C(O)NHCH₂CH(Me)CF₃ |

R¹ is Cl, R² is CN, R³ is Cl

| | |
|---|---|
| CH₂CH₂SMe | CH(Me)C(O)NH(Et) |
| CH₂CH₂SEt | CH(Me)C(O)NH(n-Pr) |
| CH₂CH₂S(n-Pr) | CH(Me)C(O)NH(i-Pr) |
| CH₂CH₂CH₂SMe | CH(Me)C(O)NH(i-Bu) |
| CH₂CH₂CH₂SEt | CH(Me)C(O)NH(s-Bu) |
| CH₂CH₂S(O)Me | CH₂(4-thiazolyl) |
| CH₂CH₂S(O)Et | CH₂C(O)N(Me)CH₂CF₃ |
| CH₂CH₂S(O)(n-Pr) | CH(Me)C(O)N(Me)CH₂CF₃ |
| CH₂CH₂CH₂S(O)Me | CH₂C(O)NH(c-Pr) |
| CH2CH₂CH₂S(O)Et | CH₂C(O)NH(CH₂-c-Pr) |
| CH₂CH₂SO₂Me | CH₂C(O)NHCH₂CH₂Cl |
| CH₂CH₂SO₂Et | CH₂C(O)NHCH₂CHF₂ |
| CH₂CH₂SO₂(n-Pr) | CH₂C(O)NHCH₂CF₃ |
| CH₂CH₂CH₂ SO₂Me | CH₂C(O)NHCH₂CH₂CF₃ |
| CH₂CH₂CH₂ SO₂Et | CH₂C(O)NHCH(Me)CF₃ |
| CH₂(2-pyridinyl) | CH₂C(O)NHCH₂CH(Me)CF₃ |
| CH₂C(O)NH₂ | CH(Me)C(O)NH(c-Pr) |
| CH₂C(O)NH(Me) | CH(Me)C(O)NH(CH₂-c-Pr) |
| CH₂C(O)NH(Et) | CH(Me)C(O)NHCH₂CH₂Cl |
| CH₂C(O)NH(n-Pr) | CH(Me)C(O)NHCH₂CHF₂ |
| CH₂C(O)NH(i-Pr) | CH(Me)C(O)NHCH₂CF₃ |
| CH₂C(O)NH(i-Bu) | CH(Me)C(O)NHCH₂CH₂CF₃ |
| CH₂C(O)NH(s-Bu) | CH(Me)C(O)NHCH(Me)CF₃ |
| CH(Me)C(O)NH(Me) | CH(Me)C(O)NHCH₂CH(Me)CF₃ |

R¹ is Br, R² is H, R³ is H

| | |
|---|---|
| CH₂CH₂SMe | CH(Me)C(O)NH(Et) |
| CH₂CH₂SEt | CH(Me)C(O)NH(n-Pr) |
| CH₂CH₂S(n-Pr) | CH(Me)C(O)NH(i-Pr) |
| CH₂CH₂CH₂SMe | CH(Me)C(O)NH(i-Bu) |

TABLE 2-continued

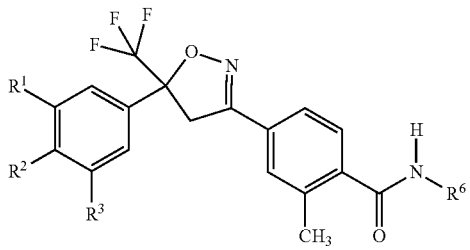

R⁶

| | |
|---|---|
| CH₂CH₂CH₂SEt | CH(Me)C(O)NH(s-Bu) |
| CH₂CH₂S(O)Me | CH₂(4-thiazolyl) |
| CH₂CH₂S(O)Et | CH₂C(O)N(Me)CH₂CF₃ |
| CH₂CH₂S(O)(n-Pr) | CH(Me)C(O)N(Me)CH₂CF₃ |
| CH₂CH₂CH₂S(O)Me | CH₂C(O)NH(c-Pr) |
| CH2CH₂CH₂S(O)Et | CH₂C(O)NH(CH₂-c-Pr) |
| CH₂CH₂SO₂Me | CH₂C(O)NHCH₂CH₂Cl |
| CH₂CH₂SO₂Et | CH₂C(O)NHCH₂CHF₂ |
| CH₂CH₂SO₂(n-Pr) | CH₂C(O)NHCH₂CF₃ |
| CH₂CH₂CH₂ SO₂Me | CH₂C(O)NHCH₂CH₂CF₃ |
| CH₂CH₂CH₂ SO₂Et | CH₂C(O)NHCH(Me)CF₃ |
| CH₂(2-pyridinyl) | CH₂C(O)NHCH₂CH(Me)CF₃ |
| CH₂C(O)NH₂ | CH(Me)C(O)NH(c-Pr) |
| CH₂C(O)NH(Me) | CH(Me)C(O)NH(CH₂-c-Pr) |
| CH₂C(O)NH(Et) | CH(Me)C(O)NHCH₂CH₂Cl |
| CH₂C(O)NH(n-Pr) | CH(Me)C(O)NHCH₂CHF₂ |
| CH₂C(O)NH(i-Pr) | CH(Me)C(O)NHCH₂CF₃ |
| CH₂C(O)NH(i-Bu) | CH(Me)C(O)NHCH₂CH₂CF₃ |
| CH₂C(O)NH(s-Bu) | CH(Me)C(O)NHCH(Me)CF₃ |
| CH(Me)C(O)NH(Me) | CH(Me)C(O)NHCH₂CH(Me)CF₃ |

R¹ is Br, R² is H, R³ is Cl

| | |
|---|---|
| CH₂CH₂SMe | CH(Me)C(O)NH(Et) |
| CH₂CH₂SEt | CH(Me)C(O)NH(n-Pr) |
| CH₂CH₂S(n-Pr) | CH(Me)C(O)NH(i-Pr) |
| CH₂CH₂CH₂SMe | CH(Me)C(O)NH(i-Bu) |
| CH₂CH₂CH₂SEt | CH(Me)C(O)NH(s-Bu) |
| CH₂CH₂S(O)Me | CH₂(4-thiazolyl) |
| CH₂CH₂S(O)Et | CH₂C(O)N(Me)CH₂CF₃ |
| CH₂CH₂S(O)(n-Pr) | CH(Me)C(O)N(Me)CH₂CF₃ |
| CH₂CH₂CH₂S(O)Me | CH₂C(O)NH(c-Pr) |
| CH2CH₂CH₂S(O)Et | CH₂C(O)NH(CH₂-c-Pr) |
| CH₂CH₂SO₂Me | CH₂C(O)NHCH₂CH₂Cl |
| CH₂CH₂SO₂Et | CH₂C(O)NHCH₂CHF₂ |
| CH₂CH₂SO₂(n-Pr) | CH₂C(O)NHCH₂CF₃ |
| CH₂CH₂CH₂ SO₂Me | CH₂C(O)NHCH₂CH₂CF₃ |
| CH₂CH₂CH₂ SO₂Et | CH₂C(O)NHCH(Me)CF₃ |
| CH₂(2-pyridinyl) | CH₂C(O)NHCH₂CH(Me)CF₃ |
| CH₂C(O)NH₂ | CH(Me)C(O)NH(c-Pr) |
| CH₂C(O)NH(Me) | CH(Me)C(O)NH(CH₂-c-Pr) |
| CH₂C(O)NH(Et) | CH(Me)C(O)NHCH₂CH₂Cl |
| CH₂C(O)NH(n-Pr) | CH(Me)C(O)NHCH₂CHF₂ |
| CH₂C(O)NH(i-Pr) | CH(Me)C(O)NHCH₂CF₃ |
| CH₂C(O)NH(i-Bu) | CH(Me)C(O)NHCH₂CH₂CF₃ |
| CH₂C(O)NH(s-Bu) | CH(Me)C(O)NHCH(Me)CF₃ |
| CH(Me)C(O)NH(Me) | CH(Me)C(O)NHCH₂CH(Me)CF₃ |

R¹ is Br, R² is F, R³ is Br

| | |
|---|---|
| CH₂CH₂SMe | CH(Me)C(O)NH(Et) |
| CH₂CH₂SEt | CH(Me)C(O)NH(n-Pr) |
| CH₂CH₂S(n-Pr) | CH(Me)C(O)NH(i-Pr) |
| CH₂CH₂CH₂SMe | CH(Me)C(O)NH(i-Bu) |
| CH₂CH₂CH₂SEt | CH(Me)C(O)NH(s-Bu) |
| CH₂CH₂S(O)Me | CH₂(4-thiazolyl) |
| CH₂CH₂S(O)Et | CH₂C(O)N(Me)CH₂CF₃ |
| CH₂CH₂S(O)(n-Pr) | CH(Me)C(O)N(Me)CH₂CF₃ |
| CH₂CH₂CH₂S(O)Me | CH₂C(O)NH(c-Pr) |
| CH2CH₂CH₂S(O)Et | CH₂C(O)NH(CH₂-c-Pr) |
| CH₂CH₂SO₂Me | CH₂C(O)NHCH₂CH₂Cl |
| CH₂CH₂SO₂Et | CH₂C(O)NHCH₂CHF₂ |
| CH₂CH₂SO₂(n-Pr) | CH₂C(O)NHCH₂CF₃ |
| CH₂CH₂CH₂ SO₂Me | CH₂C(O)NHCH₂CH₂CF₃ |
| CH₂CH₂CH₂ SO₂Et | CH₂C(O)NHCH(Me)CF₃ |
| CH₂(2-pyridinyl) | CH₂C(O)NHCH₂CH(Me)CF₃ |
| CH₂C(O)NH₂ | CH(Me)C(O)NH(c-Pr) |

TABLE 2-continued

Structure: Isoxazoline with CF$_3$ group, R$^1$, R$^2$, R$^3$ on phenyl ring, and N-R$^6$ benzamide with CH$_3$ substituent.

R$^6$

| | |
|---|---|
| CH$_2$C(O)NH(Me) | CH(Me)C(O)NH(CH$_2$-c-Pr) |
| CH$_2$C(O)NH(Et) | CH(Me)C(O)NHCH$_2$Cl |
| CH$_2$C(O)NH(n-Pr) | CH(Me)C(O)NHCH$_2$CHF$_2$ |
| CH$_2$C(O)NH(i-Pr) | CH(Me)C(O)NHCH$_2$CF$_3$ |
| CH$_2$C(O)NH(i-Bu) | CH(Me)C(O)NHCH$_2$CH$_2$CF$_3$ |
| CH$_2$C(O)NH(s-Bu) | CH(Me)C(O)NHCH(Me)CF$_3$ |
| CH(Me)C(O)NH(Me) | CH(Me)C(O)NHCH$_2$CH(Me)CF$_3$ |

R$^1$ is Br, R$^2$ is Cl, R$^3$ is Cl

| | |
|---|---|
| CH$_2$CH$_2$SMe | CH(Me)C(O)NH(Et) |
| CH$_2$CH$_2$SEt | CH(Me)C(O)NH(n-Pr) |
| CH$_2$CH$_2$S(n-Pr) | CH(Me)C(O)NH(i-Pr) |
| CH$_2$CH$_2$CH$_2$SMe | CH(Me)C(O)NH(i-Bu) |
| CH$_2$CH$_2$CH$_2$SEt | CH(Me)C(O)NH(s-Bu) |
| CH$_2$CH$_2$S(O)Me | CH$_2$(4-thiazolyl) |
| CH$_2$CH$_2$S(O)Et | CH$_2$C(O)N(Me)CH$_2$CF$_3$ |
| CH$_2$CH$_2$S(O)(n-Pr) | CH(Me)C(O)N(Me)CH$_2$CF$_3$ |
| CH$_2$CH$_2$CH$_2$S(O)Me | CH$_2$C(O)NH(c-Pr) |
| CH2CH$_2$CH$_2$S(O)Et | CH$_2$C(O)NH(CH$_2$-c-Pr) |
| CH$_2$CH$_2$SO$_2$Me | CH$_2$C(O)NHCH$_2$Cl |
| CH$_2$CH$_2$SO$_2$Et | CH$_2$C(O)NHCH$_2$CHF$_2$ |
| CH$_2$CH$_2$SO$_2$(n-Pr) | CH$_2$C(O)NHCH$_2$CF$_3$ |
| CH$_2$CH$_2$CH$_2$ SO$_2$Me | CH$_2$C(O)NHCH$_2$CH$_2$CF$_3$ |
| CH$_2$CH$_2$CH$_2$ SO$_2$Et | CH$_2$C(O)NHCH(Me)CF$_3$ |
| CH$_2$(2-pyridinyl) | CH$_2$C(O)NHCH$_2$CH(Me)CF$_3$ |
| CH$_2$C(O)NH$_2$ | CH(Me)C(O)NH(c-Pr) |
| CH$_2$C(O)NH(Me) | CH(Me)C(O)NH(CH$_2$-c-Pr) |
| CH$_2$C(O)NH(Et) | CH(Me)C(O)NHCH$_2$Cl |
| CH$_2$C(O)NH(n-Pr) | CH(Me)C(O)NHCH$_2$CHF$_2$ |
| CH$_2$C(O)NH(i-Pr) | CH(Me)C(O)NHCH$_2$CF$_3$ |
| CH$_2$C(O)NH(i-Bu) | CH(Me)C(O)NHCH$_2$CH$_2$CF$_3$ |
| CH$_2$C(O)NH(s-Bu) | CH(Me)C(O)NHCH(Me)CF$_3$ |
| CH(Me)C(O)NH(Me) | CH(Me)C(O)NHCH$_2$CH(Me)CF$_3$ |

R$^1$ is Br, R$^2$ is Cl, R$^3$ is Br

| | |
|---|---|
| CH$_2$CH$_2$SMe | CH(Me)C(O)NH(Et) |
| CH$_2$CH$_2$SEt | CH(Me)C(O)NH(n-Pr) |
| CH$_2$CH$_2$S(n-Pr) | CH(Me)C(O)NH(i-Pr) |
| CH$_2$CH$_2$CH$_2$SMe | CH(Me)C(O)NH(i-Bu) |
| CH$_2$CH$_2$CH$_2$SEt | CH(Me)C(O)NH(s-Bu) |
| CH$_2$CH$_2$S(O)Me | CH$_2$(4-thiazolyl) |
| CH$_2$CH$_2$S(O)Et | CH$_2$C(O)N(Me)CH$_2$CF$_3$ |
| CH$_2$CH$_2$S(O)(n-Pr) | CH(Me)C(O)N(Me)CH$_2$CF$_3$ |
| CH$_2$CH$_2$CH$_2$S(O)Me | CH$_2$C(O)NH(c-Pr) |
| CH2CH$_2$CH$_2$S(O)Et | CH$_2$C(O)NH(CH$_2$-c-Pr) |
| CH$_2$CH$_2$SO$_2$Me | CH$_2$C(O)NHCH$_2$Cl |
| CH$_2$CH$_2$SO$_2$Et | CH$_2$C(O)NHCH$_2$CHF$_2$ |
| CH$_2$CH$_2$SO$_2$(n-Pr) | CH$_2$C(O)NHCH$_2$CF$_3$ |
| CH$_2$CH$_2$CH$_2$ SO$_2$Me | CH$_2$C(O)NHCH$_2$CH$_2$CF$_3$ |
| CH$_2$CH$_2$CH$_2$ SO$_2$Et | CH$_2$C(O)NHCH(Me)CF$_3$ |
| CH$_2$(2-pyridinyl) | CH$_2$C(O)NHCH$_2$CH(Me)CF$_3$ |
| CH$_2$C(O)NH$_2$ | CH(Me)C(O)NH(c-Pr) |
| CH$_2$C(O)NH(Me) | CH(Me)C(O)NH(CH$_2$-c-Pr) |
| CH$_2$C(O)NH(Et) | CH(Me)C(O)NHCH$_2$Cl |
| CH$_2$C(O)NH(n-Pr) | CH(Me)C(O)NHCH$_2$CHF$_2$ |
| CH$_2$C(O)NH(i-Pr) | CH(Me)C(O)NHCH$_2$CF$_3$ |
| CH$_2$C(O)NH(i-Bu) | CH(Me)C(O)NHCH$_2$CH$_2$CF$_3$ |
| CH$_2$C(O)NH(s-Bu) | CH(Me)C(O)NHCH(Me)CF$_3$ |
| CH(Me)C(O)NH(Me) | CH(Me)C(O)NHCH$_2$CH(Me)CF$_3$ |

R$^1$ is OCF$_3$, R$^2$ is H, R$^3$ is Br

| | |
|---|---|
| CH$_2$CH$_2$SMe | CH(Me)C(O)NH(Et) |
| CH$_2$CH$_2$SEt | CH(Me)C(O)NH(n-Pr) |
| CH$_2$CH$_2$S(n-Pr) | CH(Me)C(O)NH(i-Pr) |
| CH$_2$CH$_2$CH$_2$SMe | CH(Me)C(O)NH(i-Bu) |
| CH$_2$CH$_2$CH$_2$SEt | CH(Me)C(O)NH(s-Bu) |
| CH$_2$CH$_2$S(O)Me | CH$_2$(4-thiazolyl) |
| CH$_2$CH$_2$S(O)Et | CH$_2$C(O)N(Me)CH$_2$CF$_3$ |
| CH$_2$CH$_2$S(O)(n-Pr) | CH(Me)C(O)N(Me)CH$_2$CF$_3$ |
| CH$_2$CH$_2$CH$_2$S(O)Me | CH$_2$C(O)NH(c-Pr) |
| CH2CH$_2$CH$_2$S(O)Et | CH$_2$C(O)NH(CH$_2$-c-Pr) |
| CH$_2$CH$_2$SO$_2$Me | CH$_2$C(O)NHCH$_2$Cl |
| CH$_2$CH$_2$SO$_2$Et | CH$_2$C(O)NHCH$_2$CHF$_2$ |
| CH$_2$CH$_2$SO$_2$(n-Pr) | CH$_2$C(O)NHCH$_2$CF$_3$ |
| CH$_2$CH$_2$CH$_2$ SO$_2$Me | CH$_2$C(O)NHCH$_2$CH$_2$CF$_3$ |
| CH$_2$CH$_2$CH$_2$ SO$_2$Et | CH$_2$C(O)NHCH(Me)CF$_3$ |
| CH$_2$(2-pyridinyl) | CH$_2$C(O)NHCH$_2$CH(Me)CF$_3$ |
| CH$_2$C(O)NH$_2$ | CH(Me)C(O)NH(c-Pr) |
| CH$_2$C(O)NH(Me) | CH(Me)C(O)NH(CH$_2$-c-Pr) |
| CH$_2$C(O)NH(Et) | CH(Me)C(O)NHCH$_2$Cl |
| CH$_2$C(O)NH(n-Pr) | CH(Me)C(O)NHCH$_2$CHF$_2$ |
| CH$_2$C(O)NH(i-Pr) | CH(Me)C(O)NHCH$_2$CF$_3$ |
| CH$_2$C(O)NH(i-Bu) | CH(Me)C(O)NHCH$_2$CH$_2$CF$_3$ |
| CH$_2$C(O)NH(s-Bu) | CH(Me)C(O)NHCH(Me)CF$_3$ |
| CH(Me)C(O)NH(Me) | CH(Me)C(O)NHCH$_2$CH(Me)CF$_3$ |

TABLE 3

Structure: Isoxazoline with CF$_3$ group, R$^1$ and R$^3$ on phenyl ring, and N-R$^6$ benzamide with CH$_3$ substituent.

R$^6$

R$^1$ is Cl, R$^3$ is Cl

| | |
|---|---|
| CH$_2$CH$_2$OH | CH$_2$C(O)NHCH$_2$CH(Me)CF$_3$ |
| CH$_2$CH$_2$OMe | CH$_2$C(O)NH(CH$_2$)$_2$CF$_2$CF$_3$ |
| CH$_2$CH$_2$OEt | CH$_2$C(O)NHCH$_2$(CF$_2$)$_2$CF$_3$ |
| CH$_2$CH$_2$O(i-Pr) | CH(Me)C(O)NHCH$_2$F |
| CH$_2$CH(Me)OH | CH(Me)C(O)NHCH$_2$Cl |
| CH$_2$CH(CF$_3$)OH | CH(Me)C(O)NHCH$_2$CHF$_2$ |
| CH$_2$C(Me)$_2$OH | CH(Me)C(O)NHCH$_2$CF$_3$ |
| CH$_2$C(CF$_3$)(Me)OH | CH(Me)C(O)NHCH$_2$CH(Me)F |
| CH(Me)CH$_2$OH | CH(Me)C(O)NHCH$_2$C(Me)$_2$F |
| C(Me)$_2$CH$_2$OH | CH(Me)C(O)NH(CH$_2$)$_2$CH$_2$F |
| CH(Et)CH$_2$OH | CH(Me)C(O)NHCH$_2$CH$_2$CF$_3$ |
| CH(i-Pr)CH$_2$OH | CH(Me)C(O)NHCH$_2$CHFCF$_3$ |
| CH(i-Bu)CH$_2$OH | CH(Me)C(O)NHCH$_2$CF$_2$CF$_3$ |
| CH(Me)CH(CF$_3$)OH | CH(Me)C(O)NHCH(Me)CF$_3$ |
| CH$_2$CH$_2$CH$_2$OH | CH(Me)C(O)NHCH(CF$_3$)$_2$ |
| CH$_2$CH$_2$CH$_2$OMe | CH(Me)C(O)NHC(Me)$_2$CF$_3$ |
| CH$_2$CH$_2$CH$_2$OEt | CH(Me)C(O)NHCH$_2$CH(Me)CF$_3$ |
| CH$_2$CH$_2$CH(CF$_3$)OH | CH(Me)C(O)NH(CH$_2$)$_2$CF$_2$CF$_3$ |
| CH(Me)CH$_2$CH$_2$OH | CH(Me)C(O)NHCH$_2$(CF$_2$)$_2$CF$_3$ |
| CH$_2$CH(Me)CH$_2$OH | C(Me)$_2$C(O)NHCH$_2$F |
| CH$_2$C(Me)$_2$CH$_2$OH | C(Me)$_2$C(O)NHCH$_2$Cl |
| CH$_2$CH$_2$CH(Me)OH | C(Me)$_2$C(O)NHCH$_2$CHF$_2$ |
| CH$_2$CH$_2$C(Me)$_2$OH | C(Me)$_2$C(O)NHCH$_2$CF$_3$ |

TABLE 3-continued

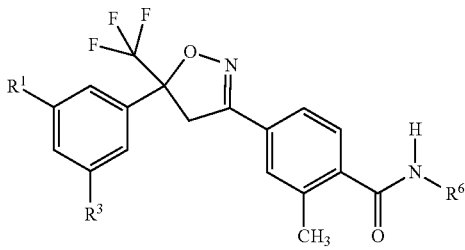

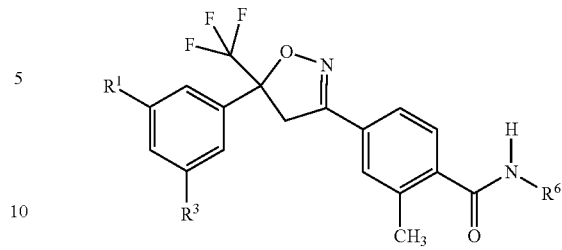

| R6 | |
|---|---|
| CH2CH2SMe | C(Me)2C(O)NHCH2CH(Me)F |
| CH2CH2SEt | C(Me)2C(O)NHCH2C(Me)2F |
| CH2CH2S(n-Pr) | C(Me)2C(O)NH(CH2)2CH2F |
| CH2CH2S(i-Pr) | C(Me)2C(O)NH(CH2)2CH2F |
| CH2CH2S(i-Bu) | C(Me)2C(O)NHCH2CH2CF3 |
| CH2CH(Me)SMe | C(Me)2C(O)NHCH2CHFCF3 |
| CH2CH(CF3)SMe | C(Me)2C(O)NHCH2CF2CF3 |
| CH2C(Me)2SMe | CH2C(O)NH(c-Pr) |
| CH(Me)CH2SMe | CH2C(O)NH(CH2-c-Pr) |
| C(Me)2CH2SMe | CH2(4-thiazolyl) |
| CH(Et)CH2SMe | CH2C(O)NH(Me) |
| CH(i-Pr)CH2SMe | CH2C(O)NH(Et) |
| CH(i-Bu)CH2SMe | CH2C(O)NH(n-Pr) |
| CH2CH2CH2SMe | CH2C(O)NH(i-Pr) |
| CH2CH2CH2SEt | CH2C(O)NH(n-Bu) |
| CH2CH2CH(Me)SMe | CH2C(O)NH(i-Bu) |
| CH2CH2CH(CF3)SMe | CH2C(O)NH(s-Bu) |
| CH(Me)CH2CH2SMe | CH2C(O)NMe2 |
| CH(Et)CH2CH2SMe | CH2C(O)NMe(Et) |
| CH2CH(Me)CH2SMe | CH2C(O)NEt2 |
| CH2C(Me)2CH2SMe | CH2C(O)NMe(n-Pr) |
| CH2CH2S(O)Me | CH2C(O)NMe(i-Pr) |
| CH2CH2S(O)Et | CH2C(O)NMe(s-Bu) |
| CH2CH2S(O)(n-Pr) | CH(Me)C(O)NH(Me) |
| CH2CH2S(O)(i-Pr) | CH(Me)C(O)NH(Et) |
| CH2CH2S(O)(i-Bu) | CH(Me)C(O)NH(i-Pr) |
| CH2CH(Me)S(O)Me | CH(Me)C(O)NH(n-Bu) |
| CH2CH(CF3)S(O)Me | CH(Me)C(O)NH(i-Bu) |
| CH2C(Me)2S(O)Me | CH(Me)C(O)NH(s-Bu) |
| CH(Me)CH2S(O)Me | C(Me)2C(O)NH(Me) |
| CH(Et)CH2S(O)Me | C(Me)2C(O)NH(Et) |
| CH(i-Bu)CH2S(O)Me | C(Me)2C(O)NH(n-Pr) |
| CH2CH2CH2S(O)Me | C(Me)2C(O)NH(i-Pr) |
| CH2CH2CH2S(O)Et | C(Me)2C(O)NH(n-Bu) |
| CH2CH2CH2S(O)(i-Bu) | C(Me)2C(O)NH(i-Bu) |
| CH2CH2CH(Me)S(O)Me | C(Me)2C(O)NH(s-Bu) |
| CH2CH2CH(CF3)S(O)Me | CH2C(O)N(Me)CH2CH2F |
| CH(Me)CH2CH2S(O)Me | CH2C(O)N(Me)CH2CH2Cl |
| CH(Et)CH2CH2S(O)Me | CH2C(O)N(Me)CH2CHF2 |
| CH2CH(Me)CH2S(O)Me | CH2C(O)N(Me)CH2CF3 |
| CH2C(Me)2CH2S(O)Me | CH2C(O)N(Me)CH2CH2CH2F |
| CH2(2-pyridinyl) | CH2C(O)N(Me)CH2CH2CF3 |
| CH2CH2SO2Me | CH2C(O)N(Me)CH2CF2CF3 |
| CH2CH2SO2Et | CH2C(O)N(Me)CH(Me)CF3 |
| CH2CH2SO2(n-Pr) | CH2C(O)N(Me)CH(CF3)2 |
| CH2CH2SO2(i-Pr) | CH2C(O)N(Me)C(Me)2CF3 |
| CH2CH(Me)SO2Me | CH(Me)C(O)N(Me)CH2CH2F |
| CH2CH(CF3)SO2Me | CH(Me)C(O)N(Me)CH2CH2Cl |
| CH2C(Me)2SO2Me | CH(Me)C(O)N(Me)CH2CHF2 |
| CH(Me)CH2SO2Me | CH(Me)C(O)N(Me)CH2CF3 |
| C(Me)2CH2SO2Me | CH(Me)C(O)N(Me)(CH2)2CH2F |
| CH(Et)CH2SO2Me | CH(Me)C(O)N(Me)CH2CH2CF3 |
| CH(i-Pr)CH2SO2Me | CH(Me)C(O)N(Me)CH2CF2CF3 |
| CH(i-Bu)CH2SO2Me | CH(Me)C(O)N(Me)CH(Me)CF3 |
| CH2CH2CH2SO2Me | CH(Me)C(O)N(Me)CH(CF3)2 |
| CH2CH2CH2SO2Et | CH(Me)C(O)N(Me)C(Me)2CF3 |
| CH2CH2CH(Me)SO2Me | C(Me)2C(O)N(Me)CH2CH2F |
| CH2CH2CH(CF3)SO2Me | C(Me)2C(O)N(Me)CH2CH2Cl |
| CH(Me)CH2CH2SO2Me | C(Me)2C(O)N(Me)CH2CHF2 |
| CH(Et)CH2CH2SO2Me | C(Me)2C(O)N(Me)CH2CF3 |
| CH2CH(Me)CH2SO2Me | C(Me)2C(O)N(Me)CH2CH2CH2F |
| CH2C(Me)2CH2SO2Me | C(Me)2C(O)N(Me)CH2CH2CF3 |
| CH2C(O)NHCH2CH2F | C(Me)2C(O)N(Me)CH2CF2CF3 |
| CH2C(O)NHCH2CH2Cl | C(Me)2C(O)N(Me)CH(Me)CF3 |
| CH2C(O)NHCH2CHF2 | C(Me)2C(O)N(Me)CH(CF3)2 |

| R6 | |
|---|---|
| CH2C(O)NHCH2CF3 | C(Me)2C(O)N(Me)C(Me)2CF3 |
| CH2C(O)NHCH2CH(Me)F | C(Me)2C(O)NHCH(Me)CF3 |
| CH2C(O)NHCH2C(Me)2F | C(Me)2C(O)NHCH(CF3)2 |
| CH2C(O)NH(CH2)2CH2F | C(Me)2C(O)NHC(Me)2CF3 |
| CH2C(O)NH(CH2)2CH2F | C(Me)2C(O)NHCH2CH(Me)CF3 |
| CH2C(O)NHCH2CH2CF3 | C(Me)2C(O)NH(CH2)2CF2CF3 |
| CH2C(O)NHCH2CHFCF3 | C(Me)2C(O)NHCH2(CF2)2CF3 |
| CH2C(O)NHCH2CF2CF3 | C(Me)2C(O)NHCH(i-Pr)CF3 |
| CH2C(O)NHCH(Me)CF3 | CH(Me)C(O)NH(c-Pr) |
| CH2C(O)NHCH(CF3)2 | CH(Me)C(O)NH(CH2-c-Pr) |
| CH2C(O)NHC(Me)2CF3 | |

R1 is Br, R3 is Br

| | |
|---|---|
| CH2CH2OH | CH2C(O)NHCH2CH(Me)CF3 |
| CH2CH2OMe | CH2C(O)NH(CH2)2CF2CF3 |
| CH2CH2OEt | CH2C(O)NHCH2(CF2)2CF3 |
| CH2CH2O(i-Pr) | CH(Me)C(O)NHCH2CH2F |
| CH2CH(Me)OH | CH(Me)C(O)NHCH2CH2Cl |
| CH2CH(CF3)OH | CH(Me)C(O)NHCH2CHF2 |
| CH2C(Me)2OH | CH(Me)C(O)NHCH2CF3 |
| CH2C(CF3)(Me)OH | CH(Me)C(O)NHCH2CH(Me)F |
| CH(Me)CH2OH | CH(Me)C(O)NHCH2C(Me)2F |
| C(Me)2CH2OH | CH(Me)C(O)NH(CH2)2CH2F |
| CH(Et)CH2OH | CH(Me)C(O)NHCH2CH2CF3 |
| CH(i-Pr)CH2OH | CH(Me)C(O)NHCH2CHFCF3 |
| CH(i-Bu)CH2OH | CH(Me)C(O)NHCH2CF2CF3 |
| CH(Me)CH(CF3)OH | CH(Me)C(O)NHCH(Me)CF3 |
| CH2CH2CH2OH | CH(Me)C(O)NHCH(CF3)2 |
| CH2CH2CH2OMe | CH(Me)C(O)NHC(Me)2CF3 |
| CH2CH2CH2OEt | CH(Me)C(O)NHCH2CH(Me)CF3 |
| CH2CH2CH(CF3)OH | CH(Me)C(O)NH(CH2)2CF2CF3 |
| CH(Me)CH2CH2OH | CH(Me)C(O)NHCH2(CF2)2CF3 |
| CH2CH(Me)CH2OH | C(Me)2C(O)NHCH2CH2F |
| CH2C(Me)2CH2OH | C(Me)2C(O)NHCH2CH2Cl |
| CH2CH2CH(Me)OH | C(Me)2C(O)NHCH2CHF2 |
| CH2C(Me)2CH2OH | C(Me)2C(O)NHCH2CF3 |
| CH2CH2SMe | C(Me)2C(O)NHCH2CH(Me)F |
| CH2CH2SEt | C(Me)2C(O)NHCH2C(Me)2F |
| CH2CH2S(n-Pr) | C(Me)2C(O)NH(CH2)2CH2F |
| CH2CH2S(i-Pr) | C(Me)2C(O)NHCH2CH2CF3 |
| CH2CH2S(i-Bu) | C(Me)2C(O)NHCH2CHFCF3 |
| CH2CH(Me)SMe | C(Me)2C(O)NHCH2CF2CF3 |
| CH2CH(CF3)SMe | CH2C(O)NH(c-Pr) |
| CH2C(Me)2SMe | CH2C(O)NH(CH2-c-Pr) |
| CH(Me)CH2SMe | CH2(4-thiazolyl) |
| C(Me)2CH2SMe | CH2C(O)NH(Me) |
| CH(Et)CH2SMe | CH2C(O)NH(Et) |
| CH(i-Pr)CH2SMe | CH2C(O)NH(n-Pr) |
| CH(i-Bu)CH2SMe | CH2C(O)NH(i-Pr) |
| CH2CH2CH2SMe | CH2C(O)NH(n-Bu) |
| CH2CH2CH2SEt | CH2C(O)NH(i-Bu) |
| CH2CH2CH(Me)SMe | CH2C(O)NH(s-Bu) |
| CH2CH2CH(CF3)SMe | CH2C(O)NMe2 |
| CH(Me)CH2CH2SMe | CH2C(O)NMe(Et) |
| CH(Et)CH2CH2SMe | CH2C(O)NEt2 |
| CH2CH(Me)CH2SMe | CH2C(O)NMe(n-Pr) |
| CH2C(Me)2CH2SMe | CH2C(O)NMe(i-Pr) |
| CH2CH2S(O)Me | CH2C(O)NMe(s-Bu) |
| CH2CH2S(O)Et | CH(Me)C(O)NH(Me) |
| CH2CH2S(O)(n-Pr) | CH(Me)C(O)NH(Et) |
| CH2CH2S(O)(i-Pr) | CH(Me)C(O)NH(n-Pr) |
| CH2CH2S(O)(i-Bu) | CH(Me)C(O)NH(i-Pr) |
| CH2CH(Me)S(O)Me | CH(Me)C(O)NH(n-Bu) |
| CH2CH(CF3)S(O)Me | CH(Me)C(O)NH(i-Bu) |
| CH2C(Me)2S(O)Me | CH(Me)C(O)NH(s-Bu) |
| CH(Me)CH2S(O)Me | C(Me)2C(O)NH(Me) |

TABLE 3-continued

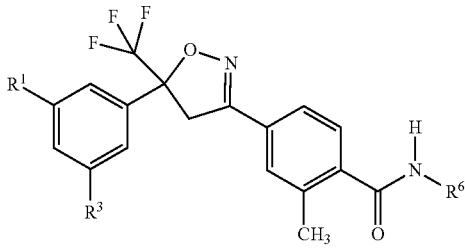

| R⁶ | |
|---|---|
| CH(Et)CH₂S(O)Me | C(Me)₂C(O)NH(Et) |
| CH(i-Bu)CH₂S(O)Me | C(Me)₂C(O)NH(n-Pr) |
| CH₂CH₂CH₂S(O)Me | C(Me)₂C(O)NH(i-Pr) |
| CH₂CH₂CH₂S(O)Et | C(Me)₂C(O)NH(n-Bu) |
| CH₂CH₂CH₂S(O)(i-Bu) | C(Me)₂C(O)NH(i-Bu) |
| CH₂CH₂CH(Me)S(O)Me | C(Me)₂C(O)NH(s-Bu) |
| CH₂CH₂CH(CF₃)S(O)Me | CH₂C(O)N(Me)CH₂CH₂F |
| CH(Me)CH₂CH₂S(O)Me | CH₂C(O)N(Me)CH₂CH₂Cl |
| CH(Et)CH₂CH₂S(O)Me | CH₂C(O)N(Me)CH₂CHF₂ |
| CH₂CH(Me)CH₂S(O)Me | CH₂C(O)N(Me)CH₂CF₃ |
| CH₂C(Me)₂CH₂S(O)Me | CH₂C(O)N(Me)CH₂CH₂CH₂F |
| CH₂(2-pyridinyl) | CH₂C(O)N(Me)CH₂CH₂CF₃ |
| CH₂CH₂SO₂Me | CH₂C(O)N(Me)CH₂CF₂CF₃ |
| CH₂CH₂SO₂Et | CH₂C(O)N(Me)CH(Me)CF₃ |
| CH₂CH₂SO₂(n-Pr) | CH₂C(O)N(Me)CH(CF₃)₂ |
| CH₂CH₂SO₂(i-Pr) | CH₂C(O)N(Me)C(Me)₂CF₃ |
| CH₂CH(Me)SO₂Me | CH(Me)C(O)N(Me)CH₂CH₂F |
| CH₂CH(CF₃)SO₂Me | CH(Me)C(O)N(Me)CH₂CH₂Cl |
| CH₂C(Me)²SO₂Me | CH(Me)C(O)N(Me)CH₂CHF₂ |
| CH(Me)CH₂SO₂Me | CH(Me)C(O)N(Me)CH₂CF₃ |
| C(Me)₂CH₂SO₂Me | CH(Me)C(O)N(Me)CH₂CH₂CH₂F |
| CH(Et)CH₂SO₂Me | CH(Me)C(O)N(Me)CH₂CH₂CF₃ |
| CH(i-Pr)CH₂SO₂Me | CH(Me)C(O)N(Me)CH₂CF₂CF₃ |
| CH(i-Bu)CH₂SO₂Me | CH(Me)C(O)N(Me)CH(Me)CF₃ |
| CH₂CH₂CH₂SO₂Me | CH(Me)C(O)N(Me)CH(CF₃)₂ |
| CH₂CH₂CH₂SO₂Et | CH(Me)C(O)N(Me)C(Me)₂CF₃ |
| CH₂CH₂CH(Me)SO₂Me | C(Me)₂C(O)N(Me)CH₂CH₂F |
| CH₂CH₂CH(CF₃)SO₂Me | C(Me)₂C(O)N(Me)CH₂CH₂Cl |
| CH(Me)CH₂CH₂SO₂Me | C(Me)₂C(O)N(Me)CH₂CHF₂ |
| CH(Et)CH₂CH₂SO₂Me | C(Me)₂C(O)N(Me)CH₂CF₃ |
| CH₂CH(Me)CH₂SO₂Me | C(Me)₂C(O)N(Me)CH₂CH₂CH₂F |
| CH₂C(Me)₂CH₂SO₂Me | C(Me)₂C(O)N(Me)CH₂CH₂CF₃ |
| CH₂C(O)NHCH₂CH₂F | C(Me)₂C(O)N(Me)CH₂CF₂CF₃ |
| CH₂C(O)NHCH₂CH₂Cl | C(Me)₂C(O)N(Me)CH(Me)CF₃ |
| CH₂C(O)NHCH₂CHF₂ | C(Me)₂C(O)N(Me)CH(CF₃)₂ |
| CH₂C(O)NHCH₂CF₃ | C(Me)₂C(O)N(Me)C(Me)₂CF₃ |
| CH₂C(O)NHCH₂CH(Me)F | C(Me)₂C(O)NHCH(Me)CF₃ |
| CH₂C(O)NHCH₂C(Me)₂F | C(Me)₂C(O)NHCH(CF₃)₂ |
| CH₂C(O)NH(CH₂)₂CH₂F | C(Me)₂C(O)NHC(Me)₂CF₃ |
| CH₂C(O)NHCH₂CH₂CF₃ | C(Me)₂C(O)NHCH₂(Me)CF₃ |
| CH₂C(O)NHCH₂CHFCF₃ | C(Me)₂C(O)NH(CH₂)₂CF₂CF₃ |
| CH₂C(O)NHCH₂CF₂CF₃ | C(Me)₂C(O)N(CH₂)₂CF₂CF₃ |
| CH₂C(O)NHCH(Me)CF₃ | C(Me)₂C(O)NHCH(i-Pr)CF₃ |
| CH₂C(O)NHCH(CF₃)₂ | CH(Me)C(O)NH(c-Pr) |
| CH₂C(O)NHC(Me)₂CF₃ | CH(Me)C(O)NH(CH₂-c-Pr) |

R¹ is CF₃, R³ is H

| | |
|---|---|
| CH₂CH₂OH | CH₂C(O)NHCH₂CH(Me)CF₃ |
| CH₂CH₂OMe | CH₂C(O)NH(CH₂)₂CF₂CF₃ |
| CH₂CH₂OEt | CH₂C(O)NH(CH₂)₂CF₂CF₃ |
| CH₂CH₂O(i-Pr) | CH(Me)C(O)NHCH₂CH₂F |
| CH₂CH(Me)OH | CH(Me)C(O)NHCH₂CH₂Cl |
| CH₂CH(CF₃)OH | CH(Me)C(O)NHCH₂CHF₂ |
| CH₂C(Me)₂OH | CH(Me)C(O)NHCH₂CF₃ |
| CH₂C(CF₃)(Me)OH | CH(Me)C(O)NHCH₂CH(Me)F |
| CH(Me)CH₂OH | CH(Me)C(O)NHCH₂C(Me)₂F |
| C(Me)₂CH₂OH | CH(Me)C(O)NH(CH₂)₂CH₂F |
| CH(Et)CH₂OH | CH(Me)C(O)NHCH₂CH₂CF₃ |
| CH(i-Pr)CH₂OH | CH(Me)C(O)NHCH₂CHFCF₃ |
| CH(i-Bu)CH₂OH | CH(Me)C(O)NHCH₂CF₂CF₃ |
| CH(Me)CH(CF₃)OH | CH(Me)C(O)NHCH(Me)CF₃ |
| CH₂CH₂CH₂OH | CH(Me)C(O)NHCH(CF₃)₂ |
| CH₂CH₂CH₂OMe | CH(Me)C(O)NHC(Me)₂CF₃ |
| CH₂CH₂CH₂OEt | CH(Me)C(O)NHCH₂CH(Me)CF₃ |
| CH₂CH₂CH(CF₃)OH | CH(Me)C(O)NH(CH₂)₂CF₂CF₃ |

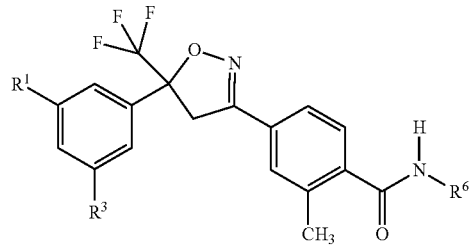

| R⁶ | |
|---|---|
| CH(Me)CH₂CH₂OH | CH(Me)C(O)NHCH₂(CF₂)₂CF₃ |
| CH₂CH(Me)CH₂OH | C(Me)₂C(O)NHCH₂CH₂F |
| CH₂C(Me)₂CH₂OH | C(Me)₂C(O)NHCH₂CH₂Cl |
| CH₂CH₂CH(Me)OH | C(Me)₂C(O)NHCH₂CHF₂ |
| CH₂CH₂C(Me)₂OH | C(Me)₂C(O)NHCH₂CF₃ |
| CH₂CH₂SMe | C(Me)₂C(O)NHCH₂CH(Me)F |
| CH₂CH₂SEt | C(Me)₂C(O)NHCH₂C(Me)₂F |
| CH₂CH₂S(n-Pr) | C(Me)₂C(O)NH(CH₂)₂CH₂F |
| CH₂CH₂S(i-Pr) | C(Me)₂C(O)NHCH₂CH₂CF₃ |
| CH₂CH₂S(i-Bu) | C(Me)₂C(O)NHCH₂CHFCF₃ |
| CH₂CH(Me)SMe | C(Me)₂C(O)NHCH₂CF₂CF₃ |
| CH₂CH(CF₃)SMe | CH₂C(O)NH(c-Pr) |
| CH₂C(Me)₂SMe | CH₂C(O)NH(CH₂-c-Pr) |
| CH(Me)CH₂SMe | CH₂(4-thiazolyl) |
| C(Me)₂CH₂SMe | CH₂C(O)NH(Me) |
| CH(Et)CH₂SMe | CH₂C(O)NH(Et) |
| CH(i-Pr)CH₂SMe | CH₂C(O)NH(n-Pr) |
| CH(i-Bu)CH₂SMe | CH₂C(O)NH(i-Pr) |
| CH₂CH₂CH₂SMe | CH₂C(O)NH(n-Bu) |
| CH₂CH₂CH₂SEt | CH₂C(O)NH(i-Bu) |
| CH₂CH₂CH(CF₃)SMe | CH₂C(O)NH(s-Bu) |
| CH(Me)CH₂CH₂SMe | CH₂C(O)NMe₂ |
| CH(Et)CH₂CH₂SMe | CH₂C(O)NMe(Et) |
| CH₂CH(Me)CH₂SMe | CH₂C(O)NEt₂ |
| CH₂C(Me)₂CH₂SMe | CH₂C(O)NMe(n-Pr) |
| CH₂CH₂S(O)Me | CH₂C(O)NMe(i-Pr) |
| CH₂CH₂S(O)Et | CH₂C(O)NMe(s-Bu) |
| CH₂CH₂S(O)(n-Pr) | CH(Me)C(O)NH(Me) |
| CH₂CH₂S(O)(i-Pr) | CH(Me)C(O)NH(Et) |
| CH₂CH₂S(O)(i-Bu) | CH(Me)C(O)NH(n-Pr) |
| CH₂CH(Me)S(O)Me | CH(Me)C(O)NH(i-Pr) |
| CH₂CH(CF₃)S(O)Me | CH(Me)C(O)NH(n-Bu) |
| CH₂C(Me)₂S(O)Me | CH(Me)C(O)NH(i-Bu) |
| CH(Me)CH₂S(O)Me | CH(Me)C(O)NH(s-Bu) |
| CH(Et)CH₂S(O)Me | C(Me)₂C(O)NH(Me) |
| CH(i-Bu)CH₂S(O)Me | C(Me)₂C(O)NH(Et) |
| CH₂CH₂CH₂S(O)Me | C(Me)₂C(O)NH(n-Pr) |
| CH₂CH₂CH₂S(O)Et | C(Me)₂C(O)NH(i-Pr) |
| CH₂CH₂CH₂S(O)(i-Bu) | C(Me)₂C(O)NH(n-Bu) |
| CH₂CH₂CH(Me)S(O)Me | C(Me)₂C(O)NH(i-Bu) |
| CH₂CH₂CH(CF₃)S(O)Me | C(Me)₂C(O)NH(s-Bu) |
| CH(Me)CH₂CH₂S(O)Me | CH₂C(O)N(Me)CH₂CH₂F |
| CH(Et)CH₂CH₂S(O)Me | CH₂C(O)N(Me)CH₂CH₂Cl |
| CH₂CH(Me)CH₂S(O)Me | CH₂C(O)N(Me)CH₂CHF₂ |
| CH₂C(Me)₂CH₂S(O)Me | CH₂C(O)N(Me)CH₂CF₃ |
| CH₂(2-pyridinyl) | CH₂C(O)N(Me)CH₂CH₂CH₂F |
| CH₂CH₂SO₂Me | CH₂C(O)N(Me)CH₂CH₂CF₃ |
| CH₂CH₂SO₂Et | CH₂C(O)N(Me)CH₂CF₂CF₃ |
| CH₂CH₂SO₂(n-Pr) | CH₂C(O)N(Me)CH(Me)CF₃ |
| CH₂CH₂SO₂(i-Pr) | CH₂C(O)N(Me)CH(CF₃)₂ |
| CH₂CH(Me)SO₂Me | CH₂C(O)N(Me)C(Me)₂CF₃ |
| CH₂CH(CF₃)SO₂Me | CH(Me)C(O)N(Me)CH₂CH₂F |
| CH₂C(Me)²SO₂Me | CH(Me)C(O)N(Me)CH₂CH₂Cl |
| CH(Me)CH₂SO₂Me | CH(Me)C(O)N(Me)CH₂CHF₂ |
| C(Me)₂CH₂SO₂Me | CH(Me)C(O)N(Me)CH₂CF₃ |
| CH(Et)CH₂SO₂Me | CH(Me)C(O)N(Me)(CH₂)₂CH₂F |
| CH(i-Pr)CH₂SO₂Me | CH(Me)C(O)N(Me)CH₂CH₂CF₃ |
| CH(i-Bu)CH₂SO₂Me | CH(Me)C(O)N(Me)CH₂CF₂CF₃ |
| CH₂CH₂CH₂SO₂Me | CH(Me)C(O)N(Me)CH(Me)CF₃ |
| CH₂CH₂CH₂SO₂Et | CH(Me)C(O)N(Me)(CF₃)₂ |
| CH₂CH₂CH(Me)SO₂Me | CH(Me)C(O)N(Me)C(Me)₂CF₃ |
| CH₂CH₂CH(CF₃)SO₂Me | C(Me)₂C(O)N(Me)CH₂CH₂F |
| CH(Me)CH₂CH₂SO₂Me | C(Me)₂C(O)N(Me)CH₂CH₂Cl |
| CH(Et)CH₂CH₂SO₂Me | C(Me)₂C(O)N(Me)CH₂CHF₂ |
| CH₂CH(Me)CH₂SO₂Me | C(Me)₂C(O)N(Me)CH₂CF₃ |

TABLE 3-continued

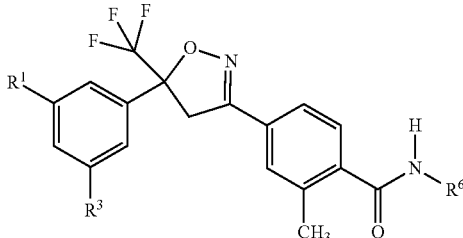

| R6 | |
|---|---|
| CH2CH(Me)CH2SO2Me | C(Me)2C(O)N(Me)CH2CH2CH2F |
| CH2C(Me)2CH2SO2Me | C(Me)2C(O)N(Me)CH2CH2CF3 |
| CH2C(O)NHCH2CH2F | C(Me)2C(O)N(Me)CH2CF2CF3 |
| CH2C(O)NHCH2CH2Cl | C(Me)2C(O)N(Me)CH(Me)CF3 |
| CH2C(O)NHCH2CHF2 | C(Me)2C(O)N(Me)CH(CF3)2 |
| CH2C(O)NHCH2CF3 | C(Me)2C(O)N(Me)C(Me)2CF3 |
| CH2C(O)NHCH2CH(Me)F | C(Me)2C(O)NHCH(Me)CF3 |
| CH2C(O)NHCH2C(Me)2F | C(Me)2C(O)NHCH(CF3)2 |
| CH2C(O)NH(CH2)2CH2F | C(Me)2C(O)NHC(Me)2CF3 |
| CH2C(O)NHCH2CH2CF3 | C(Me)2C(O)NHCH2CH(Me)CF3 |
| CH2C(O)NHCH2CHFCF3 | C(Me)2C(O)NH(CH2)2CF2CF3 |
| CH2C(O)NHCH2CF2CF3 | C(Me)2C(O)NHCH2(CF2)2CF3 |
| CH2C(O)NHCH(Me)CF3 | C(Me)2C(O)NHCH(i-Pr)CF3 |
| CH2C(O)NHCH(CF3)2 | CH(Me)C(O)NH(c-Pr) |
| CH2C(O)NHC(Me)2CF3 | CH(Me)C(O)NH(CH2-c-Pr) |

R1 is CF3, R3 is F

| | |
|---|---|
| CH2CH2OH | CH2C(O)NHCH2CH(Me)CF3 |
| CH2CH2OMe | CH2C(O)NH(CH2)2CF2CF3 |
| CH2CH2OEt | CH2C(O)NHCH2(CF2)2CF3 |
| CH2CH2O(i-Pr) | CH(Me)C(O)NHCH2CH2F |
| CH2CH(Me)OH | CH(Me)C(O)NHCH2CH2Cl |
| CH2CH(CF3)OH | CH(Me)C(O)NHCH2CHF2 |
| CH2C(Me)2OH | CH(Me)C(O)NHCH2CF3 |
| CH2C(CF3)(Me)OH | CH(Me)C(O)NHCH2CH(Me)F |
| CH(Me)CH2OH | CH(Me)C(O)NHCH2C(Me)2F |
| C(Me)2CH2OH | CH(Me)C(O)NH(CH2)2CH2F |
| CH(Et)CH2OH | CH(Me)C(O)NHCH2CH2CF3 |
| CH(i-Pr)CH2OH | CH(Me)C(O)NHCH2CHFCF3 |
| CH(i-Bu)CH2OH | CH(Me)C(O)NHCH2CF2CF3 |
| CH(Me)CH(CF3)OH | CH(Me)C(O)NHCH(Me)CF3 |
| CH2CH2CH2OH | CH(Me)C(O)NHCH(CF3)2 |
| CH2CH2CH2OMe | CH(Me)C(O)NHC(Me)2CF3 |
| CH2CH2CH2OEt | CH(Me)C(O)NHCH2CH(Me)CF3 |
| CH2CH2CH(CF3)OH | CH(Me)C(O)NH(CH2)2CF2CF3 |
| CH(Me)CH2CH2OH | CH(Me)C(O)NHCH2(CF2)2CF3 |
| CH2CH(Me)CH2OH | C(Me)2C(O)NHCH2CH2F |
| CH2C(Me)2CH2OH | C(Me)2C(O)NHCH2CH2Cl |
| CH2CH2CH(Me)OH | C(Me)2C(O)NHCH2CHF2 |
| CH2CH2C(Me)2OH | C(Me)2C(O)NHCH2CF3 |
| CH2CH2SMe | C(Me)2C(O)NHCH2CH(Me)F |
| CH2CH2SEt | C(Me)2C(O)NHCH2C(Me)2F |
| CH2CH2S(n-Pr) | C(Me)2C(O)NH(CH2)2CH2F |
| CH2CH2S(i-Pr) | C(Me)2C(O)NHCH2CH2CF3 |
| CH2CH2S(i-Bu) | C(Me)2C(O)NHCH2CHFCF3 |
| CH2CH(Me)SMe | C(Me)2C(O)NHCH2CF2CF3 |
| CH2CH(CF3)SMe | CH2C(O)NH(c-Pr) |
| CH2C(Me)2SMe | CH2C(O)NH(CH2-c-Pr) |
| CH(Me)CH2SMe | CH2(4-thiazolyl) |
| C(Me)2CH2SMe | CH2C(O)NH(Me) |
| CH(Et)CH2SMe | CH2C(O)NH(Et) |
| CH(i-Pr)CH2SMe | CH2C(O)NH(n-Pr) |
| CH(i-Bu)CH2SMe | CH2C(O)NH(i-Pr) |
| CH2CH2CH2SMe | CH2C(O)NH(n-Bu) |
| CH2CH2CH2SEt | CH2C(O)NH(i-Bu) |
| CH2CH2CH(Me)SMe | CH2C(O)NH(s-Bu) |
| CH2CH2CH(CF3)SMe | CH2C(O)NMe2 |
| CH(Me)CH2CH2SMe | CH2C(O)NMe(Et) |
| CH(Et)CH2CH2SMe | CH2C(O)NEt2 |
| CH2CH(Me)CH2SMe | CH2C(O)NMe(n-Pr) |
| CH2C(Me)2CH2SMe | CH2C(O)NMe(i-Pr) |
| CH2CH2S(O)Me | CH2C(O)NMe(s-Bu) |
| CH2CH2S(O)Et | CH(Me)C(O)NH(Me) |
| CH2CH2S(O)(n-Pr) | CH(Me)C(O)NH(Et) |
| CH2CH2S(O)(i-Pr) | CH(Me)C(O)NH(n-Pr) |

TABLE 3-continued

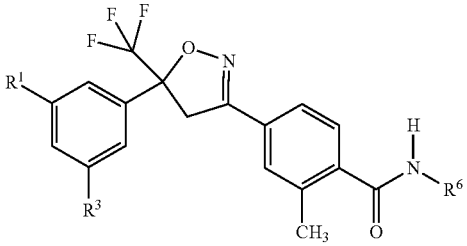

| R6 | |
|---|---|
| CH2CH2S(O)(i-Bu) | CH(Me)C(O)NH(i-Pr) |
| CH2CH(Me)S(O)Me | CH(Me)C(O)NH(n-Bu) |
| CH2CH(CF3)S(O)Me | CH(Me)C(O)NH(i-Bu) |
| CH2C(Me)2S(O)Me | CH(Me)C(O)NH(s-Bu) |
| CH(Me)CH2S(O)Me | C(Me)2C(O)NH(Me) |
| CH(Et)CH2S(O)Me | C(Me)2C(O)NH(Et) |
| CH(i-Bu)CH2S(O)Me | C(Me)2C(O)NH(n-Pr) |
| CH2CH2CH2S(O)Me | C(Me)2C(O)NH(i-Pr) |
| CH2CH2CH2S(O)Et | C(Me)2C(O)NH(n-Bu) |
| CH2CH2CH2S(O)(i-Bu) | C(Me)2C(O)NH(i-Bu) |
| CH2CH2CH(Me)S(O)Me | C(Me)2C(O)NH(s-Bu) |
| CH2CH2CH(CF3)S(O)Me | CH2C(O)N(Me)CH2CH2F |
| CH(Me)CH2CH2S(O)Me | CH2C(O)N(Me)CH2CH2Cl |
| CH(Et)CH2CH2S(O)Me | CH2C(O)N(Me)CH2CHF2 |
| CH2CH(Me)CH2S(O)Me | CH2C(O)N(Me)CH2CF3 |
| CH2C(Me)2CH2S(O)Me | CH2C(O)N(Me)CH2CH2CH2F |
| CH2(2-pyridinyl) | CH2C(O)N(Me)CH2CH2CF3 |
| CH2CH2SO2Me | CH2C(O)N(Me)CH2CF2CF3 |
| CH2CH2SO2Et | CH2C(O)N(Me)CH(Me)CF3 |
| CH2CH2SO2(n-Pr) | CH2C(O)N(Me)CH(CF3)2 |
| CH2CH2SO2(i-Pr) | CH2C(O)N(Me)C(Me)2CF3 |
| CH2CH(Me)SO2Me | CH(Me)C(O)N(Me)CH2CH2F |
| CH2CH(CF3)SO2Me | CH(Me)C(O)N(Me)CH2CH2Cl |
| CH2C(Me)2SO2Me | CH(Me)C(O)N(Me)CH2CHF2 |
| CH(Me)CH2SO2Me | CH(Me)C(O)N(Me)CH2CF3 |
| C(Me)2CH2SO2Me | CH(Me)C(O)N(Me)(CH2)2CH2F |
| CH(Et)CH2SO2Me | CH(Me)C(O)N(Me)CH2CH2CF3 |
| CH(i-Pr)CH2SO2Me | CH(Me)C(O)N(Me)CH2CF2CF3 |
| CH(i-Bu)CH2SO2Me | CH(Me)C(O)N(Me)CH(Me)CF3 |
| CH2CH2CH2SO2Me | CH(Me)C(O)N(Me)CH(CF3)2 |
| CH2CH2CH2SO2Et | CH(Me)C(O)N(Me)C(Me)2CF3 |
| CH2CH2CH(Me)SO2Me | C(Me)2C(O)N(Me)CH2CH2F |
| CH2CH2CH(CF3)SO2Me | C(Me)2C(O)N(Me)CH2CH2Cl |
| CH(Me)CH2CH2SO2Me | C(Me)2C(O)N(Me)CH2CHF2 |
| CH(Et)CH2CH2SO2Me | C(Me)2C(O)N(Me)CH2CF3 |
| CH2CH(Me)CH2SO2Me | C(Me)2C(O)N(Me)CH2CH2CH2F |
| CH2C(Me)2CH2SO2Me | C(Me)2C(O)N(Me)CH2CH2CF3 |
| CH2C(O)NHCH2CH2F | C(Me)2C(O)N(Me)CH2CF2CF3 |
| CH2C(O)NHCH2CH2Cl | C(Me)2C(O)N(Me)CH(Me)CF3 |
| CH2C(O)NHCH2CHF2 | C(Me)2C(O)N(Me)CH(CF3)2 |
| CH2C(O)NHCH2CF3 | C(Me)2C(O)N(Me)C(Me)2CF3 |
| CH2C(O)NHCH2CH(Me)F | C(Me)2C(O)NHCH(Me)CF3 |
| CH2C(O)NHCH2C(Me)2F | C(Me)2C(O)NHCH(CF3)2 |
| CH2C(O)NH(CH2)2CH2F | C(Me)2C(O)NHC(Me)2CF3 |
| CH2C(O)NHCH2CH2CF3 | C(Me)2C(O)NHCH2CH(Me)CF3 |
| CH2C(O)NHCH2CHFCF3 | C(Me)2C(O)NH(CH2)2CF2CF3 |
| CH2C(O)NHCH2CF2CF3 | C(Me)2C(O)NHCH2(CF2)2CF3 |
| CH2C(O)NHCH(Me)CF3 | C(Me)2C(O)NHCH(i-Pr)CF3 |
| CH2C(O)NHCH(CF3)2 | CH(Me)C(O)NH(c-Pr) |
| CH2C(O)NHC(Me)2CF3 | CH(Me)C(O)NH(CH2-c-Pr) |

R1 is CF3, R3 is Cl

| | |
|---|---|
| CH2CH2OH | CH2C(O)NHCH2CH(Me)CF3 |
| CH2CH2OMe | CH2C(O)NH(CH2)2CF2CF3 |
| CH2CH2OEt | CH2C(O)NHCH2(CF2)2CF3 |
| CH2CH2O(i-Pr) | CH(Me)C(O)NHCH2CH2F |
| CH2CH(Me)OH | CH(Me)C(O)NHCH2CH2Cl |
| CH2CH(CF3)OH | CH(Me)C(O)NHCH2CHF2 |
| CH2C(Me)2OH | CH(Me)C(O)NHCH2CF3 |
| CH2C(CF3)(Me)OH | CH(Me)C(O)NHCH2CH(Me)F |
| CH(Me)CH2OH | CH(Me)C(O)NHCH2C(Me)2F |
| C(Me)2CH2OH | CH(Me)C(O)NH(CH2)2CH2F |
| CH(Et)CH2OH | CH(Me)C(O)NHCH2CH2CF3 |
| CH(i-Pr)CH2OH | CH(Me)C(O)NHCH2CHFCF3 |
| CH(i-Bu)CH2OH | CH(Me)C(O)NHCH2CF2CF3 |

TABLE 3-continued

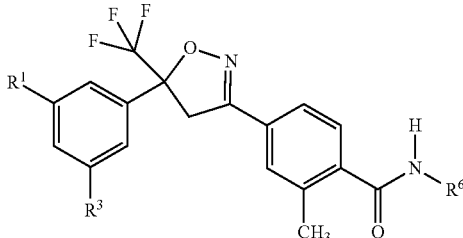

| R⁶ | |
|---|---|
| CH(Me)CH(CF₃)OH | CH(Me)C(O)NHCH(Me)CF₃ |
| CH₂CH₂CH₂OH | CH(Me)C(O)NHCH(CF₃)₂ |
| CH₂CH₂CH₂OMe | CH(Me)C(O)NHC(Me)₂CF₃ |
| CH₂CH₂CH₂OEt | CH(Me)C(O)NHCH₂CH(Me)CF₃ |
| CH₂CH₂CH(CF₃)OH | CH(Me)C(O)NHCH(CH₂)₂CF₂CF₃ |
| CH(Me)CH₂CH₂OH | CH(Me)C(O)NHCH₂(CF₂)₂CF₃ |
| CH₂CH(Me)CH₂OH | C(Me)₂C(O)NHCH₂CH₂F |
| CH₂C(Me)₂CH₂OH | C(Me)₂C(O)NHCH₂CH₂Cl |
| CH₂CH₂CH(Me)OH | C(Me)₂C(O)NHCH₂CHF₂ |
| CH₂CH₂C(Me)₂OH | C(Me)₂C(O)NHCH₂CF₃ |
| CH₂CH₂SMe | C(Me)₂C(O)NHCH₂CH(Me)F |
| CH₂CH₂SEt | C(Me)₂C(O)NHCH₂C(Me)₂F |
| CH₂CH₂S(n-Pr) | C(Me)₂C(O)NHCH(CH₂)₂CH₂F |
| CH₂CH₂S(i-Pr) | C(Me)₂C(O)NHCH₂CH₂CF₃ |
| CH₂CH₂S(i-Bu) | C(Me)₂C(O)NHCH₂CHFCF₃ |
| CH₂CH(Me)SMe | C(Me)₂C(O)NHCH₂CF₂CF₃ |
| CH₂CH(CF₃)SMe | CH₂C(O)NH(c-Pr) |
| CH₂C(Me)₂SMe | CH₂C(O)NH(CH₂-c-Pr) |
| CH(Me)CH₂SMe | CH₂(4-thiazolyl) |
| C(Me)₂CH₂SMe | CH₂C(O)NH(Me) |
| CH(Et)CH₂SMe | CH₂C(O)NH(Et) |
| CH(i-Pr)CH₂SMe | CH₂C(O)NH(n-Pr) |
| CH(i-Bu)CH₂SMe | CH₂C(O)NH(i-Pr) |
| CH₂CH₂CH₂SMe | CH₂C(O)NH(n-Bu) |
| CH₂CH₂CH₂SEt | CH₂C(O)NH(i-Bu) |
| CH₂CH₂CH(Me)SMe | CH₂C(O)NH(s-Bu) |
| CH₂CH₂CH(CF₃)SMe | CH₂C(O)NMe₂ |
| CH(Me)CH₂CH₂SMe | CH₂C(O)NMe(Et) |
| CH(Et)CH₂CH₂SMe | CH₂C(O)NEt₂ |
| CH₂CH(Me)CH₂SMe | CH₂C(O)NMe(n-Pr) |
| CH₂C(Me)₂CH₂SMe | CH₂C(O)NMe(i-Pr) |
| CH₂CH₂S(O)Me | CH₂C(O)NMe(s-Bu) |
| CH₂CH₂S(O)Et | CH(Me)C(O)NH(Me) |
| CH₂CH₂S(O)(n-Pr) | CH(Me)C(O)NH(Et) |
| CH₂CH₂S(O)(i-Pr) | CH(Me)C(O)NH(n-Pr) |
| CH₂CH₂S(O)(i-Bu) | CH(Me)C(O)NH(i-Pr) |
| CH₂CH(Me)S(O)Me | CH(Me)C(O)NH(n-Bu) |
| CH₂CH(CF₃)S(O)Me | CH(Me)C(O)NH(i-Bu) |
| CH₂C(Me)₂S(O)Me | CH(Me)C(O)NH(s-Bu) |
| CH(Me)CH₂S(O)Me | C(Me)₂C(O)NH(Me) |
| CH(Et)CH₂S(O)Me | C(Me)₂C(O)NH(Et) |
| CH(i-Bu)CH₂S(O)Me | C(Me)₂C(O)NH(n-Pr) |
| CH₂CH₂CH₂S(O)Me | C(Me)₂C(O)NH(i-Pr) |
| CH₂CH₂CH₂S(O)Et | C(Me)₂C(O)NH(n-Bu) |
| CH₂CH₂CH₂S(O)(i-Bu) | C(Me)₂C(O)NH(i-Bu) |
| CH₂CH₂CH(Me)S(O)Me | C(Me)₂C(O)NH(s-Bu) |
| CH₂CH₂CH(CF₃)S(O)Me | CH₂C(O)N(Me)CH₂CH₂F |
| CH(Me)CH₂CH₂S(O)Me | CH₂C(O)N(Me)CH₂CH₂Cl |
| CH(Et)CH₂CH₂S(O)Me | CH₂C(O)N(Me)CH₂CHF₂ |
| CH₂CH(Me)CH₂S(O)Me | CH₂C(O)N(Me)CH₂CF₃ |
| CH₂C(Me)₂CH₂S(O)Me | CH₂C(O)N(Me)CH₂CH₂CH₂F |
| CH₂(2-pyridinyl) | CH₂C(O)N(Me)CH₂CH₂CF₃ |
| CH₂CH₂SO₂Me | CH₂C(O)N(Me)CH₂CF₂CF₃ |
| CH₂CH₂SO₂Et | CH₂C(O)N(Me)CH(Me)CF₃ |
| CH₂CH₂SO₂(n-Pr) | CH₂C(O)N(Me)CH(CF₃)₂ |
| CH₂CH₂SO₂(i-Pr) | CH₂C(O)N(Me)C(Me)₂CF₃ |
| CH₂CH(Me)SO₂Me | CH(Me)C(O)N(Me)CH₂CH₂F |
| CH₂CH(CF₃)SO₂Me | CH(Me)C(O)N(Me)CH₂CH₂Cl |
| CH₂C(Me)²SO₂Me | CH(Me)C(O)N(Me)CH₂CHF₂ |
| CH(Me)CH₂SO₂Me | CH(Me)C(O)N(Me)CH₂CF₃ |
| C(Me)₂CH₂SO₂Me | CH(Me)C(O)N(Me)(CH₂)₂CH₂F |
| CH(Et)CH₂SO₂Me | CH(Me)C(O)N(Me)CH₂CH₂CF₃ |
| CH(i-Pr)CH₂SO₂Me | CH(Me)C(O)N(Me)CH₂CF₂CF₃ |
| CH(i-Bu)CH₂SO₂Me | CH(Me)C(O)N(Me)CH(Me)CF₃ |
| CH₂CH₂CH₂SO₂Me | CH(Me)C(O)N(Me)CH(CF₃)₂ |

TABLE 3-continued

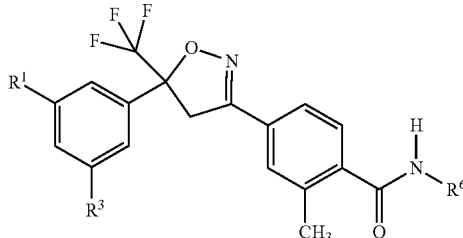

| R⁶ | |
|---|---|
| CH₂CH₂CH₂SO₂Et | CH(Me)C(O)N(Me)C(Me)₂CF₃ |
| CH₂CH₂CH(Me)SO₂Me | C(Me)₂C(O)N(Me)CH₂CH₂F |
| CH₂CH₂CH(CF₃)SO₂Me | C(Me)₂C(O)N(Me)CH₂CH₂Cl |
| CH(Me)CH₂CH₂SO₂Me | C(Me)₂C(O)N(Me)CH₂CHF₂ |
| CH(Et)CH₂CH₂SO₂Me | C(Me)₂C(O)N(Me)CH₂CF₃ |
| CH₂CH(Me)CH₂SO₂Me | C(Me)₂C(O)N(Me)CH₂CH₂CH₂F |
| CH₂C(Me)₂CH₂SO₂Me | C(Me)₂C(O)N(Me)CH₂CH₂CF₃ |
| CH₂C(O)NHCH₂CH₂F | C(Me)₂C(O)N(Me)CH₂CF₂CF₃ |
| CH₂C(O)NHCH₂CH₂Cl | C(Me)₂C(O)N(Me)CH(Me)CF₃ |
| CH₂C(O)NHCH₂CHF₂ | C(Me)₂C(O)N(Me)CH(CF₃)₂ |
| CH₂C(O)NHCH₂CF₃ | C(Me)₂C(O)N(Me)C(Me)₂CF₃ |
| CH₂C(O)NHCH₂CH(Me)F | C(Me)₂C(O)NHCH(Me)CF₃ |
| CH₂C(O)NHCH₂C(Me)₂F | C(Me)₂C(O)NHCH(CF₃)₂ |
| CH₂C(O)NH(CH₂)₂CH₂F | C(Me)₂C(O)NHC(Me)₂CF₃ |
| CH₂C(O)NHCH₂CH₂CF₃ | C(Me)₂C(O)NHCH(Me)CF₃ |
| CH₂C(O)NHCH₂CHFCF₃ | C(Me)₂C(O)NH(CH₂)₂CF₂CF₃ |
| CH₂C(O)NHCH₂CF₂CF₃ | C(Me)₂C(O)NHCH₂(CF₂)₂CF₃ |
| CH₂C(O)NHCH(Me)CF₃ | C(Me)₂C(O)NHCH(i-Pr)CF₃ |
| CH₂C(O)NHCH(CF₃)₂ | CH(Me)C(O)NH(c-Pr) |
| CH₂C(O)NHC(Me)₂CF₃ | CH(Me)C(O)NH(CH₂-c-Pr) |
| | R¹ is CF₃, R³ is Br |
| CH₂CH₂OH | CH₂C(O)NHCH₂CH(Me)CF₃ |
| CH₂CH₂OMe | CH₂C(O)NH(CH₂)₂CF₂CF₃ |
| CH₂CH₂OEt | CH₂C(O)NHCH₂(CF₂)₂CF₃ |
| CH₂CH₂O(i-Pr) | CH(Me)C(O)NHCH₂CH₂F |
| CH₂CH(Me)OH | CH(Me)C(O)NHCH₂CH₂Cl |
| CH₂CH(CF₃)OH | CH(Me)C(O)NHCH₂CHF₂ |
| CH₂C(Me)₂OH | CH(Me)C(O)NHCH₂CF₃ |
| CH₂C(CF₃)(Me)OH | CH(Me)C(O)NHCH₂CH(Me)F |
| CH(Me)CH₂OH | CH(Me)C(O)NHCH₂C(Me)₂F |
| C(Me)₂CH₂OH | CH(Me)C(O)NH(CH₂)₂CH₂F |
| CH(Et)CH₂OH | CH(Me)C(O)NHCH₂CH₂CF₃ |
| CH(i-Pr)CH₂OH | CH(Me)C(O)NHCH₂CHFCF₃ |
| CH(i-Bu)CH₂OH | CH(Me)C(O)NHCH₂CF₂CF₃ |
| CH(Me)CH(CF₃)OH | CH(Me)C(O)NHCH(Me)CF₃ |
| CH₂CH₂CH₂OH | CH(Me)C(O)NHCH(CF₃)₂ |
| CH₂CH₂CH₂OMe | CH(Me)C(O)NHC(Me)₂CF₃ |
| CH₂CH₂CH₂OEt | CH(Me)C(O)NHCH₂CH(Me)CF₃ |
| CH₂CH₂CH(CF₃)OH | CH(Me)C(O)NH(CH₂)₂CF₂CF₃ |
| CH(Me)CH₂CH₂OH | CH(Me)C(O)NHCH₂(CF₂)₂CF₃ |
| CH₂CH(Me)CH₂OH | C(Me)₂C(O)NHCH₂CH₂F |
| CH₂C(Me)₂CH₂OH | C(Me)₂C(O)NHCH₂CH₂Cl |
| CH₂CH₂CH(Me)OH | C(Me)₂C(O)NHCH₂CHF₂ |
| CH₂CH₂C(Me)₂OH | C(Me)₂C(O)NHCH₂CF₃ |
| CH₂CH₂SMe | C(Me)₂C(O)NHCH₂CH(Me)F |
| CH₂CH₂SEt | C(Me)₂C(O)NHCH₂C(Me)₂F |
| CH₂CH₂S(n-Pr) | C(Me)₂C(O)NH(CH₂)₂CH₂F |
| CH₂CH₂S(i-Pr) | C(Me)₂C(O)NHCH₂CH₂CF₃ |
| CH₂CH₂S(i-Bu) | C(Me)₂C(O)NHCHFCF₃ |
| CH₂CH(Me)SMe | C(Me)₂C(O)NHCH₂CF₂CF₃ |
| CH₂CH(CF₃)SMe | CH₂C(O)NH(c-Pr) |
| CH₂C(Me)₂SMe | CH₂C(O)NH(CH₂-c-Pr) |
| CH(Me)CH₂SMe | CH₂(4-thiazolyl) |
| C(Me)₂CH₂SMe | CH₂C(O)NH(Me) |
| CH(Et)CH₂SMe | CH₂C(O)NH(Et) |
| CH(i-Pr)CH₂SMe | CH₂C(O)NH(n-Pr) |
| CH(i-Bu)CH₂SMe | CH₂C(O)NH(i-Pr) |
| CH₂CH₂CH₂SMe | CH₂C(O)NH(n-Bu) |
| CH₂CH₂CH₂SEt | CH₂C(O)NH(i-Bu) |
| CH₂CH₂CH(Me)SMe | CH₂C(O)NH(s-Bu) |
| CH₂CH₂CH(CF₃)SMe | CH₂C(O)NMe₂ |
| CH(Me)CH₂CH₂SMe | CH₂C(O)NMe(Et) |
| CH(Et)CH₂CH₂SMe | CH₂C(O)NEt₂ |
| CH₂CH(Me)CH₂SMe | CH₂C(O)NMe(n-Pr) |

TABLE 3-continued

[Structure: isoxazoline with CF3 group, R1 and R3 on phenyl ring, connected to benzamide with CH3 and N(H)R6]

| R6 | |
|---|---|
| CH2C(Me)2CH2SMe | CH2C(O)NMe(i-Pr) |
| CH2CH2S(O)Me | CH2C(O)NMe(s-Bu) |
| CH2CH2S(O)Et | CH(Me)C(O)NH(Me) |
| CH2CH2S(O)(n-Pr) | CH(Me)C(O)NH(Et) |
| CH2CH2S(O)(i-Pr) | CH(Me)C(O)NH(n-Pr) |
| CH2CH2S(O)(i-Bu) | CH(Me)C(O)NH(i-Pr) |
| CH2CH(Me)S(O)Me | CH(Me)C(O)NH(n-Bu) |
| CH2CH(CF3)S(O)Me | CH(Me)C(O)NH(i-Bu) |
| CH2C(Me)2S(O)Me | CH(Me)C(O)NH(s-Bu) |
| CH(Me)CH2S(O)Me | C(Me)2C(O)NH(Me) |
| CH(Et)CH2S(O)Me | C(Me)2C(O)NH(Et) |
| CH(i-Bu)CH2S(O)Me | C(Me)2C(O)NH(n-Pr) |
| CH2CH2CH2S(O)Me | C(Me)2C(O)NH(i-Pr) |
| CH2CH2CH2S(O)Et | C(Me)2C(O)NH(n-Bu) |
| CH2CH2CH2S(O)(i-Bu) | C(Me)2C(O)NH(i-Bu) |
| CH2CH2CH(Me)S(O)Me | C(Me)2C(O)NH(s-Bu) |
| CH2CH2CH(CF3)S(O)Me | CH2C(O)N(Me)CH2CH2F |
| CH(Me)CH2CH2S(O)Me | CH2C(O)N(Me)CH2CH2Cl |
| CH(Et)CH2CH2S(O)Me | CH2C(O)N(Me)CH2CHF2 |
| CH2CH(Me)CH2S(O)Me | CH2C(O)N(Me)CH2CF3 |
| CH2C(Me)2CH2S(O)Me | CH2C(O)N(Me)CH2CH2CH2F |
| CH2(2-pyridinyl) | CH2C(O)N(Me)CH2CH2CF3 |
| CH2CH2SO2Me | CH2C(O)N(Me)CH2CF2CF3 |
| CH2CH2SO2Et | CH2C(O)N(Me)CH(Me)CF3 |
| CH2CH2SO2(n-Pr) | CH2C(O)N(Me)CH(CF3)2 |
| CH2CH2SO2(i-Pr) | CH2C(O)N(Me)C(Me)2CF3 |
| CH2CH(Me)SO2Me | CH(Me)C(O)N(Me)CH2CH2F |
| CH2CH(CF3)SO2Me | CH(Me)C(O)N(Me)CH2CH2Cl |
| CH2C(Me)2SO2Me | CH(Me)C(O)N(Me)CH2CHF2 |
| CH(Me)CH2SO2Me | CH(Me)C(O)N(Me)CH2CF3 |
| C(Me)2CH2SO2Me | CH(Me)C(O)N(Me)(CH2)2CH2F |
| CH(Et)CH2SO2Me | CH(Me)C(O)N(Me)CH2CH2CF3 |
| CH(i-Pr)CH2SO2Me | CH(Me)C(O)N(Me)CH2CF2CF3 |
| CH(i-Bu)CH2SO2Me | CH(Me)C(O)N(Me)CH(Me)CF3 |
| CH2CH2CH2SO2Me | CH(Me)C(O)N(Me)CH(CF3)2 |
| CH2CH2CH2SO2Et | CH(Me)C(O)N(Me)C(Me)2CF3 |
| CH2CH2CH(Me)SO2Me | C(Me)2C(O)N(Me)CH2CH2F |
| CH2CH2CH(CF3)SO2Me | C(Me)2C(O)N(Me)CH2CH2Cl |
| CH(Me)CH2CH2SO2Me | C(Me)2C(O)N(Me)CH2CHF2 |
| CH(Et)CH2CH2SO2Me | C(Me)2C(O)N(Me)CH2CF3 |
| CH2CH(Me)CH2SO2Me | C(Me)2C(O)N(Me)CH2CH2CH2F |
| CH2C(Me)2SO2Me | C(Me)2C(O)N(Me)CH2CH2CF3 |
| CH2C(O)NHCH2CH2F | C(Me)2C(O)N(Me)CH2CF2CF3 |
| CH2C(O)NHCH2CH2Cl | C(Me)2C(O)N(Me)CH(Me)CF3 |
| CH2C(O)NHCH2CHF2 | C(Me)2C(O)N(Me)CH(CF3)2 |
| CH2C(O)NHCH2CF3 | C(Me)2C(O)N(Me)C(Me)2CF3 |
| CH2C(O)NHCH2CH(Me)F | C(Me)2C(O)NHCH(Me)CF3 |
| CH2C(O)NHCH2C(Me)2F | C(Me)2C(O)NHCH(CF3)2 |
| CH2C(O)NH(CH2)2CH2F | C(Me)2C(O)NHC(Me)2CF3 |
| CH2C(O)NHCH2CH2CF3 | C(Me)2C(O)N(Me)CH(Me)CF3 |
| CH2C(O)NHCH2CHFCF3 | C(Me)2C(O)NH(CH2)2CF2CF3 |
| CH2C(O)NHCH2CF2CF3 | C(Me)2C(O)NHCH2(CF2)2CF3 |
| CH2C(O)NHCH(Me)CF3 | C(Me)2C(O)NHCH(i-Pr)CF3 |
| CH2C(O)NHCH(CF3)2 | CH(Me)C(O)NH(c-Pr) |
| CH2C(O)NHC(Me)2CF3 | CH(Me)C(O)NH(CH2-c-Pr) |

R1 is CF3, R3 is CF3

| | |
|---|---|
| CH2CH2OH | CH2C(O)NHCH2CH(Me)CF3 |
| CH2CH2OMe | CH2C(O)NH(CH2)2CF2CF3 |
| CH2CH2OEt | CH2C(O)NHCH2(CF2)2CF3 |
| CH2CH2O(i-Pr) | CH(Me)C(O)NHCH2CH2F |
| CH2CH(Me)OH | CH(Me)C(O)NHCH2CH2Cl |
| CH2CH(CF3)OH | CH(Me)C(O)NHCH2CHF2 |
| CH2C(Me)2OH | CH(Me)C(O)NHCH2CF3 |
| CH2C(CF3)(Me)OH | CH(Me)C(O)NHCH2CH(Me)F |

TABLE 3-continued

[Structure: isoxazoline with CF3 group, R1 and R3 on phenyl ring, connected to benzamide with CH3 and N(H)R6]

| R6 | |
|---|---|
| CH(Me)CH2OH | CH(Me)C(O)NHCH2C(Me)2F |
| C(Me)2CH2OH | CH(Me)C(O)NH(CH2)2CH2F |
| CH(Et)CH2OH | CH(Me)C(O)NHCH2CH2CF3 |
| CH(i-Pr)CH2OH | CH(Me)C(O)NHCH2CHFCF3 |
| CH(i-Bu)CH2OH | CH(Me)C(O)NHCH2CF2CF3 |
| CH(Me)CH(CF3)OH | CH(Me)C(O)NHCH(Me)CF3 |
| CH2CH2CH2OH | CH(Me)C(O)NHCH(CF3)2 |
| CH2CH2CH2OMe | CH(Me)C(O)NHC(Me)2CF3 |
| CH2CH2CH2OEt | CH(Me)C(O)NHCH2CH(Me)CF3 |
| CH2CH2CH(CF3)OH | CH(Me)C(O)NH(CH2)2CF2CF3 |
| CH(Me)CH2CH2OH | CH(Me)C(O)NHCH2(CF2)2CF3 |
| CH2CH(Me)CH2OH | C(Me)2C(O)NHCH2CH2F |
| CH2C(Me)2CH2OH | C(Me)2C(O)NHCH2CH2Cl |
| CH2CH(Me)CH(Me)OH | C(Me)2C(O)NHCH2CHF2 |
| CH2CH2C(Me)2OH | C(Me)2C(O)NHCH2CF3 |
| CH2CH2SMe | C(Me)2C(O)NHCH2CH(Me)F |
| CH2CH2SEt | C(Me)2C(O)NHCH2C(Me)2F |
| CH2CH2S(n-Pr) | C(Me)2C(O)NH(CH2)2CH2F |
| CH2CH2S(i-Pr) | C(Me)2C(O)NHCH2CH2CF3 |
| CH2CH2S(i-Bu) | C(Me)2C(O)NHCH2CHFCF3 |
| CH2CH(Me)SMe | C(Me)2C(O)NHCH2CF2CF3 |
| CH2CH(CF3)SMe | CH2C(O)NH(c-Pr) |
| CH2C(Me)2SMe | CH2C(O)NH(CH2-c-Pr) |
| CH(Me)CH2SMe | CH2(4-thiazolyl) |
| C(Me)2CH2SMe | CH2C(O)NH(Me) |
| CH(Et)CH2SMe | CH2C(O)NH(Et) |
| CH(i-Pr)CH2SMe | CH2C(O)NH(n-Pr) |
| CH(i-Bu)CH2SMe | CH2C(O)NH(i-Pr) |
| CH2CH2CH2SMe | CH2C(O)NH(n-Bu) |
| CH2CH2CH2SEt | CH2C(O)NH(i-Bu) |
| CH2CH2CH(Me)SMe | CH2C(O)NH(s-Bu) |
| CH2CH2CH(CF3)SMe | CH2C(O)NMe2 |
| CH(Me)CH2CH2SMe | CH2C(O)NMe(Et) |
| CH(Et)CH2CH2SMe | CH2C(O)NEt2 |
| CH2CH(Me)CH2SMe | CH2C(O)NMe(n-Pr) |
| CH2C(Me)2CH2SMe | CH2C(O)NMe(i-Pr) |
| CH2CH2S(O)Me | CH2C(O)NMe(s-Bu) |
| CH2CH2S(O)Et | CH(Me)C(O)NH(Me) |
| CH2CH2S(O)(n-Pr) | CH(Me)C(O)NH(Et) |
| CH2CH2S(O)(i-Pr) | CH(Me)C(O)NH(n-Pr) |
| CH2CH2S(O)(i-Bu) | CH(Me)C(O)NH(i-Pr) |
| CH2CH(Me)S(O)Me | CH(Me)C(O)NH(n-Bu) |
| CH2CH(CF3)S(O)Me | CH(Me)C(O)NH(i-Bu) |
| CH2C(Me)2S(O)Me | CH(Me)C(O)NH(s-Bu) |
| CH(Me)CH2S(O)Me | C(Me)2C(O)NH(Me) |
| CH(Et)CH2S(O)Me | C(Me)2C(O)NH(Et) |
| CH(i-Bu)CH2S(O)Me | C(Me)2C(O)NH(n-Pr) |
| CH2CH2CH2S(O)Me | C(Me)2C(O)NH(i-Pr) |
| CH2CH2CH2S(O)Et | C(Me)2C(O)NH(n-Bu) |
| CH2CH2CH2S(O)(i-Bu) | C(Me)2C(O)NH(i-Bu) |
| CH2CH2CH(Me)S(O)Me | C(Me)2C(O)NH(s-Bu) |
| CH2CH2CH(CF3)S(O)Me | CH2C(O)N(Me)CH2CH2F |
| CH(Me)CH2CH2S(O)Me | CH2C(O)N(Me)CH2CH2Cl |
| CH(Et)CH2CH2S(O)Me | CH2C(O)N(Me)CH2CHF2 |
| CH2CH(Me)CH2S(O)Me | CH2C(O)N(Me)CH2CF3 |
| CH2C(Me)2CH2S(O)Me | CH2C(O)N(Me)CH2CH2CH2F |
| CH2(2-pyridinyl) | CH2C(O)N(Me)CH2CH2CF3 |
| CH2CH2SO2Me | CH2C(O)N(Me)CH2CF2CF3 |
| CH2CH2SO2Et | CH2C(O)N(Me)CH(Me)CF3 |
| CH2CH2SO2(n-Pr) | CH2C(O)N(Me)CH(CF3)2 |
| CH2CH2SO2(i-Pr) | CH2C(O)N(Me)C(Me)2CF3 |
| CH2CH(Me)SO2Me | CH(Me)C(O)N(Me)CH2CH2F |
| CH2CH(CF3)SO2Me | CH(Me)C(O)N(Me)CH2CH2Cl |
| CH2C(Me)2SO2Me | CH(Me)C(O)N(Me)CH2CHF2 |
| CH(Me)CH2SO2Me | CH(Me)C(O)N(Me)CH2CF3 |

TABLE 3-continued

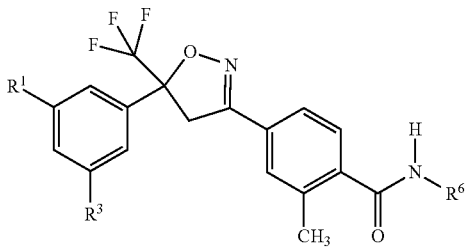

| R⁶ | |
|---|---|
| C(Me)₂CH₂SO₂Me | CH(Me)C(O)N(Me)(CH₂)₂CH₂F |
| CH(Et)CH₂SO₂Me | CH(Me)C(O)N(Me)CH₂CH₂CF₃ |
| CH(i-Pr)CH₂SO₂Me | CH(Me)C(O)N(Me)CH₂CF₂CF₃ |
| CH(i-Bu)CH₂SO₂Me | CH(Me)C(O)N(Me)CH(Me)CF₃ |
| CH₂CH₂CH₂SO₂Me | CH(Me)C(O)N(Me)CH(CF₃)₂ |
| CH₂CH₂CH₂SO₂Et | CH(Me)C(O)N(Me)C(Me)₂CF₃ |
| CH₂CH₂CH(Me)SO₂Me | C(Me)₂C(O)N(Me)CH₂CH₂F |
| CH₂CH₂CH(CF₃)SO₂Me | C(Me)₂C(O)N(Me)CH₂CH₂Cl |
| CH(Me)CH₂CH₂SO₂Me | C(Me)₂C(O)N(Me)CH₂CHF₂ |
| CH(Et)CH₂CH₂SO₂Me | C(Me)₂C(O)N(Me)CH₂CF₃ |
| CH₂CH(Me)CH₂SO₂Me | C(Me)₂C(O)N(Me)CH₂CH₂CH₂F |
| CH₂C(Me)₂CH₂SO₂Me | C(Me)₂C(O)N(Me)CH₂CH₂CF₃ |
| CH₂C(O)NHCH₂F | C(Me)₂C(O)N(Me)CH₂CF₂CF₃ |
| CH₂C(O)NHCH₂CH₂Cl | C(Me)₂C(O)N(Me)CH(Me)CF₃ |
| CH₂C(O)NHCH₂CHF₂ | C(Me)₂C(O)N(Me)CH(CF₃)₂ |
| CH₂C(O)NHCH₂CF₃ | C(Me)₂C(O)N(Me)C(Me)₂CF₃ |
| CH₂C(O)NHCH₂CH(Me)F | C(Me)₂C(O)N(Me)CH(Me)CF₃ |
| CH₂C(O)NHCH₂C(Me)₂F | C(Me)₂C(O)NHCH(CF₃)₂ |
| CH₂C(O)NH(CH₂)₂CH₂F | C(Me)₂C(O)NHC(Me)₂CF₃ |
| CH₂C(O)NHCH₂CH₂CF₃ | C(Me)₂C(O)NHCH₂CH(Me)CF₃ |
| CH₂C(O)NHCHFCF₃ | C(Me)₂C(O)NHCH(CH₂)₂CF₂CF₃ |
| CH₂C(O)NHCH₂CF₂CF₃ | C(Me)₂C(O)NHCH(CF₂)₂CF₃ |
| CH₂C(O)NHCH(Me)CF₃ | C(Me)₂C(O)NHCH(i-Pr)CF₃ |
| CH₂C(O)NHCH(CF₃)₂ | CH(Me)C(O)NH(c-Pr) |
| CH₂C(O)NHC(Me)₂CF₃ | CH(Me)C(O)NH(CH₂-c-Pr) |

R¹ is OCF₃, R³ is Cl

| | |
|---|---|
| CH₂CH₂OH | CH₂C(O)NHCH₂CH(Me)CF₃ |
| CH₂CH₂OMe | CH₂C(O)NH(CH₂)₂CF₂CF₃ |
| CH₂CH₂OEt | CH₂C(O)NHCH₂(CF₂)₂CF₃ |
| CH₂CH₂O(i-Pr) | CH(Me)C(O)NHCH₂CH₂F |
| CH₂CH(Me)OH | CH(Me)C(O)NHCH₂CH₂Cl |
| CH₂CH(CF₃)OH | CH(Me)C(O)NHCH₂CHF₂ |
| CH₂C(Me)₂OH | CH(Me)C(O)NHCH₂CF₃ |
| CH₂C(CF₃)(Me)OH | CH(Me)C(O)NHCH₂CH(Me)F |
| CH(Me)CH₂OH | CH(Me)C(O)NHCH₂C(Me)₂F |
| C(Me)₂CH₂OH | CH(Me)C(O)NH(CH₂)₂CH₂F |
| CH(Et)CH₂OH | CH(Me)C(O)NHCH₂CH₂CF₃ |
| CH(i-Pr)CH₂OH | CH(Me)C(O)NHCH₂CHFCF₃ |
| CH(i-Bu)CH₂OH | CH(Me)C(O)NHCH₂CF₂CF₃ |
| CH(Me)CH(CF₃)OH | CH(Me)C(O)NHCH(Me)CF₃ |
| CH₂CH₂CH₂OH | CH(Me)C(O)NHCH(CF₃)₂ |
| CH₂CH₂CH₂OMe | CH(Me)C(O)NHC(Me)₂CF₃ |
| CH₂CH₂CH₂OEt | CH(Me)C(O)NHCH₂CH(Me)CF₃ |
| CH₂CH₂CH(CF₃)OH | CH(Me)C(O)NH(CH₂)₂CF₂CF₃ |
| CH(Me)CH₂CH₂OH | CH(Me)C(O)NHCH₂(CF₂)₂CF₃ |
| CH₂CH(Me)CH₂OH | C(Me)₂C(O)NHCH₂CH₂F |
| CH₂C(Me)₂CH₂OH | C(Me)₂C(O)NHCH₂CH₂Cl |
| CH₂CH₂CH(Me)OH | C(Me)₂C(O)NHCH₂CHF₂ |
| CH₂CH(Me)₂OH | C(Me)₂C(O)NHCH₂CF₃ |
| CH₂CH₂SMe | C(Me)₂C(O)NHCH₂CH(Me)F |
| CH₂CH₂SEt | C(Me)₂C(O)NHCH₂C(Me)₂F |
| CH₂CH₂S(n-Pr) | C(Me)₂C(O)NH(CH₂)₂CH₂F |
| CH₂CH₂S(i-Pr) | C(Me)₂C(O)NHCH₂CH₂CF₃ |
| CH₂CH₂S(i-Bu) | C(Me)₂C(O)NHCH₂CHFCF₃ |
| CH₂CH(Me)SMe | C(Me)₂C(O)NHCH₂CF₂CF₃ |
| CH₂CH(CF₃)SMe | CH₂C(O)NH(c-Pr) |
| CH₂C(Me)₂SMe | CH₂C(O)NH(CH₂-c-Pr) |
| CH(Me)CH₂SMe | CH₂(4-thiazolyl) |
| C(Me)₂CH₂SMe | CH₂C(O)NH₂ |
| CH(Et)CH₂SMe | CH₂C(O)NH(Et) |
| CH(i-Pr)CH₂SMe | CH₂C(O)NH(n-Pr) |
| CH(i-Bu)CH₂SMe | CH₂C(O)NH(i-Pr) |
| CH₂CH₂CH₂SMe | CH₂C(O)NH(n-Bu) |
| CH₂CH₂CH₂SEt | CH₂C(O)NH(i-Bu) |

TABLE 3-continued

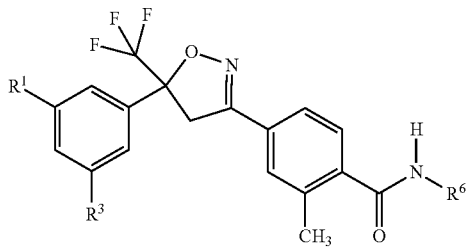

| R⁶ | |
|---|---|
| CH₂CH₂CH(Me)SMe | CH₂C(O)NH(s-Bu) |
| CH₂CH₂CH(CF₃)SMe | CH₂C(O)NMe₂ |
| CH(Me)CH₂CH₂SMe | CH₂C(O)NMe(Et) |
| CH(Et)CH₂CH₂SMe | CH₂C(O)NEt₂ |
| CH₂CH(Me)CH₂SMe | CH₂C(O)NMe(n-Pr) |
| CH₂C(Me)₂CH₂SMe | CH₂C(O)NMe(i-Pr) |
| CH₂CH₂S(O)Me | CH₂C(O)NMe(s-Bu) |
| CH₂CH₂S(O)Et | CH(Me)C(O)NH(Me) |
| CH₂CH₂S(O)(n-Pr) | CH(Me)C(O)NH(Et) |
| CH₂CH₂S(O)(i-Pr) | CH(Me)C(O)NH(n-Pr) |
| CH₂CH₂S(O)(i-Bu) | CH(Me)C(O)NH(i-Pr) |
| CH₂CH(Me)S(O)Me | CH(Me)C(O)NH(n-Bu) |
| CH₂CH(CF₃)S(O)Me | CH(Me)C(O)NH(i-Bu) |
| CH₂C(Me)₂S(O)Me | CH(Me)C(O)NH(s-Bu) |
| CH(Me)CH₂S(O)Me | C(Me)₂C(O)NH(Me) |
| CH(Et)CH₂S(O)Me | C(Me)₂C(O)NH(Et) |
| CH(i-Bu)CH₂S(O)Me | C(Me)₂C(O)NH(n-Pr) |
| CH₂CH₂CH₂S(O)Me | C(Me)₂C(O)NH(i-Pr) |
| CH₂CH₂CH₂S(O)Et | C(Me)₂C(O)NH(n-Bu) |
| CH₂CH₂CH₂S(O)(i-Bu) | C(Me)₂C(O)NH(i-Bu) |
| CH₂CH(Me)CH₂S(O)Me | C(Me)₂C(O)NH(s-Bu) |
| CH₂CH₂CH(CF₃)S(O)Me | CH₂C(O)N(Me)CH₂CH₂F |
| CH(Me)CH₂CH₂S(O)Me | CH₂C(O)N(Me)CH₂CH₂Cl |
| CH(Et)CH₂CH₂S(O)Me | CH₂C(O)N(Me)CH₂CHF₂ |
| CH₂CH(Me)CH₂S(O)Me | CH₂C(O)N(Me)CH₂CF₃ |
| CH₂C(Me)₂CH₂S(O)Me | CH₂C(O)N(Me)CH₂CH₂CH₂F |
| CH₂(2-pyridinyl) | CH₂C(O)N(Me)CH₂CH₂CF₃ |
| CH₂CH₂SO₂Me | CH₂C(O)N(Me)CH₂CF₂CF₃ |
| CH₂CH₂SO₂Et | CH₂C(O)N(Me)CH(Me)CF₃ |
| CH₂CH₂SO₂(n-Pr) | CH₂C(O)N(Me)CH(CF₃)₂ |
| CH₂CH₂SO₂(i-Pr) | CH₂C(O)N(Me)C(Me)₂CF₃ |
| CH₂CH(Me)SO₂Me | CH(Me)C(O)N(Me)CH₂CH₂F |
| CH₂CH(CF₃)SO₂Me | CH(Me)C(O)N(Me)CH₂CH₂Cl |
| CH₂C(Me)²SO₂Me | CH(Me)C(O)N(Me)CH₂CHF₂ |
| CH(Me)CH₂SO₂Me | CH(Me)C(O)N(Me)CH₂CF₃ |
| C(Me)₂CH₂SO₂Me | CH(Me)C(O)N(Me)(CH₂)₂CH₂F |
| CH(Et)CH₂SO₂Me | CH(Me)C(O)N(Me)CH₂CH₂CF₃ |
| CH(i-Pr)CH₂SO₂Me | CH(Me)C(O)N(Me)CH₂CF₂CF₃ |
| CH(i-Bu)CH₂SO₂Me | CH(Me)C(O)N(Me)CH(Me)CF₃ |
| CH₂CH₂CH₂SO₂Me | CH(Me)C(O)N(Me)CH(CF₃)₂ |
| CH₂CH₂CH₂SO₂Et | CH(Me)C(O)N(Me)C(Me)₂CF₃ |
| CH₂CH₂CH(Me)SO₂Me | C(Me)₂C(O)N(Me)CH₂CH₂F |
| CH₂CH₂CH(CF₃)SO₂Me | C(Me)₂C(O)N(Me)CH₂CH₂Cl |
| CH(Me)CH₂CH₂SO₂Me | C(Me)₂C(O)N(Me)CH₂CHF₂ |
| CH(Et)CH₂CH₂SO₂Me | C(Me)₂C(O)N(Me)CH₂CF₃ |
| CH₂CH(Me)CH₂SO₂Me | C(Me)₂C(O)N(Me)CH₂CH₂CH₂F |
| CH₂C(Me)₂CH₂SO₂Me | C(Me)₂C(O)N(Me)CH₂CH₂CF₃ |
| CH₂C(O)NHCH₂F | C(Me)₂C(O)N(Me)CH₂CF₂CF₃ |
| CH₂C(O)NHCH₂Cl | C(Me)₂C(O)N(Me)CH(Me)CF₃ |
| CH₂C(O)NHCH₂CHF₂ | C(Me)₂C(O)N(Me)CH(CF₃)₂ |
| CH₂C(O)NHCH₂CF₃ | C(Me)₂C(O)N(Me)C(Me)₂CF₃ |
| CH₂C(O)NHCH₂CH(Me)F | C(Me)₂C(O)NHCH(Me)CF₃ |
| CH₂C(O)NHCH₂C(Me)₂F | C(Me)₂C(O)NHCH(CF₃)₂ |
| CH₂C(O)NH(CH₂)₂CH₂F | C(Me)₂C(O)NHC(Me)₂CF₃ |
| CH₂C(O)NHCH₂CH₂CF₃ | C(Me)₂C(O)NHCH₂CH(Me)CF₃ |
| CH₂C(O)NHCH₂CHFCF₃ | C(Me)₂C(O)NH(CH₂)₂CF₂CF₃ |
| CH₂C(O)NHCH₂CF₂CF₃ | C(Me)₂C(O)NHCH₂(CF₂)₂CF₃ |
| CH₂C(O)NHCH(Me)CF₃ | C(Me)₂C(O)NHCH(i-Pr)CF₃ |
| CH₂C(O)NHCH(CF₃)₂ | CH(Me)C(O)NH(c-Pr) |
| CH₂C(O)NHC(Me)₂CF₃ | CH(Me)C(O)NH(CH₂-c-Pr) |

R¹ is OCH₂CF₃, R³ is F

| | |
|---|---|
| CH₂CH₂OH | CH₂C(O)NHCH₂CH(Me)CF₃ |
| CH₂CH₂OMe | CH₂C(O)NH(CH₂)₂CF₂CF₃ |
| CH₂CH₂OEt | CH₂C(O)NHCH₂(CF₂)₂CF₃ |

TABLE 3-continued

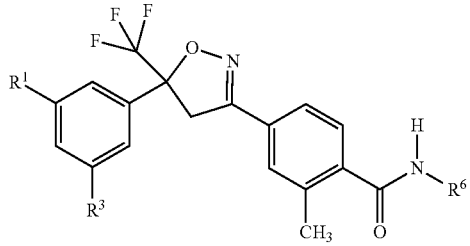

R⁶

| | |
|---|---|
| CH₂CH₂O(i-Pr) | CH(Me)C(O)NHCH₂CH₂F |
| CH₂CH(Me)OH | CH(Me)C(O)NHCH₂CH₂Cl |
| CH₂CH(CF₃)OH | CH(Me)C(O)NHCH₂CHF₂ |
| CH₂C(Me)₂OH | CH(Me)C(O)NHCH₂CF₃ |
| CH₂C(CF₃)(Me)OH | CH(Me)C(O)NHCH₂CH(Me)F |
| CH(Me)CH₂OH | CH(Me)C(O)NHCH₂C(Me)₂F |
| C(Me)₂CH₂OH | CH(Me)C(O)NH(CH₂)₂CH₂F |
| CH(Et)CH₂OH | CH(Me)C(O)NHCH₂CH₂CF₃ |
| CH(i-Pr)CH₂OH | CH(Me)C(O)NHCH₂CHFCF₃ |
| CH(i-Bu)CH₂OH | CH(Me)C(O)NHCH₂CF₂CF₃ |
| CH(Me)CH(CF₃)OH | CH(Me)C(O)NHCH(Me)CF₃ |
| CH₂CH₂CH₂OH | CH(Me)C(O)NHCH(CF₃)₂ |
| CH₂CH₂CH₂OMe | CH(Me)C(O)NHC(Me)₂CF₃ |
| CH₂CH₂CH₂OEt | CH(Me)C(O)NHCH₂CH(Me)CF₃ |
| CH₂CH₂CH(CF₃)OH | CH(Me)C(O)NH(CH₂)₂CF₂CF₃ |
| CH(Me)CH₂CH₂OH | CH(Me)C(O)NHCH₂(CF₂)₂CF₃ |
| CH₂CH(Me)CH₂OH | C(Me)₂C(O)NHCH₂CH₂F |
| CH₂C(Me)₂CH₂OH | C(Me)₂C(O)NHCH₂CH₂Cl |
| CH₂CH₂CH(Me)OH | C(Me)₂C(O)NHCH₂CHF₂ |
| CH₂CH₂C(Me)₂OH | C(Me)₂C(O)NHCH₂CF₃ |
| CH₂CH₂SMe | C(Me)₂C(O)NHCH₂CH(Me)F |
| CH₂CH₂SEt | C(Me)₂C(O)NHCH₂C(Me)₂F |
| CH₂CH₂S(n-Pr) | C(Me)₂C(O)NH(CH₂)₂CH₂F |
| CH₂CH₂S(i-Pr) | C(Me)₂C(O)NHCH₂CH₂CF₃ |
| CH₂CH₂S(i-Bu) | C(Me)₂C(O)NHCH₂CHFCF₃ |
| CH₂CH(Me)SMe | C(Me)₂C(O)NHCH₂CF₂CF₃ |
| CH₂CH(CF₃)SMe | CH₂C(O)NH(c-Pr) |
| CH₂C(Me)₂SMe | CH₂C(O)NH(CH₂-c-Pr) |
| CH(Me)CH₂SMe | CH₂(4-thiazolyl) |
| C(Me)₂CH₂SMe | CH₂C(O)NH(Me) |
| CH(Et)CH₂SMe | CH₂C(O)NH(Et) |
| CH(i-Pr)CH₂SMe | CH₂C(O)NH(n-Pr) |
| CH(i-Bu)CH₂SMe | CH₂C(O)NH(i-Pr) |
| CH₂CH₂CH₂SMe | CH₂C(O)NH(n-Bu) |
| CH₂CH₂CH₂SEt | CH₂C(O)NH(i-Bu) |
| CH₂CH₂CH(Me)SMe | CH₂C(O)NH(s-Bu) |
| CH₂CH₂CH(CF₃)SMe | CH₂C(O)NMe₂ |
| CH(Me)CH₂CH₂SMe | CH₂C(O)NMe(Et) |
| CH(Et)CH₂CH₂SMe | CH₂C(O)NEt₂ |
| CH₂CH(Me)CH₂SMe | CH₂C(O)NMe(n-Pr) |
| CH₂C(Me)₂CH₂SMe | CH₂C(O)NMe(i-Pr) |
| CH₂CH₂S(O)Me | CH₂C(O)NMe(s-Bu) |
| CH₂CH₂S(O)Et | CH(Me)C(O)NH(Me) |
| CH₂CH₂S(O)(n-Pr) | CH(Me)C(O)NH(Et) |
| CH₂CH₂S(O)(i-Pr) | CH(Me)C(O)NH(n-Pr) |
| CH₂CH₂S(O)(i-Bu) | CH(Me)C(O)NH(i-Pr) |
| CH₂CH(Me)S(O)Me | CH(Me)C(O)NH(n-Bu) |
| CH₂CH(CF₃)S(O)Me | CH(Me)C(O)NH(i-Bu) |
| CH₂C(Me)₂S(O)Me | CH(Me)C(O)NH(s-Bu) |
| CH(Me)CH₂S(O)Me | C(Me)₂C(O)NH(Me) |
| CH(Et)CH₂S(O)Me | C(Me)₂C(O)NH(Et) |
| CH(i-Bu)CH₂S(O)Me | C(Me)₂C(O)NH(n-Pr) |
| CH₂CH₂CH₂S(O)Me | C(Me)₂C(O)NH(i-Pr) |
| CH₂CH₂CH₂S(O)Et | C(Me)₂C(O)NH(n-Bu) |
| CH₂CH₂CH₂S(O)(i-Bu) | C(Me)₂C(O)NH(i-Bu) |
| CH₂CH₂CH(Me)S(O)Me | C(Me)₂C(O)NH(s-Bu) |
| CH₂CH₂CH(CF₃)S(O)Me | CH₂C(O)N(Me)CH₂CH₂F |
| CH(Me)CH₂CH₂S(O)Me | CH₂C(O)N(Me)CH₂CH₂Cl |
| CH(Et)CH₂CH₂S(O)Me | CH₂C(O)N(Me)CH₂CHF₂ |
| CH₂CH(Me)CH₂S(O)Me | CH₂C(O)N(Me)CH₂CF₃ |
| CH₂C(Me)₂CH₂S(O)Me | CH₂C(O)N(Me)CH₂CH₂CH₂F |
| CH₂(2-pyridinyl) | CH₂C(O)N(Me)CH₂CH₂CF₃ |
| CH₂CH₂SO₂Me | CH₂C(O)N(Me)CH₂CF₂CF₃ |
| CH₂CH₂SO₂Et | CH₂C(O)N(Me)CH(Me)CF₃ |
| CH₂CH₂SO₂(n-Pr) | CH₂C(O)N(Me)CH(CF₃)₂ |

TABLE 3-continued

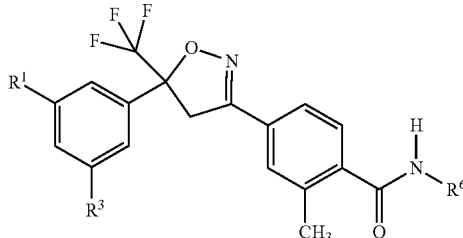

R⁶

| | |
|---|---|
| CH₂CH₂SO₂(i-Pr) | CH₂C(O)N(Me)C(Me)₂CF₃ |
| CH₂CH(Me)SO₂Me | CH(Me)C(O)N(Me)CH₂CH₂F |
| CH₂CH(CF₃)SO₂Me | CH(Me)C(O)N(Me)CH₂CH₂Cl |
| CH₂C(Me)₂SO₂Me | CH(Me)C(O)N(Me)CH₂CHF₂ |
| CH(Me)CH₂SO₂Me | CH(Me)C(O)N(Me)CH₂CF₃ |
| C(Me)₂CH₂SO₂Me | CH(Me)C(O)N(Me)(CH₂)₂CH₂F |
| CH(Et)CH₂SO₂Me | CH(Me)C(O)N(Me)CH₂CH₂CF₃ |
| CH(i-Pr)CH₂SO₂Me | CH(Me)C(O)N(Me)CH₂CF₂CF₃ |
| CH(i-Bu)CH₂SO₂Me | CH(Me)C(O)N(Me)CH(Me)CF₃ |
| CH₂CH₂CH₂SO₂Me | CH(Me)C(O)N(Me)CH(CF₃)₂ |
| CH₂CH₂CH₂SO₂Et | CH(Me)C(O)N(Me)C(Me)₂CF₃ |
| CH₂CH₂CH(Me)SO₂Me | C(Me)₂C(O)N(Me)CH₂CH₂F |
| CH₂CH₂CH(CF₃)SO₂Me | C(Me)₂C(O)N(Me)CH₂CH₂Cl |
| CH(Me)CH₂CH₂SO₂Me | C(Me)₂C(O)N(Me)CH₂CHF₂ |
| CH(Et)CH₂CH₂SO₂Me | C(Me)₂C(O)N(Me)CH₂CF₃ |
| CH₂CH(Me)CH₂SO₂Me | C(Me)₂C(O)N(Me)CH₂CH₂CH₂F |
| CH₂C(Me)₂CH₂SO₂Me | C(Me)₂C(O)N(Me)CH₂CH₂CF₃ |
| CH₂C(O)NHCH₂CH₂F | C(Me)₂C(O)N(Me)CH₂CF₂CF₃ |
| CH₂C(O)NHCH₂CH₂Cl | C(Me)₂C(O)N(Me)CH(Me)CF₃ |
| CH₂C(O)NHCH₂CHF₂ | C(Me)₂C(O)N(Me)CH(CF₃)₂ |
| CH₂C(O)NHCH₂CF₃ | C(Me)₂C(O)N(Me)C(Me)₂CF₃ |
| CH₂C(O)NHCH₂CH(Me)F | C(Me)₂C(O)NHCH(Me)CF₃ |
| CH₂C(O)NHCH₂C(Me)₂F | C(Me)₂C(O)NHCH(CF₃)₂ |
| CH₂C(O)NH(CH₂)₂CH₂F | C(Me)₂C(O)NHC(Me)₂CF₃ |
| CH₂C(O)NHCH₂CH₂CF₃ | C(Me)₂C(O)NHCH₂CH(Me)CF₃ |
| CH₂C(O)NHCH₂CHFCF₃ | C(Me)₂C(O)NH(CH₂)₂CF₂CF₃ |
| CH₂C(O)NHCH₂CF₂CF₃ | C(Me)₂C(O)NHCH₂(CF₂)₂CF₃ |
| CH₂C(O)NHCH(Me)CF₃ | C(Me)₂C(O)NHCH(i-Pr)CF₃ |
| CH₂C(O)NHCH(CF₃)₂ | CH(Me)C(O)NH(c-Pr) |
| CH₂C(O)NHC(Me)₂CF₃ | CH(Me)C(O)NH(CH₂-c-Pr) |

R¹ is OCH₂CF₃, R³ is Cl

| | |
|---|---|
| CH₂CH₂OH | CH₂C(O)NHCH₂CH(Me)CF₃ |
| CH₂CH₂OMe | CH₂C(O)NH(CH₂)₂CF₂CF₃ |
| CH₂CH₂OEt | CH₂C(O)NHCH₂(CF₂)₂CF₃ |
| CH₂CH₂O(i-Pr) | CH(Me)C(O)NHCH₂CH₂F |
| CH₂CH(Me)OH | CH(Me)C(O)NHCH₂CH₂Cl |
| CH₂CH(CF₃)OH | CH(Me)C(O)NHCH₂CHF₂ |
| CH₂C(Me)₂OH | CH(Me)C(O)NHCH₂CF₃ |
| CH₂C(CF₃)(Me)OH | CH(Me)C(O)NHCH₂CH(Me)F |
| CH(Me)CH₂OH | CH(Me)C(O)NHCH₂C(Me)₂F |
| C(Me)₂CH₂OH | CH(Me)C(O)NH(CH₂)₂CH₂F |
| CH(Et)CH₂OH | CH(Me)C(O)NHCH₂CH₂CF₃ |
| CH(i-Pr)CH₂OH | CH(Me)C(O)NHCH₂CHFCF₃ |
| CH(i-Bu)CH₂OH | CH(Me)C(O)NHCH₂CF₂CF₃ |
| CH(Me)CH(CF₃)OH | CH(Me)C(O)NHCH(Me)CF₃ |
| CH₂CH₂CH₂OH | CH(Me)C(O)NHCH(CF₃)₂ |
| CH₂CH₂CH₂OMe | CH(Me)C(O)NHC(Me)₂CF₃ |
| CH₂CH₂CH₂OEt | CH(Me)C(O)NHCH₂CH(Me)CF₃ |
| CH₂CH₂CH(CF₃)OH | CH(Me)C(O)NH(CH₂)₂CF₂CF₃ |
| CH(Me)CH₂CH₂OH | CH(Me)C(O)NHCH₂(CF₂)₂CF₃ |
| CH₂CH(Me)CH₂OH | C(Me)₂C(O)NHCH₂CH₂F |
| CH₂C(Me)₂CH₂OH | C(Me)₂C(O)NHCH₂CH₂Cl |
| CH₂CH₂CH(Me)OH | C(Me)₂C(O)NHCH₂CHF₂ |
| CH₂CH₂C(Me)₂OH | C(Me)₂C(O)NHCH₂CF₃ |
| CH₂CH₂SMe | C(Me)₂C(O)NHCH₂CH(Me)F |
| CH₂CH₂SEt | C(Me)₂C(O)NHCH₂C(Me)₂F |
| CH₂CH₂S(n-Pr) | C(Me)₂C(O)NH(CH₂)₂CH₂F |
| CH₂CH₂S(i-Pr) | C(Me)₂C(O)NHCH₂CH₂CF₃ |
| CH₂CH₂S(i-Bu) | C(Me)₂C(O)NHCH₂CHFCF₃ |
| CH₂CH(Me)SMe | C(Me)₂C(O)NHCH₂CF₂CF₃ |
| CH₂CH(CF₃)SMe | CH₂C(O)NH(c-Pr) |
| CH₂C(Me)₂SMe | CH₂C(O)NH(CH₂-c-Pr) |
| CH(Me)CH₂SMe | CH₂(4-thiazolyl) |
| C(Me)₂CH₂SMe | CH₂C(O)NH(Me) |

TABLE 3-continued

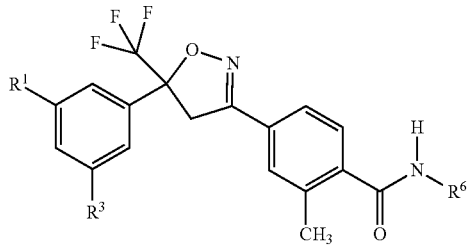

R⁶

| | |
|---|---|
| CH(Et)CH₂SMe | CH₂C(O)NH(Et) |
| CH(i-Pr)CH₂SMe | CH₂C(O)NH(n-Pr) |
| CH(i-Bu)CH₂SMe | CH₂C(O)NH(i-Pr) |
| CH₂CH₂CH₂SMe | CH₂C(O)NH(n-Bu) |
| CH₂CH₂CH₂SEt | CH₂C(O)NH(i-Bu) |
| CH₂CH₂CH(Me)SMe | CH₂C(O)NH(s-Bu) |
| CH₂CH₂CH(CF₃)SMe | CH₂C(O)NMe₂ |
| CH(Me)CH₂CH₂SMe | CH₂C(O)NMe(Et) |
| CH(Et)CH₂CH₂SMe | CH₂C(O)NEt₂ |
| CH₂CH(Me)CH₂SMe | CH₂C(O)NMe(n-Pr) |
| CH₂C(Me)₂CH₂SMe | CH₂C(O)NMe(i-Pr) |
| CH₂CH₂S(O)Me | CH₂C(O)NMe(s-Bu) |
| CH₂CH₂S(O)Et | CH(Me)C(O)NH(Me) |
| CH₂CH₂S(O)(n-Pr) | CH(Me)C(O)NH(Et) |
| CH₂CH₂S(O)(i-Pr) | CH(Me)C(O)NH(n-Pr) |
| CH₂CH₂S(O)(i-Bu) | CH(Me)C(O)NH(i-Pr) |
| CH₂CH(Me)S(O)Me | CH(Me)C(O)NH(n-Bu) |
| CH₂CH(CF₃)S(O)Me | CH(Me)C(O)NH(i-Bu) |
| CH₂C(Me)₂S(O)Me | CH(Me)C(O)NH(s-Bu) |
| CH(Me)CH₂S(O)Me | C(Me)₂C(O)NH(Me) |
| CH(Et)CH₂S(O)Me | C(Me)₂C(O)NH(Et) |
| CH(i-Bu)CH₂S(O)Me | C(Me)₂C(O)NH(n-Pr) |
| CH₂CH₂CH₂S(O)Me | C(Me)₂C(O)NH(i-Pr) |
| CH₂CH₂CH₂S(O)Et | C(Me)₂C(O)NH(n-Bu) |
| CH₂CH₂CH₂S(O)(i-Bu) | C(Me)₂C(O)NH(s-Bu) |
| CH₂CH₂CH(Me)S(O)Me | CH₂C(O)N(Me)CH₂CH₂F |
| CH₂CH₂CH(CF₃)S(O)Me | CH₂C(O)N(Me)CH₂CH₂Cl |
| CH(Me)CH₂CH₂S(O)Me | CH₂C(O)N(Me)CH₂CHF₂ |
| CH(Et)CH₂CH₂S(O)Me | CH₂C(O)N(Me)CH₂CF₃ |
| CH₂CH(Me)CH₂S(O)Me | CH₂C(O)N(Me)CH₂CH₂CH₂F |
| CH₂C(Me)₂CH₂S(O)Me | CH₂C(O)N(Me)CH₂CH₂CF₃ |
| CH₂(2-pyridinyl) | CH₂C(O)N(Me)CH₂CF₂CF₃ |
| CH₂CH₂SO₂Me | CH₂C(O)N(Me)CH(Me)CF₃ |
| CH₂CH₂SO₂Et | CH₂C(O)N(Me)CH(CF₃)₂ |
| CH₂CH₂SO₂(n-Pr) | CH₂C(O)N(Me)C(Me)₂CF₃ |
| CH₂CH₂SO₂(i-Pr) | CH(Me)C(O)N(Me)CH₂CH₂F |
| CH₂CH(Me)SO₂Me | CH(Me)C(O)N(Me)CH₂CH₂Cl |
| CH₂CH(CF₃)SO₂Me | CH(Me)C(O)N(Me)CH₂CHF₂ |
| CH₂C(Me)²SO₂Me | CH(Me)C(O)N(Me)CH₂CF₃ |
| CH(Me)CH₂SO₂Me | CH(Me)C(O)N(Me)CH₂CH₂F |
| C(Me)₂CH₂SO₂Me | CH(Me)C(O)N(Me)(CH₂)₂CH₂F |
| CH(Et)CH₂SO₂Me | CH(Me)C(O)N(Me)CH₂CH₂CF₃ |
| CH(i-Pr)CH₂SO₂Me | CH(Me)C(O)N(Me)CH₂CF₂CF₃ |
| CH(i-Bu)CH₂SO₂Me | CH(Me)C(O)N(Me)CH(Me)CF₃ |
| CH₂CH₂CH₂SO₂Me | CH(Me)C(O)N(Me)CH(CF₃)₂ |
| CH₂CH₂CH₂SO₂Et | CH(Me)C(O)N(Me)C(Me)₂CF₃ |
| CH₂CH₂CH(Me)SO₂Me | C(Me)₂C(O)N(Me)CH₂CH₂F |
| CH₂CH₂CH(CF₃)SO₂Me | C(Me)₂C(O)N(Me)CH₂CH₂Cl |
| CH(Me)CH₂CH₂SO₂Me | C(Me)₂C(O)N(Me)CH₂CHF₂ |
| CH(Et)CH₂CH₂SO₂Me | C(Me)₂C(O)N(Me)CH₂CF₃ |
| CH₂CH(Me)CH₂SO₂Me | C(Me)₂C(O)N(Me)CH₂CH₂CH₂F |
| CH₂C(Me)₂CH₂SO₂Me | C(Me)₂C(O)N(Me)CH₂CH₂CF₃ |
| CH₂C(O)NHCH₂CH₂F | C(Me)₂C(O)N(Me)CH₂CF₂CF₃ |
| CH₂C(O)NHCH₂CH₂Cl | C(Me)₂C(O)N(Me)CH(Me)CF₃ |
| CH₂C(O)NHCH₂CHF₂ | C(Me)₂C(O)N(Me)CH(CF₃)₂ |
| CH₂C(O)NHCH₂CF₃ | C(Me)₂C(O)N(Me)C(Me)₂CF₃ |
| CH₂C(O)NHCH₂CH(Me)F | C(Me)₂C(O)NHCH(Me)CF₃ |
| CH₂C(O)NHCH₂C(Me)₂F | C(Me)₂C(O)NHCH(CF₃)₂ |
| CH₂C(O)NHCH₂(CH₂)₂CH₂F | C(Me)₂C(O)NHC(Me)₂CF₃ |
| CH₂C(O)NHCH₂CHFCF₃ | C(Me)₂C(O)NHCH₂CH(Me)CF₃ |
| CH₂C(O)NHCH₂CF₂CF₃ | C(Me)₂C(O)NH(CH₂)₂CF₂CF₃ |
| CH₂C(O)NHCH(Me)CF₃ | C(Me)₂C(O)NHCH(i-Pr)CF₃ |
| CH₂C(O)NHCH(CF₃)₂ | CH(Me)C(O)NH(c-Pr) |
| CH₂C(O)NHC(Me)₂CF₃ | CH(Me)C(O)NH(CH₂-c-Pr) |

TABLE 3-continued

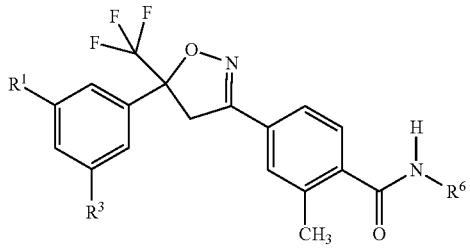

R⁶

| R¹ is OCH₂CF₃, R³ is Br | |
|---|---|
| CH₂CH₂OH | CH₂C(O)NHCH₂CH(Me)CF₃ |
| CH₂CH₂OMe | CH₂C(O)NH(CH₂)₂CF₂CF₃ |
| CH₂CH₂OEt | CH₂C(O)NHCH₂(CF₂)₂CF₃ |
| CH₂CH₂O(i-Pr) | CH(Me)C(O)NHCH₂CH₂F |
| CH₂CH(Me)OH | CH(Me)C(O)NHCH₂CH₂Cl |
| CH₂CH(CF₃)OH | CH(Me)C(O)NHCH₂CHF₂ |
| CH₂C(Me)₂OH | CH(Me)C(O)NHCH₂CF₃ |
| CH₂C(CF₃)(Me)OH | CH(Me)C(O)NHCH₂CH(Me)F |
| CH(Me)CH₂OH | CH(Me)C(O)NHCH₂C(Me)₂F |
| C(Me)₂CH₂OH | CH(Me)C(O)NH(CH₂)₂CH₂F |
| CH(Et)CH₂OH | CH(Me)C(O)NHCH₂CH₂CF₃ |
| CH(i-Pr)CH₂OH | CH(Me)C(O)NHCH₂CHFCF₃ |
| CH(i-Bu)CH₂OH | CH(Me)C(O)NHCH₂CF₂CF₃ |
| CH(Me)CH(CF₃)OH | CH(Me)C(O)NHCH(Me)CF₃ |
| CH₂CH₂CH₂OH | CH(Me)C(O)NHCH(CF₃)₂ |
| CH₂CH₂CH₂OMe | CH(Me)C(O)NHC(Me)₂CF₃ |
| CH₂CH₂CH₂OEt | CH(Me)C(O)NHCH₂CH(Me)CF₃ |
| CH₂CH₂CH(CF₃)OH | CH(Me)C(O)NH(CH₂)₂CF₂CF₃ |
| CH(Me)CH₂CH₂OH | CH(Me)C(O)NHCH₂(CF₂)₂CF₃ |
| CH(Me)CH(Me)CH₂OH | C(Me)₂C(O)NHCH₂CH₂F |
| CH₂C(Me)₂CH₂OH | C(Me)₂C(O)NHCH₂CH₂Cl |
| CH₂CH₂CH(Me)OH | C(Me)₂C(O)NHCH₂CHF₂ |
| CH₂C(Me)₂OH | C(Me)₂C(O)NHCH₂CF₃ |
| CH₂CH₂SMe | C(Me)₂C(O)NHCH(Me)F |
| CH₂CH₂SEt | C(Me)₂C(O)NHCH₂C(Me)₂F |
| CH₂CH₂S(n-Pr) | C(Me)₂C(O)NH(CH₂)₂CH₂F |
| CH₂CH₂S(i-Pr) | C(Me)₂C(O)NHCH₂CH₂CF₃ |
| CH₂CH₂S(i-Bu) | C(Me)₂C(O)NHCHFCF₃ |
| CH₂CH(Me)SMe | C(Me)₂C(O)NHCH₂CF₂CF₃ |
| CH₂CH(CF₃)SMe | CH₂C(O)NH(c-Pr) |
| CH₂C(Me)₂SMe | CH₂C(O)NH(CH₂-c-Pr) |
| CH(Me)CH₂SMe | CH₂(4-thiazolyl) |
| C(Me)₂CH₂SMe | CH₂C(O)NH(Me) |
| CH(Et)CH₂SMe | CH₂C(O)NH(Et) |
| CH(i-Pr)CH₂SMe | CH₂C(O)NH(n-Pr) |
| CH(i-Bu)CH₂SMe | CH₂C(O)NH(i-Pr) |
| CH₂CH₂CH₂SMe | CH₂C(O)NH(n-Bu) |
| CH₂CH₂CH₂SEt | CH₂C(O)NH(i-Bu) |
| CH₂CH₂CH(Me)SMe | CH₂C(O)NH(s-Bu) |
| CH₂CH₂CH(CF₃)SMe | CH₂C(O)NMe₂ |
| CH(Me)CH₂CH₂SMe | CH₂C(O)NMe(Et) |
| CH(Et)CH₂CH₂SMe | CH₂C(O)NEt₂ |
| CH₂CH(Me)CH₂SMe | CH₂C(O)NMe(n-Pr) |
| CH₂C(Me)₂CH₂SMe | CH₂C(O)NMe(i-Pr) |
| CH₂CH₂S(O)Me | CH₂C(O)NMe(s-Bu) |
| CH₂CH₂S(O)Et | CH(Me)C(O)NH(Me) |
| CH₂CH₂S(O)(n-Pr) | CH(Me)C(O)NH(Et) |
| CH₂CH₂S(O)(i-Pr) | CH(Me)C(O)NH(n-Pr) |
| CH₂CH₂S(O)(i-Bu) | CH(Me)C(O)NH(i-Pr) |
| CH₂CH(Me)S(O)Me | CH(Me)C(O)NH(n-Bu) |
| CH₂CH(CF₃)S(O)Me | CH(Me)C(O)NH(i-Bu) |
| CH₂C(Me)₂S(O)Me | CH(Me)C(O)NH(s-Bu) |
| CH(Me)CH₂S(O)Me | C(Me)₂C(O)NH(Me) |
| CH(Et)CH₂S(O)Me | C(Me)₂C(O)NH(Et) |
| CH(i-Bu)CH₂S(O)Me | C(Me)₂C(O)NH(n-Pr) |
| CH₂CH₂CH₂S(O)Me | C(Me)₂C(O)NH(i-Pr) |
| CH₂CH₂CH₂S(O)Et | C(Me)₂C(O)NH(n-Bu) |
| CH₂CH₂CH₂S(O)(i-Bu) | C(Me)₂C(O)NH(s-Bu) |
| CH₂CH₂CH(Me)S(O)Me | C(Me)₂C(O)N(Me)CH₂CH₂F |
| CH₂CH₂CH(CF₃)S(O)Me | CH₂C(O)N(Me)CH₂CH₂Cl |
| CH(Me)CH₂CH₂S(O)Me | CH₂C(O)N(Me)CH₂CHF₂ |
| CH(Et)CH₂CH₂S(O)Me | CH₂C(O)N(Me)CH₂CF₃ |
| CH₂CH(Me)CH₂S(O)Me | CH₂C(O)N(Me)CH₂CF₃ |

TABLE 3-continued

[Structure: isoxazoline with CF2 group (top), R1 and R3 on phenyl, CH3 on benzamide, N-R6]

| R⁶ | |
|---|---|
| CH₂C(Me)₂CH₂S(O)Me | CH₂C(O)N(Me)CH₂CH₂CH₂F |
| CH₂(2-pyridinyl) | CH₂C(O)N(Me)CH₂CH₂CF₃ |
| CH₂CH₂SO₂Me | CH₂C(O)N(Me)CH₂CF₂CF₃ |
| CH₂CH₂SO₂Et | CH₂C(O)N(Me)CH(Me)CF₃ |
| CH₂CH₂SO₂(n-Pr) | CH₂C(O)N(Me)CH(CF₃)₂ |
| CH₂CH₂SO₂(i-Pr) | CH₂C(O)N(Me)C(Me)₂CF₃ |
| CH₂CH(Me)SO₂Me | CH(Me)C(O)N(Me)CH₂CH₂F |
| CH₂CH(CF₃)SO₂Me | CH(Me)C(O)N(Me)CH₂CH₂Cl |
| CH₂C(Me)₂SO₂Me | CH(Me)C(O)N(Me)CH₂CHF₂ |
| CH(Me)CH₂SO₂Me | CH(Me)C(O)N(Me)CH₂CF₃ |
| C(Me)₂CH₂SO₂Me | CH(Me)C(O)N(Me)(CH₂)₂CH₂F |
| CH(Et)CH₂SO₂Me | CH(Me)C(O)N(Me)CH₂CH₂CF₃ |
| CH(i-Pr)CH₂SO₂Me | CH(Me)C(O)N(Me)CH₂CF₂CF₃ |
| CH(i-Bu)CH₂SO₂Me | CH(Me)C(O)N(Me)CH(Me)CF₃ |
| CH₂CH₂CH₂SO₂Me | CH(Me)C(O)N(Me)CH(CF₃)₂ |
| CH₂CH₂CH₂SO₂Et | CH(Me)C(O)N(Me)C(Me)₂CF₃ |
| CH₂CH₂CH(Me)SO₂Me | C(Me)₂C(O)N(Me)CH₂CH₂F |
| CH₂CH₂CH(CF₃)SO₂Me | C(Me)₂C(O)N(Me)CH₂CH₂Cl |
| CH(Me)CH₂CH₂SO₂Me | C(Me)₂C(O)N(Me)CH₂CHF₂ |
| CH(Et)CH₂CH₂SO₂Me | C(Me)₂C(O)N(Me)CH₂CF₃ |
| CH₂CH(Me)CH₂SO₂Me | C(Me)₂C(O)N(Me)(CH₂)₂CH₂F |
| CH₂C(Me)₂CH₂SO₂Me | C(Me)₂C(O)N(Me)CH₂CH₂CF₃ |
| CH₂C(O)NHCH₂CH₂F | C(Me)₂C(O)N(Me)CH₂CF₂CF₃ |
| CH₂C(O)NHCH₂CH₂Cl | C(Me)₂C(O)N(Me)CH(Me)CF₃ |
| CH₂C(O)NHCH₂CHF₂ | C(Me)₂C(O)N(Me)CH(CF₃)₂ |
| CH₂C(O)NHCH₂CF₃ | C(Me)₂C(O)N(Me)C(Me)₂CF₃ |
| CH₂C(O)NHCH₂CH(Me)F | C(Me)₂C(O)NHCH(Me)CF₃ |
| CH₂C(O)NHCH₂C(Me)₂F | C(Me)₂C(O)NHCH(CF₃)₂ |
| CH₂C(O)NH(CH₂)₂CH₂F | C(Me)₂C(O)NHC(Me)₂CF₃ |
| CH₂C(O)NHCH₂CH₂CF₃ | C(Me)₂C(O)NHCH₂CH(Me)CF₃ |
| CH₂C(O)NHCH₂CHFCF₃ | C(Me)₂C(O)NH(CH₂)₂CF₂CF₃ |
| CH₂C(O)NHCH₂CF₂CF₃ | C(Me)₂C(O)NHCH(CF₂)₂CF₃ |
| CH₂C(O)NHCH(Me)CF₃ | C(Me)₂C(O)NHCH(i-Pr)CF₃ |
| CH₂C(O)NHCH(CF₃)₂ | CH(Me)C(O)NH(c-Pr) |
| CH₂C(O)NHC(Me)₂CF₃ | CH(Me)C(O)NH(CH₂-c-Pr) |

TABLE 4

[Structure: isoxazoline with CF2 group, R1 and R3 on phenyl, Me on benzamide, N-R6]

| R⁶ | |
|---|---|
| R¹ is Cl, R³ is Cl | |
| CH₂CH₂SMe | CH(Me)C(O)NH(Et) |
| CH₂CH₂SEt | CH(Me)C(O)NH(n-Pr) |
| CH₂CH₂S(n-Pr) | CH(Me)C(O)NH(i-Pr) |
| CH₂CH₂CH₂SMe | CH(Me)C(O)NH(i-Bu) |
| CH₂CH₂CH₂SEt | CH(Me)C(O)NH(s-Bu) |
| CH₂CH₂S(O)Me | CH₂(4-thiazolyl) |
| CH₂CH₂S(O)Et | CH₂C(O)N(Me)CH₂CF₃ |

TABLE 4-continued

[Structure: isoxazoline with CF2 group, R1 and R3 on phenyl, Me on benzamide, N-R6]

| R⁶ | |
|---|---|
| CH₂CH₂S(O)(n-Pr) | CH(Me)C(O)N(Me)CH₂CF₃ |
| CH₂CH₂CH₂S(O)Me | CH₂C(O)NH(c-Pr) |
| CH₂CH₂CH₂S(O)Et | CH₂C(O)NH(CH₂-c-Pr) |
| CH₂CH₂SO₂Me | CH₂C(O)NHCH₂CH₂Cl |
| CH₂CH₂SO₂Et | CH₂C(O)NHCH₂CHF₂ |
| CH₂CH₂SO₂(n-Pr) | CH₂C(O)NHCH₂CF₃ |
| CH₂CH₂CH₂SO₂Me | CH₂C(O)NHCH₂CH₂CF₃ |
| CH₂CH₂CH₂SO₂Et | CH₂C(O)NHCH(Me)CF₃ |
| CH₂(2-pyridinyl) | CH₂C(O)NHCH₂CH(Me)CF₃ |
| CH₂C(O)NH₂ | CH(Me)C(O)NH(c-Pr) |
| CH₂C(O)NH(Me) | CH(Me)C(O)NH(CH₂-c-Pr) |
| CH₂C(O)NH(Et) | CH(Me)C(O)NHCH₂CH₂Cl |
| CH₂C(O)NH(n-Pr) | CH(Me)C(O)NHCH₂CHF₂ |
| CH₂C(O)NH(i-Pr) | CH(Me)C(O)NHCH₂CF₃ |
| CH₂C(O)NH(i-Bu) | CH(Me)C(O)NHCH₂CH₂CF₃ |
| CH₂C(O)NH(s-Bu) | CH(Me)C(O)NHCH(Me)CF₃ |
| CH(Me)C(O)NH(Me) | CH(Me)C(O)NHCH₂CH(Me)CF₃ |
| R¹ is Br, R³ is Br | |
| CH₂CH₂SMe | CH(Me)C(O)NH(Et) |
| CH₂CH₂SEt | CH(Me)C(O)NH(n-Pr) |
| CH₂CH₂S(n-Pr) | CH(Me)C(O)NH(i-Pr) |
| CH₂CH₂CH₂SMe | CH(Me)C(O)NH(i-Bu) |
| CH₂CH₂CH₂SEt | CH(Me)C(O)NH(s-Bu) |
| CH₂CH₂S(O)Me | CH₂(4-thiazolyl) |
| CH₂CH₂S(O)Et | CH₂C(O)N(Me)CH₂CF₃ |
| CH₂CH₂S(O)(n-Pr) | CH(Me)C(O)N(Me)CH₂CF₃ |
| CH₂CH₂CH₂S(O)Me | CH₂C(O)NH(c-Pr) |
| CH₂CH₂CH₂S(O)Et | CH₂C(O)NH(CH₂-c-Pr) |
| CH₂CH₂SO₂Me | CH₂C(O)NHCH₂CH₂Cl |
| CH₂CH₂SO₂Et | CH₂C(O)NHCH₂CHF₂ |
| CH₂CH₂SO₂(n-Pr) | CH₂C(O)NHCH₂CF₃ |
| CH₂CH₂CH₂SO₂Me | CH₂C(O)NHCH₂CH₂CF₃ |
| CH₂CH₂CH₂SO₂Et | CH₂C(O)NHCH(Me)CF₃ |
| CH₂(2-pyridinyl) | CH₂C(O)NHCH₂CH(Me)CF₃ |
| CH₂C(O)NH₂ | CH(Me)C(O)NH(c-Pr) |
| CH₂C(O)NH(Me) | CH(Me)C(O)NH(CH₂-c-Pr) |
| CH₂C(O)NH(Et) | CH(Me)C(O)NHCH₂CH₂Cl |
| CH₂C(O)NH(n-Pr) | CH(Me)C(O)NHCH₂CHF₂ |
| CH₂C(O)NH(i-Pr) | CH(Me)C(O)NHCH₂CF₃ |
| CH₂C(O)NH(i-Bu) | CH(Me)C(O)NHCH₂CH₂CF₃ |
| CH₂C(O)NH(s-Bu) | CH(Me)C(O)NHCH(Me)CF₃ |
| CH(Me)C(O)NH(Me) | CH(Me)C(O)NHCH₂CH(Me)CF₃ |
| R¹ is CF₃, R³ is H | |
| CH₂CH₂SMe | CH(Me)C(O)NH(Et) |
| CH₂CH₂SEt | CH(Me)C(O)NH(n-Pr) |
| CH₂CH₂S(n-Pr) | CH(Me)C(O)NH(i-Pr) |
| CH₂CH₂CH₂SMe | CH(Me)C(O)NH(i-Bu) |
| CH₂CH₂CH₂SEt | CH(Me)C(O)NH(s-Bu) |
| CH₂CH₂S(O)Me | CH₂(4-thiazolyl) |
| CH₂CH₂S(O)Et | CH₂C(O)N(Me)CH₂CF₃ |
| CH₂CH₂S(O)(n-Pr) | CH(Me)C(O)N(Me)CH₂CF₃ |
| CH₂CH₂CH₂S(O)Me | CH₂C(O)NH(c-Pr) |
| CH₂CH₂CH₂S(O)Et | CH₂C(O)NH(CH₂-c-Pr) |
| CH₂CH₂SO₂Me | CH₂C(O)NHCH₂CH₂Cl |
| CH₂CH₂SO₂Et | CH₂C(O)NHCH₂CHF₂ |
| CH₂CH₂SO₂(n-Pr) | CH₂C(O)NHCH₂CF₃ |
| CH₂CH₂CH₂SO₂Me | CH₂C(O)NHCH₂CH₂CF₃ |
| CH₂CH₂CH₂SO₂Et | CH₂C(O)NHCH(Me)CF₃ |
| CH₂(2-pyridinyl) | CH₂C(O)NHCH₂CH(Me)CF₃ |
| CH₂C(O)NH₂ | CH(Me)C(O)NH(c-Pr) |
| CH₂C(O)NH(Me) | CH(Me)C(O)NH(CH₂-c-Pr) |
| CH₂C(O)NH(Et) | CH(Me)C(O)NHCH₂CH₂Cl |

TABLE 4-continued

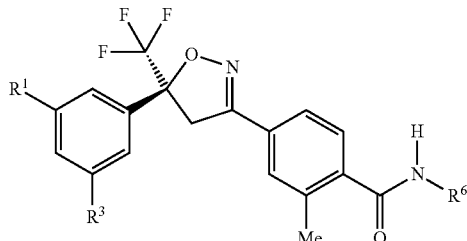

| R⁶ | |
|---|---|
| CH₂C(O)NH(n-Pr) | CH(Me)C(O)NHCH₂CHF₂ |
| CH₂C(O)NH(i-Pr) | CH(Me)C(O)NHCH₂CF₃ |
| CH₂C(O)NH(i-Bu) | CH(Me)C(O)NHCH₂CH₂CF₃ |
| CH₂C(O)NH(s-Bu) | CH(Me)C(O)NHCH(Me)CF₃ |
| CH(Me)C(O)NH(Me) | CH(Me)C(O)NHCH₂CH(Me)CF₃ |

R¹ is CF₃, R³ is F

| | |
|---|---|
| CH₂CH₂SMe | CH(Me)C(O)NH(Et) |
| CH₂CH₂SEt | CH(Me)C(O)NH(n-Pr) |
| CH₂CH₂S(n-Pr) | CH(Me)C(O)NH(i-Pr) |
| CH₂CH₂CH₂SMe | CH(Me)C(O)NH(i-Bu) |
| CH₂CH₂CH₂SEt | CH(Me)C(O)NH(s-Bu) |
| CH₂CH₂S(O)Me | CH₂(4-thiazolyl) |
| CH₂CH₂S(O)Et | CH₂C(O)N(Me)CH₂CF₃ |
| CH₂CH₂S(O)(n-Pr) | CH(Me)C(O)N(Me)CH₂CF₃ |
| CH₂CH₂CH₂S(O)Me | CH₂C(O)NH(c-Pr) |
| CH₂CH₂CH₂S(O)Et | CH₂C(O)NH(CH₂-c-Pr) |
| CH₂CH₂SO₂Me | CH₂C(O)NHCH₂CH₂Cl |
| CH₂CH₂SO₂Et | CH₂C(O)NHCH₂CHF₂ |
| CH₂CH₂SO₂(n-Pr) | CH₂C(O)NHCH₂CF₃ |
| CH₂CH₂CH₂SO₂Me | CH₂C(O)NHCH₂CH₂CF₃ |
| CH₂CH₂CH₂SO₂Et | CH₂C(O)NHCH(Me)CF₃ |
| CH₂(2-pyridinyl) | CH₂C(O)NHCH₂CH(Me)CF₃ |
| CH₂C(O)NH₂ | CH(Me)C(O)NH(c-Pr) |
| CH₂C(O)NH(Me) | CH(Me)C(O)NH(CH₂-c-Pr) |
| CH₂C(O)NH(Et) | CH(Me)C(O)NHCH₂CH₂Cl |
| CH₂C(O)NH(n-Pr) | CH(Me)C(O)NHCH₂CHF₂ |
| CH₂C(O)NH(i-Pr) | CH(Me)C(O)NHCH₂CF₃ |
| CH₂C(O)NH(i-Bu) | CH(Me)C(O)NHCH₂CH₂CF₃ |
| CH₂C(O)NH(s-Bu) | CH(Me)C(O)NHCH(Me)CF₃ |
| CH(Me)C(O)NH(Me) | CH(Me)C(O)NHCH₂CH(Me)CF₃ |

R¹ is CF₃, R³ is Cl

| | |
|---|---|
| CH₂CH₂SMe | CH(Me)C(O)NH(Et) |
| CH₂CH₂SEt | CH(Me)C(O)NH(n-Pr) |
| CH₂CH₂S(n-Pr) | CH(Me)C(O)NH(i-Pr) |
| CH₂CH₂CH₂SMe | CH(Me)C(O)NH(i-Bu) |
| CH₂CH₂CH₂SEt | CH(Me)C(O)NH(s-Bu) |
| CH₂CH₂S(O)Me | CH₂(4-thiazolyl) |
| CH₂CH₂S(O)Et | CH₂C(O)N(Me)CH₂CF₃ |
| CH₂CH₂S(O)(n-Pr) | CH(Me)C(O)N(Me)CH₂CF₃ |
| CH₂CH₂CH₂S(O)Me | CH₂C(O)NH(c-Pr) |
| CH₂CH₂CH₂S(O)Et | CH₂C(O)NH(CH₂-c-Pr) |
| CH₂CH₂SO₂Me | CH₂C(O)NHCH₂CH₂Cl |
| CH₂CH₂SO₂Et | CH₂C(O)NHCH₂CHF₂ |
| CH₂CH₂SO₂(n-Pr) | CH₂C(O)NHCH₂CF₃ |
| CH₂CH₂CH₂SO₂Me | CH₂C(O)NHCH₂CH₂CF₃ |
| CH₂CH₂CH₂SO₂Et | CH₂C(O)NHCH(Me)CF₃ |
| CH₂(2-pyridinyl) | CH₂C(O)NHCH₂CH(Me)CF₃ |
| CH₂C(O)NH₂ | CH(Me)C(O)NH(c-Pr) |
| CH₂C(O)NH(Me) | CH(Me)C(O)NH(CH₂-c-Pr) |
| CH₂C(O)NH(Et) | CH(Me)C(O)NHCH₂CH₂Cl |
| CH₂C(O)NH(n-Pr) | CH(Me)C(O)NHCH₂CHF₂ |
| CH₂C(O)NH(i-Pr) | CH(Me)C(O)NHCH₂CF₃ |
| CH₂C(O)NH(i-Bu) | CH(Me)C(O)NHCH₂CH₂CF₃ |
| CH₂C(O)NH(s-Bu) | CH(Me)C(O)NHCH(Me)CF₃ |
| CH(Me)C(O)NH(Me) | CH(Me)C(O)NHCH₂CH(Me)CF₃ |

R¹ is CF₃, R³ is Br

| | |
|---|---|
| CH₂CH₂SMe | CH(Me)C(O)NH(Et) |
| CH₂CH₂SEt | CH(Me)C(O)NH(n-Pr) |
| CH₂CH₂S(n-Pr) | CH(Me)C(O)NH(i-Pr) |
| CH₂CH₂CH₂SMe | CH(Me)C(O)NH(i-Bu) |
| CH₂CH₂CH₂SEt | CH(Me)C(O)NH(s-Bu) |

TABLE 4-continued

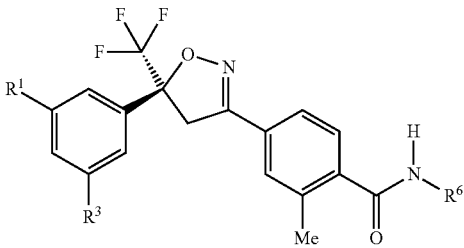

| R⁶ | |
|---|---|
| CH₂CH₂S(O)Me | CH₂(4-thiazolyl) |
| CH₂CH₂S(O)Et | CH₂C(O)N(Me)CH₂CF₃ |
| CH₂CH₂S(O)(n-Pr) | CH(Me)C(O)N(Me)CH₂CF₃ |
| CH₂CH₂CH₂S(O)Me | CH₂C(O)NH(c-Pr) |
| CH₂CH₂CH₂S(O)Et | CH₂C(O)NH(CH₂-c-Pr) |
| CH₂CH₂SO₂Me | CH₂C(O)NHCH₂CH₂Cl |
| CH₂CH₂SO₂Et | CH₂C(O)NHCH₂CHF₂ |
| CH₂CH₂SO₂(n-Pr) | CH₂C(O)NHCH₂CF₃ |
| CH₂CH₂CH₂SO₂Me | CH₂C(O)NHCH₂CH₂CF₃ |
| CH₂CH₂CH₂SO₂Et | CH₂C(O)NHCH(Me)CF₃ |
| CH₂(2-pyridinyl) | CH₂C(O)NHCH₂CH(Me)CF₃ |
| CH₂C(O)NH₂ | CH(Me)C(O)NH(c-Pr) |
| CH₂C(O)NH(Me) | CH(Me)C(O)NH(CH₂-c-Pr) |
| CH₂C(O)NH(Et) | CH(Me)C(O)NHCH₂CH₂Cl |
| CH₂C(O)NH(n-Pr) | CH(Me)C(O)NHCH₂CHF₂ |
| CH₂C(O)NH(i-Pr) | CH(Me)C(O)NHCH₂CF₃ |
| CH₂C(O)NH(i-Bu) | CH(Me)C(O)NHCH₂CH₂CF₃ |
| CH₂C(O)NH(s-Bu) | CH(Me)C(O)NHCH(Me)CF₃ |
| CH(Me)C(O)NH(Me) | CH(Me)C(O)NHCH₂CH(Me)CF₃ |

R¹ is CF₃, R³ is CF₃

| | |
|---|---|
| CH₂CH₂SMe | CH(Me)C(O)NH(Et) |
| CH₂CH₂SEt | CH(Me)C(O)NH(n-Pr) |
| CH₂CH₂S(n-Pr) | CH(Me)C(O)NH(i-Pr) |
| CH₂CH₂CH₂SMe | CH(Me)C(O)NH(i-Bu) |
| CH₂CH₂CH₂SEt | CH(Me)C(O)NH(s-Bu) |
| CH₂CH₂S(O)Me | CH₂(4-thiazolyl) |
| CH₂CH₂S(O)Et | CH₂C(O)N(Me)CH₂CF₃ |
| CH₂CH₂S(O)(n-Pr) | CH(Me)C(O)N(Me)CH₂CF₃ |
| CH₂CH₂CH₂S(O)Me | CH₂C(O)NH(c-Pr) |
| CH₂CH₂CH₂S(O)Et | CH₂C(O)NH(CH₂-c-Pr) |
| CH₂CH₂SO₂Me | CH₂C(O)NHCH₂CH₂Cl |
| CH₂CH₂SO₂Et | CH₂C(O)NHCH₂CHF₂ |
| CH₂CH₂SO₂(n-Pr) | CH₂C(O)NHCH₂CF₃ |
| CH₂CH₂CH₂SO₂Me | CH₂C(O)NHCH₂CH₂CF₃ |
| CH₂CH₂CH₂SO₂Et | CH₂C(O)NHCH(Me)CF₃ |
| CH₂(2-pyridinyl) | CH₂C(O)NHCH₂CH(Me)CF₃ |
| CH₂C(O)NH₂ | CH(Me)C(O)NH(c-Pr) |
| CH₂C(O)NH(Me) | CH(Me)C(O)NH(CH₂-c-Pr) |
| CH₂C(O)NH(Et) | CH(Me)C(O)NHCH₂CH₂Cl |
| CH₂C(O)NH(n-Pr) | CH(Me)C(O)NHCH₂CHF₂ |
| CH₂C(O)NH(i-Pr) | CH(Me)C(O)NHCH₂CF₃ |
| CH₂C(O)NH(i-Bu) | CH(Me)C(O)NHCH₂CH₂CF₃ |
| CH₂C(O)NH(s-Bu) | CH(Me)C(O)NHCH(Me)CF₃ |
| CH(Me)C(O)NH(Me) | CH(Me)C(O)NHCH₂CH(Me)CF₃ |

R¹ is OCF₃, R³ is Cl

| | |
|---|---|
| CH₂CH₂SMe | CH(Me)C(O)NH(Et) |
| CH₂CH₂SEt | CH(Me)C(O)NH(n-Pr) |
| CH₂CH₂S(n-Pr) | CH(Me)C(O)NH(i-Pr) |
| CH₂CH₂CH₂SMe | CH(Me)C(O)NH(i-Bu) |
| CH₂CH₂CH₂SEt | CH(Me)C(O)NH(s-Bu) |
| CH₂CH₂S(O)Me | CH₂(4-thiazolyl) |
| CH₂CH₂S(O)Et | CH₂C(O)N(Me)CH₂CF₃ |
| CH₂CH₂S(O)(n-Pr) | CH(Me)C(O)N(Me)CH₂CF₃ |
| CH₂CH₂CH₂S(O)Me | CH₂C(O)NH(c-Pr) |
| CH₂CH₂CH₂S(O)Et | CH₂C(O)NH(CH₂-c-Pr) |
| CH₂CH₂SO₂Me | CH₂C(O)NHCH₂CH₂Cl |
| CH₂CH₂SO₂Et | CH₂C(O)NHCH₂CHF₂ |
| CH₂CH₂SO₂(n-Pr) | CH₂C(O)NHCH₂CF₃ |
| CH₂CH₂CH₂SO₂Me | CH₂C(O)NHCH₂CH₂CF₃ |
| CH₂CH₂CH₂SO₂Et | CH₂C(O)NHCH(Me)CF₃ |
| CH₂(2-pyridinyl) | CH₂C(O)NHCH₂CH(Me)CF₃ |
| CH₂C(O)NH₂ | CH(Me)C(O)NH(c-Pr) |

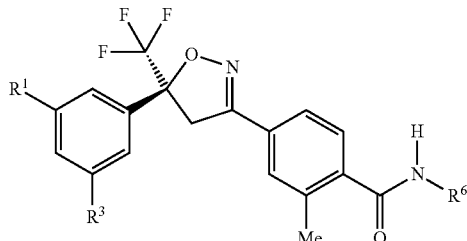

| $R^6$ | |
|---|---|
| CH₂C(O)NH(Me) | CH(Me)C(O)NH(CH₂-c-Pr) |
| CH₂C(O)NH(Et) | CH(Me)C(O)NHCH₂CH₂Cl |
| CH₂C(O)NH(n-Pr) | CH(Me)C(O)NHCH₂CHF₂ |
| CH₂C(O)NH(i-Pr) | CH(Me)C(O)NHCH₂CF₃ |
| CH₂C(O)NH(i-Bu) | CH(Me)C(O)NHCH₂CH₂CF₃ |
| CH₂C(O)NH(s-Bu) | CH(Me)C(O)NHCH(Me)CF₃ |
| CH(Me)C(O)NH(Me) | CH(Me)C(O)NHCH₂CH(Me)CF₃ |
| $R^1$ is OCH₂CF₃, $R^3$ is F | |
| CH₂CH₂SMe | CH(Me)C(O)NH(Et) |
| CH₂CH₂SEt | CH(Me)C(O)NH(n-Pr) |
| CH₂CH₂S(n-Pr) | CH(Me)C(O)NH(i-Pr) |
| CH₂CH₂CH₂SMe | CH(Me)C(O)NH(i-Bu) |
| CH₂CH₂CH₂SEt | CH(Me)C(O)NH(s-Bu) |
| CH₂CH₂S(O)Me | CH₂(4-thiazolyl) |
| CH₂CH₂S(O)Et | CH₂C(O)N(Me)CH₂CF₃ |
| CH₂CH₂S(O)(n-Pr) | CH(Me)C(O)N(Me)CH₂CF₃ |
| CH₂CH₂CH₂S(O)Me | CH₂C(O)NH(c-Pr) |
| CH₂CH₂CH₂S(O)Et | CH₂C(O)NH(CH₂-c-Pr) |
| CH₂CH₂SO₂Me | CH₂C(O)NHCH₂CH₂Cl |
| CH₂CH₂SO₂Et | CH₂C(O)NHCH₂CHF₂ |
| CH₂CH₂SO₂(n-Pr) | CH₂C(O)NHCH₂CF₃ |
| CH₂CH₂CH₂SO₂Me | CH₂C(O)NHCH₂CH₂CF₃ |
| CH₂CH₂CH₂SO₂Et | CH₂C(O)NHCH(Me)CF₃ |
| CH₂(2-pyridinyl) | CH₂C(O)NHCH₂CH(Me)CF₃ |
| CH₂C(O)NH₂ | CH(Me)C(O)NH(c-Pr) |
| CH₂C(O)NH(Me) | CH(Me)C(O)NH(CH₂-c-Pr) |
| CH₂C(O)NH(Et) | CH(Me)C(O)NHCH₂CH₂Cl |
| CH₂C(O)NH(n-Pr) | CH(Me)C(O)NHCH₂CHF₂ |
| CH₂C(O)NH(i-Pr) | CH(Me)C(O)NHCH₂CF₃ |
| CH₂C(O)NH(i-Bu) | CH(Me)C(O)NHCH₂CH₂CF₃ |
| CH₂C(O)NH(s-Bu) | CH(Me)C(O)NHCH(Me)CF₃ |
| CH(Me)C(O)NH(Me) | CH(Me)C(O)NHCH₂CH(Me)CF₃ |
| $R^1$ is OCH₂CF₃, $R^3$ is Cl | |
| CH₂CH₂SMe | CH(Me)C(O)NH(Et) |
| CH₂CH₂SEt | CH(Me)C(O)NH(n-Pr) |
| CH₂CH₂S(n-Pr) | CH(Me)C(O)NH(i-Pr) |
| CH₂CH₂CH₂SMe | CH(Me)C(O)NH(i-Bu) |
| CH₂CH₂CH₂SEt | CH(Me)C(O)NH(s-Bu) |
| CH₂CH₂S(O)Me | CH₂(4-thiazolyl) |
| CH₂CH₂S(O)Et | CH₂C(O)N(Me)CH₂CF₃ |
| CH₂CH₂S(O)(n-Pr) | CH(Me)C(O)N(Me)CH₂CF₃ |
| CH₂CH₂CH₂S(O)Me | CH₂C(O)NH(c-Pr) |
| CH₂CH₂CH₂S(O)Et | CH₂C(O)NH(CH₂-c-Pr) |
| CH₂CH₂SO₂Me | CH₂C(O)NHCH₂CH₂Cl |
| CH₂CH₂SO₂Et | CH₂C(O)NHCH₂CHF₂ |
| CH₂CH₂SO₂(n-Pr) | CH₂C(O)NHCH₂CF₃ |
| CH₂CH₂CH₂SO₂Me | CH₂C(O)NHCH₂CH₂CF₃ |
| CH₂CH₂CH₂SO₂Et | CH₂C(O)NHCH(Me)CF₃ |
| CH₂(2-pyridinyl) | CH₂C(O)NHCH₂CH(Me)CF₃ |
| CH₂C(O)NH₂ | CH(Me)C(O)NH(c-Pr) |
| CH₂C(O)NH(Me) | CH(Me)C(O)NH(CH₂-c-Pr) |
| CH₂C(O)NH(Et) | CH(Me)C(O)NHCH₂CH₂Cl |
| CH₂C(O)NH(n-Pr) | CH(Me)C(O)NHCH₂CHF₂ |
| CH₂C(O)NH(i-Pr) | CH(Me)C(O)NHCH₂CF₃ |
| CH₂C(O)NH(i-Bu) | CH(Me)C(O)NHCH₂CH₂CF₃ |
| CH₂C(O)NH(s-Bu) | CH(Me)C(O)NHCH(Me)CF₃ |
| CH(Me)C(O)NH(Me) | CH(Me)C(O)NHCH₂CH(Me)CF₃ |
| $R^1$ is OCH₂CF₃, $R^3$ is Br | |
| CH₂CH₂SMe | CH(Me)C(O)NH(Et) |
| CH₂CH₂SEt | CH(Me)C(O)NH(n-Pr) |
| CH₂CH₂S(n-Pr) | CH(Me)C(O)NH(i-Pr) |

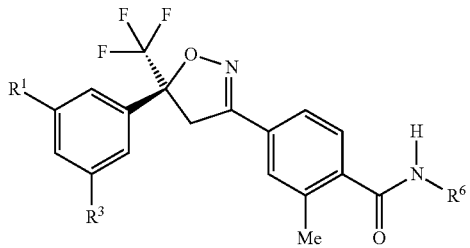

| $R^6$ | |
|---|---|
| CH₂CH₂CH₂SMe | CH(Me)C(O)NH(i-Bu) |
| CH₂CH₂CH₂SEt | CH(Me)C(O)NH(s-Bu) |
| CH₂CH₂S(O)Me | CH₂(4-thiazolyl) |
| CH₂CH₂S(O)Et | CH₂C(O)N(Me)CH₂CF₃ |
| CH₂CH₂S(O)(n-Pr) | CH(Me)C(O)N(Me)CH₂CF₃ |
| CH₂CH₂CH₂S(O)Me | CH₂C(O)NH(c-Pr) |
| CH₂CH₂CH₂S(O)Et | CH₂C(O)NH(CH₂-c-Pr) |
| CH₂CH₂SO₂Me | CH₂C(O)NHCH₂CH₂Cl |
| CH₂CH₂SO₂Et | CH₂C(O)NHCH₂CHF₂ |
| CH₂CH₂SO₂(n-Pr) | CH₂C(O)NHCH₂CF₃ |
| CH₂CH₂CH₂SO₂Me | CH₂C(O)NHCH₂CH₂CF₃ |
| CH₂CH₂CH₂SO₂Et | CH₂C(O)NHCH(Me)CF₃ |
| CH₂(2-pyridinyl) | CH₂C(O)NHCH₂CH(Me)CF₃ |
| CH₂C(O)NH₂ | CH(Me)C(O)NH(c-Pr) |
| CH₂C(O)NH(Me) | CH(Me)C(O)NH(CH₂-c-Pr) |
| CH₂C(O)NH(Et) | CH(Me)C(O)NHCH₂CH₂Cl |
| CH₂C(O)NH(n-Pr) | CH(Me)C(O)NHCH₂CHF₂ |
| CH₂C(O)NH(i-Pr) | CH(Me)C(O)NHCH₂CF₃ |
| CH₂C(O)NH(i-Bu) | CH(Me)C(O)NHCH₂CH₂CF₃ |
| CH₂C(O)NH(s-Bu) | CH(Me)C(O)NHCH(Me)CF₃ |
| CH(Me)C(O)NH(Me) | CH(Me)C(O)NHCH₂CH(Me)CF₃ |

Compositions of Formula 1 compounds may also contain formulation auxiliaries and additives, known to those skilled in the art as formulation aids (some of which may be considered to also function as solid diluents, liquid diluents or surfactants). Such formulation auxiliaries and additives may control: pH (buffers), foaming during processing (antifoams such polyorganosiloxanes), sedimentation of active ingredients (suspending agents), viscosity (thixotropic thickeners), in-container microbial growth (antimicrobials), product freezing (antifreezes), color (dyes/pigment dispersions), wash-off (film formers or stickers), evaporation (evaporation retardants), and other formulation attributes. Film formers include, for example, polyvinyl acetates, polyvinyl acetate copolymers, polyvinylpyrrolidone-vinyl acetate copolymer, polyvinyl alcohols, polyvinyl alcohol copolymers and waxes. Examples of formulation auxiliaries and additives include those listed in *McCutcheon's Volume 2: Functional Materials*, annual International and North American editions published by McCutcheon's Division, The Manufacturing Confectioner Publishing Co.; and PCT Publication WO 03/024222.

Of note is the present method using a combination of a compound of Formula 1 with at least one other parasitic invertebrate pest control active ingredient. Of particular note is such a method where the other parasitic invertebrate pest control active ingredient has a different site of action from the compound of Formula 1. In certain instances, a combination with at least one other parasitic invertebrate pest control active ingredient having a similar spectrum of control but a different site of action will be particularly advantageous for resistance management. Thus, a composition comprising a compound of Formula 1 useful in the present method can further comprise a biologically effective amount of at least one additional parasitic invertebrate pest control active ingredient having a similar spectrum of control but a different site of action.

The compounds of Formula 1 can be applied without other adjuvants, but most often application will be of a formulation comprising one or more active ingredients with suitable carriers, diluents, and surfactants and possibly in combination with a food depending on the contemplated end use. One method of application involves spraying a water dispersion or refined oil solution of a compound of Formula 1. Combinations with spray oils, spray oil concentrates, spreader stickers, adjuvants, other solvents, and synergists such as piperonyl butoxide often enhance compound efficacy. Such sprays can be applied from spray containers such as a can, a bottle or other container, either by means of a pump or by releasing it from a pressurized container, e.g., a pressurized aerosol spray can. Such spray compositions can take various forms, for example, sprays, mists, foams, fumes or fog. Such spray compositions thus can further comprise propellants, foaming agents, etc. as the case may be. Of note is a spray composition comprising a biologically effective amount of a compound or a composition of Formula 1 and a carrier. One embodiment of such a spray composition comprises a biologically effective amount of a compound or a composition of Formula 1 and a propellant. Representative propellants include, but are not limited to, methane, ethane, propane, butane, isobutane, butene, pentane, isopentane, neopentane, pentene, hydrofluorocarbons, chlorofluorocarbons, dimethyl ether, and mixtures of the foregoing. Of note is a spray composition (and a method utilizing such a spray composition dispensed from a spray container) used to control at least one parasitic invertebrate pest selected from the group consisting of mosquitoes, black flies, stable flies, deer flies, horse flies, wasps, yellow jackets, hornets, ticks, spiders, ants, gnats, and the like, including individually or in combinations.

The controlling of animal parasites includes controlling external parasites that are parasitic to the surface of the body of the host animal (e.g., shoulders, armpits, abdomen, inner part of the thighs) and internal parasites that are parasitic to the inside of the body of the host animal (e.g., stomach, intestine, lung, veins, under the skin, lymphatic tissue). External parasitic or disease transmitting pests include, for example, chiggers, ticks, lice, mosquitoes, flies, mites and fleas. Internal parasites include heartworms, hookworms and helminths. Compounds and compositions of Formula 1 are particularly suitable for combating external parasitic pests. Compounds and compositions of Formula 1 are suitable for systemic and/or non-systemic control of infestation or infection by parasites on animals.

Compounds and compositions of Formula 1 are suitable for combating parasitic invertebrate pests that infest animal subjects including those in the wild, livestock and agricultural working animals. Livestock is the term used to refer (singularly or plurally) to a domesticated animal intentionally reared in an agricultural setting to make produce such as food or fiber, or for its labor; examples of livestock include cattle, sheep, goats, horses, pigs, donkeys, camels, buffalo, rabbits, hens, turkeys, ducks and geese (e.g., raised for meat, milk, butter, eggs, fur, leather, feathers and/or wool). By combating parasites, fatalities and performance reduction (in terms of meat, milk, wool, skins, eggs, etc.) are reduced, so that applying a composition comprising a compound of Formula 1 allows more economic and simple husbandry of animals.

Compounds and compositions of Formula 1 are especially suitable for combating parasitic invertebrate pests that infest companion animals and pets (e.g., dogs, cats, pet birds and aquarium fish), research and experimental animals (e.g., hamsters, guinea pigs, rats and mice), as well as animals raised for/in zoos, wild habitats and/or circuses.

In an embodiment of this invention, the animal is preferably a vertebrate, and more preferably a mammal, avian or fish. In a particular embodiment, the animal subject is a mammal (including great apes, such as humans). Other mammalian subjects include primates (e.g., monkeys), bovine (e.g., cattle or dairy cows), porcine (e.g., hogs or pigs), ovine (e.g., goats or sheep), equine (e.g., horses), canine (e.g., dogs), feline (e.g., house cats), camels, deer, donkeys, buffalos, antelopes, rabbits, and rodents (e.g., guinea pigs, squirrels, rats, mice, gerbils, and hamsters). Avians include Anatidae (swans, ducks and geese), Columbidae (e.g., doves and pigeons), Phasianidae (e.g., partridges, grouse and turkeys), Thesienidae (e.g., domestic chickens), Psittacines (e.g., parakeets, macaws, and parrots), game birds, and ratites (e.g., ostriches).

Birds treated or protected by the compounds of Formula 1 can be associated with either commercial or noncommercial aviculture. These include Anatidae, such as swans, geese, and ducks, Columbidae, such as doves and domestic pigeons, Phasianidae, such as partridge, grouse and turkeys, Thesienidae, such as domestic chickens, and Psittacines, such as parakeets, macaws and parrots raised for the pet or collector market, among others.

For purposes of the present invention, the term "fish" shall be understood to include without limitation, the Teleosti grouping of fish, i.e., teleosts. Both the Salmoniformes order (which includes the Salmonidae family) and the Perciformes order (which includes the Centrarchidae family) are contained within the Teleosti grouping. Examples of potential fish recipients include the Salmonidae, Serranidae, Sparidae, Cichlidae, and Centrarchidae, among others.

Other animals are also contemplated to benefit from the inventive methods, including marsupials (such as kangaroos), reptiles (such as farmed turtles), and other economically important domestic animals for which the inventive methods are safe and effective in treating or preventing parasite infection or infestation.

Examples of parasitic invertebrate pests controlled by administering a pesticidally effective amount of a compound of Formula 1 to an animal to be protected include ectoparasites (arthropods, acarines, etc.) and endoparasites (helminths, e.g., nematodes, trematodes, cestodes, acanthocephalans, etc.).

The disease or group of diseases described generally as helminthiasis is due to infection of an animal host with parasitic worms known as helminths. The term 'helminths' is meant to include nematodes, trematodes, cestodes and acanthocephalans. Helminthiasis is a prevalent and serious economic problem with domesticated animals such as swine, sheep, horses, cattle, goats, dogs, cats and poultry.

Among the helminths, the group of worms described as nematodes causes widespread and at times serious infection in various species of animals. Nematodes that are contemplated to be treated by the compounds of this invention and by the inventive methods include, without limitation, the following genera: *Acanthocheilonema, Aelurostrongylus, Ancylostoma, Angiostrongylus, Ascaridia, Ascaris, Brugia, Bunostomum, Capillaria, Chabertia, Cooperia, Crenosoma, Dictyocaulus, Dioctophyme, Dipetalonema, Diphyllobothrium, Dirofilaria, Dracunculus, Enterobius, Filaroides, Haemonchus, eterakis, Lagochilascaris, Loa, Mansonella, Muellerius, Necator, Nematodirus, Oesophagostomum, Ostertagia, Oxyuris, Parafilaria, Parascaris, Physaloptera,*

*Protostrongylus, Setaria, Spirocerca, Stephanofilaria, Strongyloides, Strongylus, Thelazia, Toxascaris, Toxocara, Trichinella, Trichonema, Trichostrongylus, Trichuris, Uncinaria* and *Wuchereria*.

Of the above, the most common genera of nematodes infecting the animals referred to above are *Haemonchus, Trichostrongylus, Ostertagia, Nematodirus, Cooperia, Ascaris, Bunostomum, Oesophagostomum, Chabertia, Trichuris, Strongylus, Trichonema, Dictyocaulus, Capillaria, Heterakis, Toxocara, Ascaridia, Oxyuris, Ancylostoma, Uncinaria, Toxascaris* and *Parascaris*. Certain of these, such as *Nematodirus, Cooperia* and *Oesophagostomum* attack primarily the intestinal tract while others, such as *Haemonchus* and *Ostertagia*, are more prevalent in the stomach while others such as *Dictyocaulus* are found in the lungs. Still other parasites may be located in other tissues such as the heart and blood vessels, subcutaneous and lymphatic tissue and the like.

Trematodes that are contemplated to be treated by the compounds of this invention and by the inventive methods include, without limitation, the following genera: *Alaria, Fasciola, Nanophyetus, Opisthorchis, Paragonimus* and *Schistosoma*.

Cestodes that are contemplated to be treated by the compounds of this invention and by the inventive methods include, without limitation, the following genera: *Diphyllobothrium, Diplydium, Spirometra* and *Taenia*.

The most common genera of parasites of the gastrointestinal tract of humans are *Ancylostoma, Necator, Ascaris, Strongyloides, Trichinella, Capillaria, Trichuris* and *Enterobius*. Other medically important genera of parasites which are found in the blood or other tissues and organs outside the gastrointestinal tract are the filarial worms such as *Wuchereria, Brugia, Onchocerca* and *Loa*, as well as *Dracunculus* and extra intestinal stages of the intestinal worms *Strongyloides* and *Trichinella*.

Numerous other helminth genera and species are known to the art, and are also contemplated to be treated by the compounds of Formula 1. These are enumerated in great detail in *Textbook of Veterinary Clinical Parasitology, Volume 1, Helminths*, E. J. L. Soulsby, F. A. Davis Co., Philadelphia, Pa.; *Helminths, Arthropods and Protozoa*, (6$^{th}$ Edition of Monnig's Veterinary Helminthology and Entomology), E. J. L. Soulsby, The Williams and Wilkins Co., Baltimore, Md.

The compounds of Formula 1 are effective against a number of animal ectoparasites (e.g., arthropod ectoparasites of mammals and birds).

Insect and acarine pests include, e.g., biting insects such as flies and mosquitoes, mites, ticks, lice, fleas, true bugs, parasitic maggots, and the like.

Adult flies include, e.g., the horn fly or *Haematobia irritans*, the horse fly or *Tabanus* spp., the stable fly or *Stomoxys calcitrans*, the black fly or *Simulium* spp., the deer fly or *Chrysops* spp., the louse fly or *Melophagus ovinus*, and the tsetse fly or *Glossina* spp. Parasitic fly maggots include, e.g., the bot fly (*Oestrus ovis* and *Cuterebra* spp.), the blow fly or *Phaenicia* spp., the screwworm or *Cochliomyia hominivorax*, the cattle grub or *Hypoderma* spp., the fleeceworm and the *Gastrophilus* of horses. Mosquitoes include, for example, *Culex* spp., *Anopheles* spp. and *Aedes* spp.

Mites include *Mesostigmata* spp. e.g., mesostigmatids such as the chicken mite, *Dermanyssus gallinae*; itch or scab mites such as *Sarcoptidae* spp. for example, *Sarcoptes scabiei*; mange mites such as *Psoroptidae* spp. including *Chorioptes bovis* and *Psoroptes ovis*; chiggers e.g., *Trombiculidae* spp. for example the North American chigger, *Trombicula alfreddugesi*.

Ticks include, e.g., soft-bodied ticks including *Argasidae* spp. for example *Argas* spp. and *Ornithodoros* spp.; hard-bodied ticks including *Ixodidae* spp., for example *Rhipicephalus sanguineus, Dermacentor variabilis, Dermacentor andersoni, Amblyomma americanum, Ixodes scapularis* and other *Rhipicephalus* spp. (including the former *Boophilus* genera).

Lice include, e.g., sucking lice, e.g., *Menopon* spp. and *Bovicola* spp.; biting lice, e.g., *Haematopinus* spp., *Linognathus* spp. and *Solenopotes* spp.

Fleas include, e.g., *Ctenocephalides* spp., such as dog flea (*Ctenocephalides canis*) and cat flea (*Ctenocephalides felis*); *Xenopsylla* spp. such as oriental rat flea (*Xenopsylla cheopis*); and *Pulex* spp. such as human flea (*Pulex irritans*).

True bugs include, e.g., *Cimicidae* or e.g., the common bed bug (*Cimex lectularius*); *Triatominae* spp. including triatomid bugs also known as kissing bugs; for example *Rhodnius prolixus* and *Triatoma* spp.

Generally, flies, fleas, lice, mosquitoes, gnats, mites, ticks and helminths cause tremendous losses to the livestock and companion animal sectors. Arthropod parasites also are a nuisance to humans and can vector disease-causing organisms in humans and animals.

Numerous other parasitic invertebrate pests are known to the art, and are also contemplated to be treated by the compounds of Formula 1. These are enumerated in great detail in *Medical and Veterinary Entomology*, D. S. Kettle, John Wiley & Sons, New York and Toronto; *Control of Arthropod Pests of Livestock: A Review of Technology*, R. O. Drummand, J. E. George, and S. E. Kunz, CRC Press, Boca Raton, Fla.

In particular, the compounds of Formula 1 are especially effective against ectoparasites including *Stomoxys calcitrans* (stable fly); ticks such as *Ixodes* spp., *Boophilus* spp., *Rhipicephalus* spp., *Amblyomma* spp., *Dermacentor* spp., *Hyalomma* spp. and *Haemaphysalis* spp.; and fleas such as *Ctenocephalides felis* (cat flea) and *Ctenocephalides canis* (dog flea).

The compounds of Formula 1 may also be effective against ectoparasites including: flies such as *Haematobia (Lyperosia) irritans* (horn fly), *Simulium* spp. (blackfly), *Glossina* spp. (tsetse flies), *Hydrotaea irritans* (head fly), *Musca autumnalis* (face fly), *Musca domestica* (house fly), *Morellia simplex* (sweat fly), *Tabanus* spp. (horse fly), *Hypoderma bovis, Hypoderma lineatum, Lucilia sericata, Lucilia cuprina* (green blowfly), *Calliphora* spp. (blowfly), *Protophormia* spp., *Oestrus ovis* (nasal botfly), *Culicoides* spp. (midges), *Hippobosca equine, Gastrophilus intestinalis, Gastrophilus haemorrhoidalis* and *Gastrophilus nasalis*; lice such as *Bovicola (Damalinia) bovis, Bovicola equi, Haematopinus asini, Felicola subrostratus, Heterodoxus spiniger, Lignonathus setosus* and *Trichodectes canis*; keds such as *Melophagus ovinus*; and mites such as *Psoroptes* spp., *Sarcoptes scabei, Chorioptes bovis, Demodex equi, Cheyletiella* spp., *Notoedres cati, Trombicula* spp. and *Otodectes cyanotis* (ear mites).

Other biologically active compounds or agents may be administered at the same or different times as the compounds of Formula 1. Such compounds, for example, may be useful adjuncts in Formula 1 compositions for the present method. As noted below, such biologically active compounds may be included in the composition of Formula 1. Such biologically active compounds for use in the present invention include the organophosphate pesticides. This class of pesticides has very broad activity as insecticides and, in certain instances, anthelminitic activity. Organophosphate pesticides include, e.g., dicrotophos, terbufos, dimethoate, diazinon, disulfoton, trichlorfon, azinphos-methyl, chlorpyrifos, malathion, oxydemeton-methyl, methamidophos, acephate, ethyl parathion, methyl parathion, mevinphos, phorate, carbofenthion and phosalone. Compositions of Formula 1 compounds for the present method are also comtemplated to include carbamate-type pesticides, including, e.g., carbaryl, carbofuran, aldicarb, molinate, methomyl, carbofuran, etc., as well as combinations with the organochlorine type pesticides. Compositions of Formula 1 compounds are further contemplated to include combinations with biological pesticides, including repellents, the pyrethrins (as well as synthetic variations thereof, e.g., allethrin, resmethrin, permethrin, tralomethrin), and nicotine, that is often employed as an acaricide. Other contemplated combinations are with miscellaneous pesticides including: *Bacillus thuringiensis*, chlorobenzilate, formamidines (e.g., amitraz), copper compounds (e.g., copper hydroxide and cupric oxychloride sulfate), cyfluthrin, cypermethrin, dicofol, endosulfan, esfenvalerate, fenvalerate, lambda-cyhalothrin, methoxychlor and sulfur.

Of note are additional biologically active compounds or agents selected from art-known anthelmintics, such as, for example, avermectins (e.g., ivermectin, moxidectin, milbemycin), benzimidazoles (e.g., albendazole, triclabendazole), salicylanilides (e.g., closantel, oxyclozanide), substituted phenols (e.g., nitroxynil), pyrimidines (e.g., pyrantel), imidazothiazoles (e.g., levamisole) and praziquantel.

Other biologically active compounds or agents useful in the Formula 1 compositions for the present method can be selected from Insect Growth Regulators (IGRs) and Juvenile Hormone Analogues (JHAs) such as diflubenzuron, triflumuron, fluazuron, cyromazine, methoprene, etc., thereby providing both initial and sustained control of parasites (at all stages of insect development, including eggs) on the animal subject, as well as within the environment of the animal subject.

Of note are biologically active compounds or agents useful in the Formula 1 compositions for the present method selected from the avermectin class of antiparasitic compounds. As stated above, the avermectin family of compounds includes very potent antiparasitic agents known to be useful against a broad spectrum of endoparasites and ectoparasites in mammals.

A preferred compound for use within the scope of the present invention is ivermectin. Ivermectin is a semi-synthetic derivative of avermectin and is generally produced as a mixture of at least 80% 22,23-dihydroavermectin $B_{1a}$ and less than 20% 22,23-dihydroavermectin $B_{1b}$. Ivermectin is disclosed in U.S. Pat. No. 4,199,569.

Abamectin is an avermectin that is disclosed as avermectin $B_{1a}/B_{1b}$ in U.S. Pat. No. 4,310,519. Abamectin contains at least 80% of avermectin $B_{1a}$ and not more than 20% of avermectin $B_{1b}$.

Another preferred avermectin is doramectin, also known as 25-cyclohexyl-avermectin $B_1$. The structure and preparation of doramectin is disclosed in U.S. Pat. No. 5,089,480.

Another preferred avermectin is moxidectin. Moxidectin, also known as LL-F28249 alpha, is known from U.S. Pat. No. 4,916,154.

Another preferred avermectin is selamectin. Selamectin is 25-cyclohexyl-25-de(1-methylpropyl)-5-deoxy-22,23-dihydro-5-(hydroxyimino)-avermectin $B_1$ monosaccharide.

Milbemycin, or B41, is a substance which is isolated from the fermentation broth of a milbemycin-producing strain of *Streptomyces*. The microorganism, the fermentation conditions and the isolation procedures are described in U.S. Pat. Nos. 3,950,360 and 3,984,564.

Emamectin (4"-deoxy-4"-epi-methylaminoavermectin $B_1$), which can be prepared as described in U.S. Pat. Nos. 5,288,710 and 5,399,717, is a mixture of two homologues, 4"-deoxy-4"-epi-methylaminoavermectin $B_{1a}$ and 4"-deoxy-4"-epi-methylaminoavermectin $B_{1b}$. Preferably, a salt of emamectin is used. Non-limiting examples of salts of emamectin which may be used in the present invention include the salts described in U.S. Pat. No. 5,288,710, e.g., salts derived from benzoic acid, substituted benzoic acid, benzenesulfonic acid, citric acid, phosphoric acid, tartaric acid, maleic acid, and the like. Most preferably, the emamectin salt used in the present invention is emamectin benzoate.

Eprinomectin is chemically known as 4"-epi-acetylamino-4"-deoxy-avermectin $B_1$. Eprinomectin was specifically developed to be used in all cattle classes and age groups. It was the first avermectin to show broad-spectrum activity against both endo- and ecto-parasites while also leaving minimal residues in meat and milk. It has the additional advantage of being highly potent when delivered topically.

The Formula 1 compositions for the present method optionally comprise combinations of one or more of the following antiparasite compounds: imidazo[1,2-b]pyridazine compounds as described by U.S. Patent Application Publication No. 2005/0182059 A1; 1-(4-mono and di-halomethylsulphonylphenyl)-2-acylamino-3-fluoropropanol compounds, as described by U.S. Pat. No. 7,361,689; trifluoromethanesulfonanilide oxime ether derivatives, as described by U.S. Pat. No. 7,312,248; and n-[(phenyloxy)phenyl]-1,1,1-trifluoromethane sulfonamide and n-[(phenylsulfanyl)phenyl]-1,1,1-trifluoromethane-sulfonamide derivatives, as described by PCT Patent Application Publication WO 2006/135648.

The Formula 1 compositions may also further comprise a flukicide. Suitable flukicides include, for example, triclabendazole, fenbendazole, albendazole, clorsulon and oxibendazole. It will be appreciated that the above combinations may further include combinations of antibiotic, antiparasitic and anti-fluke active compounds.

In addition to the above combinations, it is also contemplated to provide Formula 1 compositions, as described herein for the present method, with other animal health remedies such as trace elements, anti-inflammatories, anti-infectives, hormones, dermatological preparations, including antiseptics and disinfectants, and immunobiologicals such as vaccines and antisera for the prevention of disease.

For example, such antinfectives include one or more antibiotics that are optionally co-administered during treatment using the inventive methods, e.g., in a combined composition and/or in separate dosage forms. Art-known antibiotics suitable for this purpose include, for example, those listed herein below.

One useful antibiotic is florfenicol, also known as D-(threo)-1-(4-methylsulfonylphenyl)-2-dichloroacetamido-3-fluoro-1-propanol. Another preferred antibiotic compound is D-(threo)-1-(4-methylsulfonylphenyl)-2-difluoroacetamido-3-fluoro-1-propanol. Another useful antibiotic is thiamphenicol. Processes for the manufacture of these antibiotic compounds, and intermediates useful in such processes, are described in U.S. Pat. Nos. 4,31,857; 4,582,918; 4,973,750; 4,876,352; 5,227,494; 4,743,700; 5,567,844; 5,105,009; 5,382,673; 5,352,832; and 5,663,361. Other florfenicol analogs and/or prodrugs have been disclosed and such analogs also can be used in the compositions and methods of the present invention (see e.g., U.S. Pat. Nos. 7,041,670 and 7,153,842).

Another useful antibiotic compound is tilmicosin. Tilmicosin is a macrolide antibiotic that is chemically defined as 20-dihydro-20-deoxy-20-(cis-3,5-dimethylpiperidin-1-yl)-desmycosin and is disclosed in U.S. Pat. No. 4,820,695.

Another useful antibiotic for use in the present invention is tulathromycin. Tulathromycin may be prepared in accordance with the procedures set forth in U.S. Pat. No. 6,825,327.

Further antibiotics for use in the present invention include the cephalosporins such as, for example, ceftiofur, cefquinome, etc. The concentration of the cephalosporin in the formulation of the present invention optionally varies between about 1 mg/mL to 500 mg/mL.

Another useful antibiotic includes the fluoroquinolones, such as, for example, enrofloxacin, danofloxacin, difloxacin, orbifloxacin and marbofloxacin. In the case of enrofloxacin, it may be administered in a concentration of about 100 mg/mL. Danofloxacin may be present in a concentration of about 180 mg/mL.

Other useful macrolide antibiotics include compounds from the class of ketolides, or, more specifically, the azalides. Such compounds are described in, for example, U.S. Pat. Nos. 6,514,945; 6,472,371; 6,270,768; 6,437,151; 6,271,255; 6,239,12; 5,958,888; 6,339,063; and 6,054,434.

Other useful antibiotics include the tetracyclines, particularly chlortetracycline and oxytetracycline. Other antibiotics may include β-lactams such as penicillins, e.g., penicillin, ampicillin, amoxicillin, or a combination of amoxicillin with clavulanic acid or other beta lactamase inhibitors.

Treatments of the invention are by conventional means such as by enteral administration in the form of, for example, tablets, capsules, drinks, drenching preparations, granulates, pastes, boli, feed-through procedures, or suppositories; or by parenteral administration, such as, for example, by injection (including intramuscular, subcutaneous, intravenous, intraperitoneal) or implants; or by nasal administration.

The compounds of Formula 1 may be administered in a controlled release form, for example in subcutaneous or orally adminstered slow release formulations.

Typically a parasiticidal composition according to the present invention comprises a mixture of a compound of Formula 1, an N-oxide or a salt thereof, with one or more pharmaceutically or veterinarily acceptable carriers comprising excipients and auxiliaries selected with regard to the intended route of administration (e.g., oral or parenteral administration such as injection) and in accordance with standard practice. In addition, a suitable carrier is selected on the basis of compatibility with the one or more active ingredients in the composition, including such considerations as stability relative to pH and moisture content. Therefore of note is a composition for protecting an animal from an invertebrate parasitic pest comprising a parasitically effective amount of a compound of Formula 1 and at least one carrier.

For parenteral administration including intravenous, intramuscular and subcutaneous injection, a compound of Formula 1 can be formulated in suspension, solution or emulsion in oily or aqueous vehicles, and may contain adjuncts such as suspending, stabilizing and/or dispersing agents. The compounds of Formula 1 may also be formulated for bolus injection or continuous infusion. Pharmaceutical compositions for injection include aqueous solutions of water-soluble forms of active ingredients (e.g., a salt of an active compound), preferably in physiologically compatible buffers containing other excipients or auxiliaries as are known in the art of pharmaceutical formulation. Additionally, suspensions of the active compounds may be prepared in a lipophilic vehicle. Suitable lipophilic vehicles include fatty oils such as sesame oil, synthetic fatty acid esters such as ethyl oleate and triglycerides, or materials such as liposomes. Aqueous injection suspensions may contain substances that increase the viscosity of the suspension, such as sodium carboxymethyl cellulose, sorbitol, or dextran. Formulations for injection may be presented in unit dosage form, e.g., in ampoules or in multi-dose containers. Alternatively, the active ingredient may be in powder form for constitution with a suitable vehicle, e.g., sterile, pyrogen-free water, before use.

In addition to the formulations described supra, the compounds of Formula 1 may also be formulated as a depot preparation. Such long acting formulations may be administered by implantation (for example, subcutaneously or intramuscularly) or by intramuscular or subcutaneous injection. The compounds of Formula 1 may be formulated for this route of administration with suitable polymeric or hydrophobic materials (for instance, in an emulsion with a pharmacologically acceptable oil), with ion exchange resins, or as a sparingly soluble derivative such as, without limitation, a sparingly soluble salt.

For administration by inhalation, the compounds of Formula 1 can be delivered in the form of an aerosol spray using a pressurized pack or a nebulizer and a suitable propellant, e.g., without limitation, dichlorodifluoromethane, trichlorofluoromethane, dichlorotetrafluoroethane or carbon dioxide. In the case of a pressurized aerosol, the dosage unit may be controlled by providing a valve to deliver a metered amount. Capsules and cartridges of, for example, gelatin for use in an inhaler or insufflator may be formulated containing a powder mix of the compound and a suitable powder base such as lactose or starch.

Compounds of Formula 1 have been discovered to have surprisingly favorable pharmacokinetic and pharmacodynamic properties providing systemic availability from oral administration and ingestion. Therefore after ingestion by the animal to be protected, parasiticidally effective concentrations of compounds of Formula 1 in the bloodstream protect the treated animal from blood-sucking pests such as fleas, ticks and lice. Therefore of note is a composition for protecting an animal from an invertebrate parasite pest in a form for oral administration (i.e. comprising, in addition to a parasiticidally effective amount of a compound of Formula 1, one or more carriers selected from binders and fillers suitable for oral administration and feed concentrate carriers).

For oral administration in the form of solutions (the most readily available form for absorption), emulsions, suspensions, pastes, gels, capsules, tablets, boluses, powders, granules, rumen-retention and feed/water/lick blocks, a compound of Formula 1 can be formulated with binders/fillers known in the art to be suitable for oral administration compositions, such as sugars and sugar derivatives (e.g., lactose, sucrose, mannitol, sorbitol), starch (e.g., maize starch, wheat starch, rice starch, potato starch), cellulose and derivatives (e.g., methylcellulose, carboxymethylcellulose, ethylhydroxycellulose), protein derivatives (e.g., zein, gelatin), and synthetic polymers (e.g., polyvinyl alcohol, polyvinylpyrrolidone). If desired, lubricants (e.g., magnesium stearate), disintegrating agents (e.g., cross-linked polyvinylpyrrolidinone, agar, alginic acid) and dyes or pigments can be added. Pastes and gels often also contain adhesives (e.g., acacia, alginic acid, bentonite, cellulose, xanthan gum, colloidal magnesium aluminum silicate) to aid in keeping the composition in contact with the oral cavity and not being easily ejected.

A preferred embodiment is a composition of the present method formulated into a chewable and/or edible product (e.g., a chewable treat or edible tablet). Such a product would ideally have a taste, texture and/or aroma favored by the animal to be protected so as to facilitate oral administration of the compound of Formula 1.

If the parasiticidal compositions are in the form of feed concentrates, the carrier is typically selected from high-performance feed, feed cereals or protein concentrates. Such feed concentrate-containing compositions can, in addition to the parasiticidal active ingredients, comprise additives promoting animal health or growth, improving quality of meat from animals for slaughter or otherwise useful to animal husbandry. These additives can include, for example, vitamins, antibiotics, chemotherapeutics, bacteriostats, fungistats, coccidiostats and hormones.

The compounds of Formula 1 may also be formulated in rectal compositions such as suppositories or retention enemas, using, e.g., conventional suppository bases such as cocoa butter or other glycerides.

The formulations for the method of this invention may include an antioxidant, such as BHT (butylated hydroxytoluene). The antioxidant is generally present in amounts of at 0.1-5% (wt/vol). Some of the formulations require a solubilizer, such as oleic acid, to dissolve the active agent, particularly if spinosad is included. Common spreading agents used in these pour-on formulations include isopropyl myristate, isopropyl palmitate, caprylic/capric acid esters of saturated $C_{12}$-$C_{18}$ fatty alcohols, oleic acid, oleyl ester, ethyl oleate, triglycerides, silicone oils and dipropylene glycol methyl ether. The pour-on formulations for the method of this invention are prepared according to known techniques. Where the pour-on is a solution, the parasiticide/insecticide is mixed with the carrier or vehicle, using heat and stirring if required. Auxiliary or additional ingredients can be added to the mixture of active agent and carrier, or they can be mixed with the active agent prior to the addition of the carrier. Pour-on formulations in the form of emulsions or suspensions are similarly prepared using known techniques.

Other delivery systems for relatively hydrophobic pharmaceutical compounds may be employed. Liposomes and emulsions are well-known examples of delivery vehicles or carriers for hydrophobic drugs. In addition, organic solvents such as dimethylsulfoxide may be used, if needed.

The rate of application required for effective parasitic invertebrate pest control (i.e. "pesticidally effective amount") will depend on such factors as the species of parasitic invertebrate pest to be controlled, the pest's life cycle, life stage, its size, location, time of year, host crop or animal, feeding behavior, mating behavior, ambient moisture, temperature, and the like. One skilled in the art can easily determine the pesticidally effective amount necessary for the desired level of parasitic invertebrate pest control.

In general for veterinary use, a compound or composition of Formula 1 is administered in a pesticidally effective amount to an animal, particularly a homeothermic animal, to be protected from parasitic invertebrate pests. A pesticidally effective amount is the amount of active ingredient needed to achieve an observable effect diminishing the occurrence or activity of the target parasitic invertebrate pest. One skilled in the art will appreciate that the pesticidally effective dose can vary for the various compounds and compositions useful for the method of the present invention, the desired pesticidal effect and duration, the target parasitic invertebrate pest species, the animal to be protected, the mode of application and the like, and the amount needed to achieve a particular result can be determined through simple experimentation.

For oral or parenteral administration to animals, a dose of a compound of the present invention administered at suitable intervals typically ranges from about 0.01 mg/kg to about 100 mg/kg, and preferably from about 0.01 mg/kg to about 30 mg/kg of animal body weight.

Suitable intervals for the administration of compounds of the present invention to animals range from about daily to about yearly. Of note are administration intervals ranging from about weekly to about once every 6 months. Of particular note are monthly administration intervals (i.e. administering the compound to the animal once every month).

The following Tests demonstrate the control efficacy of compounds of Formula 1 on specific pests. "Control efficacy" represents inhibition of parasitic invertebrate pest development (including mortality) that causes significantly reduced feeding. The pest control protection afforded by the compounds is not limited, however, to these species. See Index Tables A and B for compound descriptions.

INDEX TABLE A

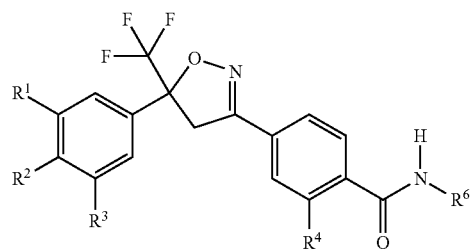

| Cmpd | $R^1$ | $R^2$ | $R^3$ | $R^4$ | $R^6$ | mp (° C.) |
|---|---|---|---|---|---|---|
| 1 | Cl | H | Cl | $CH_3$ | $CH_2$(2-pyridinyl) | 67-69 |
| 2 | Cl | H | Cl | $CH_3$ | $CH_2CH_2SCH_3$ | * |
| 3 | Cl | H | Cl | $CH_3$ | $CH_2C(O)NHCH_2CF_3$ | * |
| 4 | Cl | H | Cl | $CH_3$ | $CH(CH_3)CH_2CH_2SCH_3$ | * |
| 5 | Cl | H | Cl | $CH_3$ | $CH_2CH_2S(O)CH_3$ | * |
| 6 | Cl | H | Cl | $CH_3$ | $CH_2CH_2S(O)_2CH_3$ | * |
| 7 | Cl | H | Cl | F | $CH_2$(2-pyridinyl) | * |
| 8 | Cl | H | Cl | $CH_3$ | $C(CH_3)_2CH_2SCH_3$ | * |
| 9 | Cl | H | Cl | $CH_3$ | (R)-$CH(CH_3)C(O)NHCH_2CF_3$ | * |
| 10 | Cl | H | Cl | $CH_3$ | $C(CH_3)_2CH_2S(O)_2CH_3$ | * |

*See Index Table B for $^1$H NMR data.

INDEX TABLE B

| Compound | $^1$H NMR Data (CDCl$_3$ solution unless indicated otherwise)$^a$ |
|---|---|
| 2 | δ 7.52 (m, 4H), 7.43 (m, 2H), 6.20 (br s, 1H), 4.08 (d, 1H), 3.72 (d, 1H), 3.66 (m, 2H), 2.76 (t, 2H), 2.49 (s, 3H), 2.15 (s, 3H). |

INDEX TABLE B-continued

| Compound | $^1$H NMR Data (CDCl$_3$ solution unless indicated otherwise)$^a$ |
|---|---|
| 3 | δ 7.43-7.54 (m, 6H), 6.99 (br t, 1H), 6.75 (br t, 1H), 4.21 (d, 2H), 4.08 (d, 1H), 3.95 (m, 2H), 3.70 (d, 1H), 2.47 (s, 3H). |
| 4 | δ 7.51 (m, 4H), 7.43 (m, 2H), 5.74 (br d, 1H), 4.08 (d, 1H), 3.70 (d, 1H), 2.60 (t, 2H), 2.47 (s, 3H), 2.13 (s, 3H), 1.3 (d, 3H). |
| 5 | δ 7.5 (m, 4H), 7.43 (m, 1H), 7.0 (s, 1H), 6.84 (br s, 1H), 4.08 (d, 1H), 4.0 (m, 2H), 3.71 (d, 1H), 3.17 (m, 1H), 2.91 (m, 1H), 2.68 (s, 3H), 2.49 (s, 3H). |
| 6 | δ 7.5 (m, 4H), 7.43 (m, 2H), 7.0 (s, 1H), 6.58 (br s, 1H), 4.08 (d, 1H), 4.0 (m, 2H), 3.71 (d, 1H), 3.36 (m, 2H), 3.0 (s, 3H), 2.49 (s, 3H). |
| 7 | δ 8.6 (d, 1H), 8.2 (t, 1H), 8.1 (m, 1H), 7.7 (dt, 1H), 7.6-7.4 (m, 5H), 7.35 (d, 1H), 7.25 (m, 1H), 4.8 (d, 2H), 4.1 (d, 1H), 3.7 (d, 1H). |
| 8 | δ 7.5 (m, 4H), 7.43 (m, 2H), 5.75 (br s, 1H), 4.08 (d, 1H), 3.71 (d, 1H), 3.07 (s, 2H), 2.48 (s, 3H), 2.18 (s, 3H), 1.51 (s, 6H). |
| 9 | δ 7.36-7.51 (m, 7H), 6.85 (dd, 1H), 4.83 (m, 1H), 4.09 (d, 1H), 3.88 (m, 2H), 3.71 (d, 1H), 2.40 (s, 3H), 1.51 (d, 3H). |
| 10 | δ 7.5 (m, 5H), 7.43 (s, 1H), 6.03 (br s, 1H), 4.08 (d, 1H), 3.79 (s, 2H), 3.71 (d, 1H), 2.95 (s, 3H), 2.47 (s, 3H), 1.69 (s, 6H). |

$^a$$^1$H NMR data are in ppm downfield from tetramethylsilane. Couplings are designated by (s)—singlet, (d)—doublet, (t)—triplet, (q)—quartet, (dd)—doublet of doublets, (dt)—doublet of triplets, (br)—broad peaks, (m)—multiplet.

Methods for preparing the compounds listed in Index Table A are disclosed in PCT Patent Publication WO 2005/085216. To the extent necessary to teach the methods of preparing the compounds Formula 1, (and only to the extent that they are not inconsistent with the disclosure herein) this patent publication is herein incorporated by reference.

BIOLOGICAL EXAMPLES OF THE INVENTION

Test A

For evaluating control of the cat flea (*Ctenocephalides felis*), a CD-1® mouse (about 30 g, male, obtained from Charles River Laboratories, Wilmington, Mass.) was orally dosed with a test compound in an amount of 10 mg/kg solubilized in propylene glycol/glycerol formal (60:40). Two hours after oral administration of the test compound, approximately 8 to 16 adult fleas were applied to each mouse. The fleas were then evaluated for mortality 48 hours after flea application to the mouse.

Of the compounds tested, the following compounds resulted in at least 50% mortality: 1, 2, 3 and 4.

Test B

For evaluating control of the cat flea (*Ctenocephalides felis*), a CD-1® mouse (about 30 g, male, obtained from Charles River Laboratories, Wilmington, Mass.) was orally dosed with a test compound in an amount of 10 mg/kg solubilized in propylene glycol/glycerol formal (60:40). Twenty four hours after oral administration of the test compound, approximately 8 to 16 adult fleas were applied to each mouse. The fleas were then evaluated for mortality 48 hours after flea application to the mouse.

Of the compounds tested, the following compounds resulted in at least 20% mortality: 1, 2 and 3. The following compounds resulted in at least 50% mortality: 2 and 3.

Test C

For evaluating control of the cat flea (*Ctenocephalides felis*), a CD-1® mouse (about 30 g, male, obtained from Charles River Laboratories, Wilmington, Mass.) was subcutaneously dosed with a test compound in an amount of 10 mg/kg solubilized in propylene glycol/glycerol formal (60:40). Two hours after oral administration of the test compound, approximately 8 to 16 adult fleas were applied to each mouse. The fleas were then evaluated for mortality 48 hours after flea application to the mouse.

Of the compounds tested, the following compounds resulted in at least 20% mortality: 1, 2 and 3. The following compounds resulted in at least 50% mortality: 1 and 3.

Test D

For evaluating control of the cat flea (*Ctenocephalides felis*), a test compound was solubilized in propylene glycol/glycerol formal (60:40) and then diluted in bovine blood to a final test rate of 30 ppm. The treated blood was placed in a tube, and the bottom of the tube was covered with a membrane. Approximately 10 adult cat fleas were allowed to feed through the membrane on the treated blood. The adult fleas were then evaluated for mortality 72 hours later.

Of the compounds tested, the following compounds resulted in at least 50% mortality: 1, 2, 3, 5, 6, 7, 8, 9 and 10.

What is claimed is:

1. A method for protecting a mammal from fleas, which comprises orally administering a dosage of about 10 mg/kg to about 100 mg/kg of mammal body weight of an isoxazoline compound having the following formula:

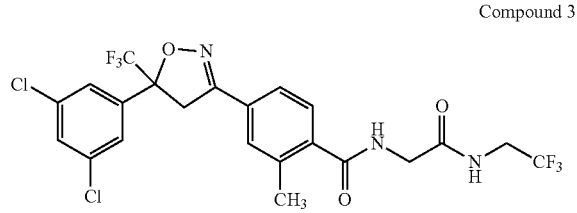 [SMILES: Cc1cc(C2=NOC(c3cc(Cl)cc(Cl)c3)(C(F)(F)F)C2)ccc1C(=O)NCC(=O)NCC(F)(F)F]

Compound 3 or a pharmaceutically acceptable salt thereof to the mammal, whereby the dosage is sufficient to protect the mammal from fleas at least 24 hours after oral administration and whereby the mortality to the fleas is at least 50%.

2. The method according to claim 1, wherein the mammal is livestock.

3. The method according to claim 1, wherein the mammal is a canine.

4. The method according to claim 1, wherein the mammal is a feline.

5. The method according to claim 1, wherein the mammal is a cat or dog.

* * * * *